US011278235B2

(12) United States Patent
Herr et al.

(10) Patent No.: US 11,278,235 B2
(45) Date of Patent: Mar. 22, 2022

(54) NEURAL EFFERENT AND AFFERENT CONTROL OF SPRING EQUILIBRIUM, DAMPING, AND POWER IN BACKDRIVABLE AND NON-BACKDRIVABLE SERIES-ELASTIC ACTUATORS COMPRISING VARIABLE SERIES STIFFNESS MECHANISMS

(71) Applicant: Massachusetts Institute of Technology, Cambridge, MA (US)

(72) Inventors: Hugh M. Herr, Somerville, MA (US); Matthew Eli Carney, Somerville, MA (US); Emily Ann Rogers, Somerville, MA (US); Lucy Wei Du, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 6 days.

(21) Appl. No.: 16/661,483

(22) Filed: Oct. 23, 2019

(65) Prior Publication Data
US 2020/0129314 A1 Apr. 30, 2020

Related U.S. Application Data

(60) Provisional application No. 62/749,230, filed on Oct. 23, 2018.

(51) Int. Cl.
*A61B 5/389* (2021.01)
*A61B 5/00* (2006.01)
(Continued)

(52) U.S. Cl.
CPC ............. *A61B 5/389* (2021.01); *A61B 5/688* (2013.01); *A61F 2/64* (2013.01); *A61F 2/6607* (2013.01);
(Continued)

(58) Field of Classification Search
CPC .......... A61B 5/0488; A61B 5/688; A61F 2/64; A61F 2/6607; A61F 2/72;
(Continued)

(56) References Cited

U.S. PATENT DOCUMENTS 8,551,184 B1 10/2013 Herr
8,734,528 B2 5/2014 Herr et al.
(Continued)

FOREIGN PATENT DOCUMENTS

TW      201023842 A1   7/2010
WO      2015157723 A1  10/2015
WO   WO 2018/089543 A1   5/2018

OTHER PUBLICATIONS

International Search Report and Written Opinion for International Application No. PCT/US2019/057669, entitled "Neural Efferent and Afferent Control of Spring Equilibrium, Damping, and Power in Backdrivable and Non-Backdrivable Series-Elastic Actuators Comprising Variable Series Stiffness Mechanisms," consisting of 17 pages, dated Jun. 23, 2020.

(Continued)

*Primary Examiner* — Yashita Sharma
*Assistant Examiner* — Mihret Tafesse
(74) *Attorney, Agent, or Firm* — Hamilton, Brook, Smith & Reynolds, P.C.

(57) ABSTRACT

A prosthetic device includes a frame defining an output axis, a cantilever beam spring attached to the frame, a moment arm attached to the spring, and a rigid output arm coupled to the frame and rotatable about the output axis. A connector assembly is configured to apply a moment to the cantilever beam spring via the moment arm while applying a torque about the output axis via the output arm. An ankle-foot device includes foot and ankle members connected for two-degree of freedom movement relative to one another, (Continued)

allowing for rotation about an ankle axis and rotation about a subtalar axis. Two linear actuators, each coupled to corresponding series elastic element, link the foot and ankle members. Driving the actuators in the same direction causes rotation about the ankle axis and driving the actuators in opposing directions causes rotation about the subtalar axis. A processor receives sensory information from a sensor and drives the actuators to control an equilibrium position of the series elastic elements. A rotary actuator for a prosthetic device includes a housing frame, a motor mounted within the housing frame, and a cycloidal drive coupled to the motor within the housing frame. A torsion shaft can extend through the actuator to an output and provide a series elastic element.

24 Claims, 42 Drawing Sheets

(51) Int. Cl.
  *A61F 2/72*  (2006.01)
  *G06F 3/01*  (2006.01)
  *A61F 2/64*  (2006.01)
  *A61F 2/66*  (2006.01)
  *A61F 2/74*  (2006.01)

(52) U.S. Cl.
  CPC ............... *A61F 2/72* (2013.01); *G06F 3/015* (2013.01); *A61F 2/741* (2021.08); *A61F 2002/6664* (2013.01)

(58) Field of Classification Search
  CPC ........ A61F 2002/6664; A61F 2002/741; A61F 2002/7615; A61F 2002/7837; A61F 2002/7875; A61F 2/7812; A61F 2/76; A61F 2002/701; A61F 2002/704; G06F 3/015
  See application file for complete search history.

(56) References Cited

U.S. PATENT DOCUMENTS

| | | | |
|---|---|---|---|
| 8,870,967 B2 | 10/2014 | Herr et al. | |
| 9,339,397 B2 | 5/2016 | Herr et al. | |
| 10,342,681 B2 | 7/2019 | Herr et al. | |
| 10,806,602 B2* | 10/2020 | Rouse | A61F 2/6607 |
| 2007/0156252 A1* | 7/2007 | Jonsson | A61F 2/6607 623/24 |
| 2011/0257764 A1* | 10/2011 | Herr | A61F 2/68 623/24 |
| 2013/0310949 A1* | 11/2013 | Goldfarb | A61F 2/60 623/27 |
| 2014/0243997 A1* | 8/2014 | Clausen | A61F 2/66 623/55 |
| 2017/0156252 P1 | 6/2017 | Suphachadiwong | |
| 2019/0175365 A1 | 6/2019 | Herr et al. | |
| 2019/0307583 A1 | 10/2019 | Herr et al. | |
| 2019/0321201 A1 | 10/2019 | Herr et al. | |

OTHER PUBLICATIONS

Pratt et al., "Series elastic actuators," IEEE, vol. 1, pp. 399-406, 1995.
Alexander, "Three Uses for Springs in Legged Locomotion," Int. J. Rob. Res., vol. 9, No. 2, pp. 53-61, 1990.
Paluska et al., "The effect of series elasticity on actuator power and work output: Implications for robotic and prosthetic joint design," Rob. Auton. Syst., vol. 54, pp. 667-673, 2006.
Meijneke et al., "Introducing a Modular, Personalized Exoskeleton for Ankle and Knee Support of Individuals with a Spinal Cord Injury," Springer, 2017, pp. 169-173.
Orekhov et al., "An unlumped model for linear series elastic actuators with ball screw drives," IEEE/RSJ International Conference on Intelligent Robots and Systems (IROS), pp. 2224-2230, 2015.
Paluska et al., "Series elasticity and actuator power output," Proc.—IEEE Int. Conf. Robot. Autom., vol. 2006, pp. 1830-1833, 2006.
Scarfogliero et al., "Design and development of the long-jumping "grillo" mini robot," IEEE Int. Conf. Robot. and Auto., pp. 467-472, 2007.
Wahl, "Flat and Leaf Springs," Mechanical Springs, 2nd ed., Chapter 16, Cleveland, Ohio: Penton Publishing Company, pp. 286-313, 1949.
Wahl, "Energy-Storage Capacity of Various Springs," Mechanical Springs, 2nd ed., Chapter 22, Cleveland, Ohio: Penton Publishing Company, pp. 399-412, 1949.
Wahl, "Spring Materials," Mechanical Springs, 2nd ed., Chapter 23, Cleveland, Ohio: Penton Publishing Company, pp. 413-426, 1949.
Au et al., "Powered Ankle-Foot Prosthesis," IEEE Robot. Autom. Mag., No. September, pp. 52-59, 2008.
Collins et al., "An ankle-foot prosthesis emulator with control of plantarflexion and inversion-eversion torque," Proc.—IEEE Int. Conf. Robot. Autom., pp. 1210-1216, 2015.
Browning et al., "The effects of adding mass to the legs on the energetics and biomechanics of walking," Med. Sci. Sports Exerc., vol. 39, No. 3, pp. 515-525, 2007.
Farina et al., "Neural Control of Movement: The extraction of neural strategies from the surface EMG," J. Appl Physiol., vol. 96, No. 4, pp. 1486-1495, 2004.
Geethanjali, "Myoelectric control of prosthetic hands: State-of-the-art review," Med. Devices Evid. Res., vol. 9, pp. 247-255, 2016.
Farina et al., "The Extraction of Neural Information from the Surface EMG for the Control of Upper-Limb Prostheses : Emerging Avenues and Challenges," Neural Syst. . . . , vol. 22, No. 4, pp. 797-809, 2014.
Benatti et al., "A Versatile Embedded Platform for EMG Acquisition and Gesture Recognition," IEEE Trans. Biomed. Circuits Syst., vol. 9, No. 5, pp. 620-630, 2015.
Milosevic et al., "Design challenges for wearable EMG applications," Proc. 2017 Des. Autom. Test Eur. Date 2017, pp. 1432-1437, 2017.
Benatti et al., "A sub-10mW real-Time implementation for EMG hand gesture recognition based on a multi-core biomedical SoC," Proc.—2017 7th Int. Work. Adv. Sensors Interfaces, IWASI 2017, pp. 139-144, 2017.
Mastinu et al., "Embedded System for Prosthetic Control Using Implanted Neuromuscular Interfaces Accessed Via an Osseointegrated Implant," IEEE Trans. Biomed. Circuits Syst., vol. 11, No. 4, pp. 867-877, 2017.
Knabe et al., "Design of a Compact, Lightweight, Electromechanical Linear Series Elastic Actuator," in ASME. International Design Engineering Technical Conferences and Computers and Information in Engineering Conference, Volume 5B: 38th Mechanisms and Robotics Conference, pp. 1-8, 2014.
Orekhov, "Series Elasticity in Linearly Actuated Humanoids Series Elasticity in Linearly Actuated Humanoids," Virginia Tech, 2014.
Paine et al., "Design and Control Considerations for High-Performance Series Elastic Actuators," IEEE/ASME Trans. Mechatronics, vol. 19, No. 3, pp. 1080-1091, 2014.
Hogan, "Impedance Control: An Approach to Manipulation; Part II—Implementation," J. Dyn. Syst. Meas. Control, vol. 107, No. Jun. 1983, pp. 1-24, 1985.
Markowitz et al., "Speed adaptation in a powered transtibial prosthesis controlled with a neuromuscular model," Philos. Trans. R. Soc. Lond. B. Biol. Sci., vol. 366, No. 1570, pp. 1621-1631, 2011.
Hargrove et al., "Robotic Leg Control with EMG Decoding in an Amputee with Nerve Transfers," N. Engl. J. Med., vol. 369, No. 13, pp. 1237-1242, Sep. 2013.
Au et al., "An EMG-position controlled system for an active ankle-foot prosthesis: an initial experimental study," IEEE—9th International Conf. on the Rehab. Robotics, pp. 375-379, 2005.
Clancy et al., "Single-channel techniques for information extraction from the surface EMG signal," Institute for Electrical and Electron-

(56) References Cited

OTHER PUBLICATIONS ics Engineers, Inc.: Electromyography: Physiology, Engineering, and Noninvasive Applications, pp. 133-168, 2004.
Botsiber et al., "Design and Performance of the Cycloid Speed Reducer," Mach. Des., No. June, pp. 65-69, 1956.
Alam et al., "Mechanism and Design Analysis of Articulated Ankle Foot Orthoses for Drop-Foot," The Scientific World Journal, 2014.
Novak et al., "Stair negotiation alters stability in older adults," Lower Extremity Review Magazine, 2010.
Huang et al., "Continuous Locomotion-Mode identification for Prosthetic legs based on Neuromuscular-Mechanical fusion," IEEE Transactions on Biomedical Engineering, vol. 58, No. 10, pp. 2867-2875, 2011.
Tkach et al., "Neuromechanical sensor fusion yields highest accuracies in predicting ambulation mode transitions for trans-tibial amputees," Annual International Conference of the IEEE, 2013.
Young et al., "Analysis of using EMG and mechanical sensors to enhance intent recognition in powered lower limb prostheses," Journal of Neural Engineering, vol. 11, No. 5, 2014.
Hargrove et al., "Intuitive Control of a Powered Prosthetic Leg During Ambulation," Journal of the American Medical Association, vol. 313, No. 22, pp. 2244-2252, 2015.
Krausz et al., "Depth Sensing for Improved Control of Lower Limb Prostheses," IEEE Transactions on Biomedical Engineering, vol. 62, No. 11, p. 2576-2587, 2015.
Spanias et al., "Detection of and Compensation for EMG Disturbances for Powered Lower Limb Prosthesis Control," IEEE Transactions on Neural Systems and Rehabilitation Engineering, vol. 24, No. 2, 2016.
Liu et al., "Development of an environment-aware Locomotion mode recognition system for powered lower limb Prostheses," IEEE Transactions on Neural Systems and Rehabilitation Engineering, vol. 24, No. 4, pp. 434-443, 2016.
Young et al., "A Classification Method for User-Independent Intent Recognition for Transfemoral Amputees Using Powered Lower Limb Prostheses," IEEE Transactions on Neural Systems and Rehabilitation Engineering, vol. 24, No. 2, pp. 217-225, 2016.
Zheng et al., "Noncontact Capacitive Sensing-Based Locomotion Transition Recognition for Amputees With Robotic Transtibial Prostheses," IEEE Transactions on Neural Systems and Rehabilitation Engineering, vol. 25, No. 2, pp. 161-170, 2017.
Spanias et al., "Online adaptive neural control of a robotic lower limb prosthesis," Journal of Neural Engineering, vol. 15, No. 1, 2018.
Li et al., "Gait Mode Recognition and Control for a Portable-Powered Ankle-Foot Orthosis," IEEE 13th International Conference on Rehabilitation Robotics (ICORR), 2013.
Yuan et al., "Fuzzy-logic-based terrain identification with Multisensor fusion for Transtibial Amputees," IEEE/ASME Transactions on Mechatronics, vol. 20, No. 2, pp. 618-630, 2015.
Stolyarov et al. "Translational Motion Tracking of Leg Joints for Enhanced Prediction of terrains," IEEE Transactions on Biomedical Engineering, vol. 65, No. 4, pp. 763-769, 2018.
Zhang et al. "An Automatic and User-Driven Training Method for Locomotion Mode Recognition for Artificial Leg Control," 2012 Annual International Conference of the IEEE Engineering in Medicine and Biology Society, 2012.
Ottobock, "Advanced prosthetic feet—at a glance," 2018.
"The BiOM Advantage—BionX Medical Technologies," 2017. [Online]. http://www.bionxmed.com/payer/the-biom-advantage/ [Accessed: Nov. 11, 2017]. Archived at: https://web.archive.org/web/20171025055338/http://www.bionxmed.com/payer/the-biom-advantage/ [Retrieved Jan. 27, 2020].
Winter, "Biomechanical Motor Patterns in Normal Walking," J. Mot. Behav., vol. 15, No. 4, pp. 302-330, 1983.
Lester et al., "Sensing and modeling activities to support physical fitness," UbiComp '05 Workshop: W10—Monitoring, Measuring, & Motivating, pp. 5-8, 2005.
LaPrè et al., "A Robotic Ankle-Foot Prosthesis With Active Alignment," J. Med. Device., vol. 10, No. 2, p. 025001, 2016.
Holgate et al., "The SPARKy (spring ankle with regenerative kinetics) project: Choosing a DC motor based actuation method," Proc. 2nd Bienn. IEEE/RAS-EMBS Int. Conf. Biomed. Robot. Biomechatronics, BioRob 2008, pp. 163-168, 2008.
Zhu et al., "PANTOE II: Improved Version of a Powered Transtibial Prosthesis With Ankle and Toe Joints," in Proceedings of the 2018 Design of Medical Devices Conference, pp. 1-3, 2018.
Carney et al. "Design and Preliminary Results of a Reaction Force Series Elastic Actuator for Bionic Ankle Prostheses," engrXiv, Preprint available online: https://doi.org/10.31224/osf.io/3wt5j; pp. 1-15, accessed: Oct. 19, 2019.
Orekhov et al., "Configurable compliance for series elastic actuators," Proceedings of the ASME 2013 International Design Engineering Technical Conferences and Computers and Information in Engineering Conference, IDETC/CIE, 2013.
Invitation to Pay Additional Fees and, Where Applicable, Protest Fee, Appl. No. PCT/US2019/057669, "Neural Efferent and Afferent Control of Spring Equilibrium, Damping, and Power in Backdrivable and Non-Backdrivable Series-Elastic Actuators Comprising Variable Series Stiffness Mechanisms", dated Mar. 11, 2020.
International Preliminary Report on Patentability for International Application No. PCT/US2019/057669, "Neural Efferent and Afferent Control of Spring Equilibrium, Damping, and Power in Backdrivable and Non-Backdrivable Series-Elastic Actuators Comprising Variable Series Stiffness Mechanisms" dated May 6, 2021.

\* cited by examiner

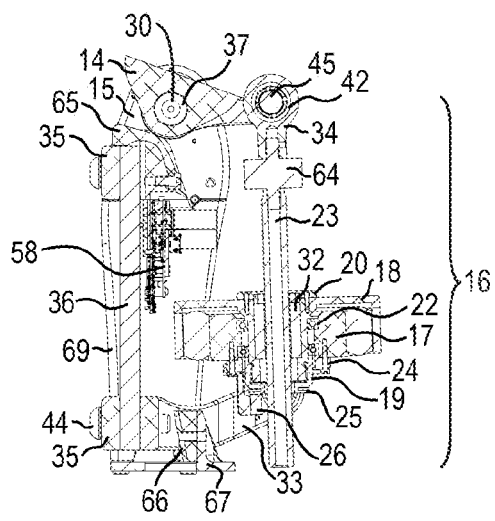
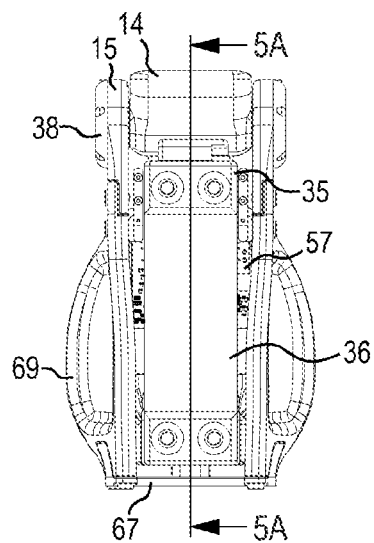
FIG. 5A
FIG. 5B
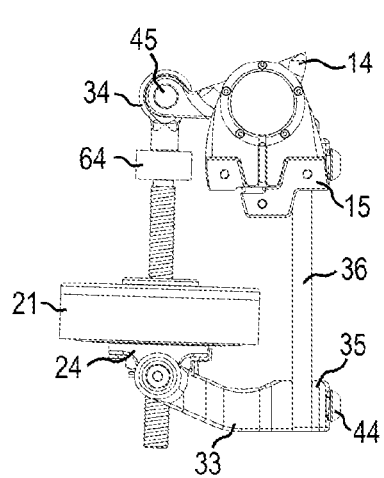
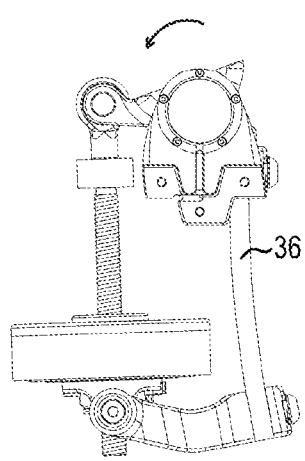
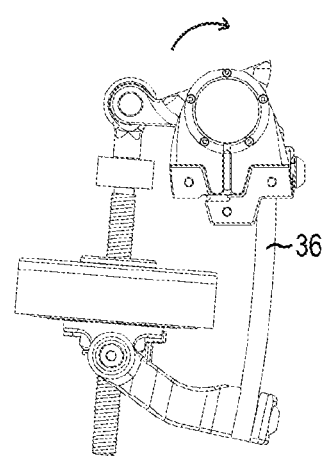
FIG. 6A
FIG. 6B
FIG. 6C

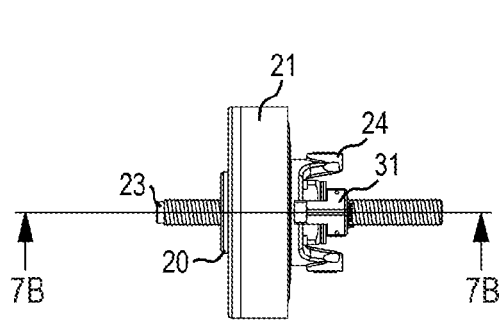
FIG. 7A
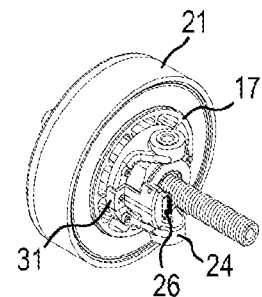
FIG. 7C
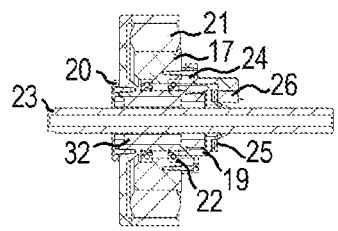
FIG. 7B
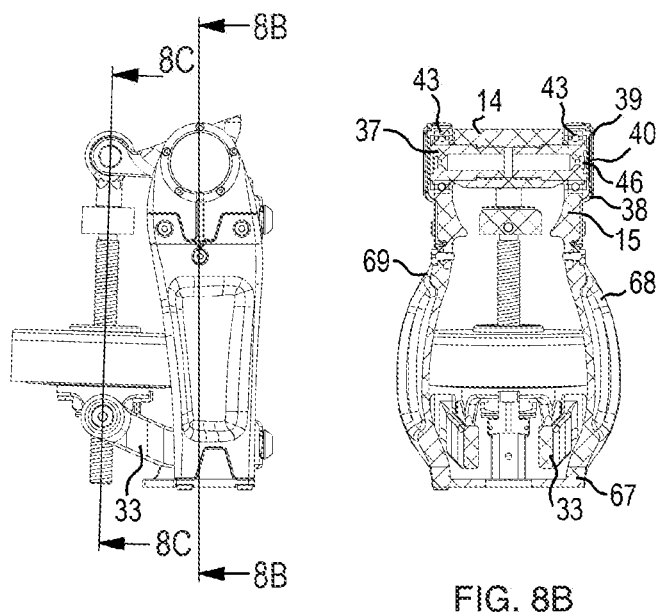
FIG. 8A
FIG. 8B
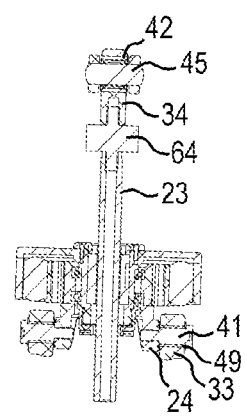
FIG. 8C

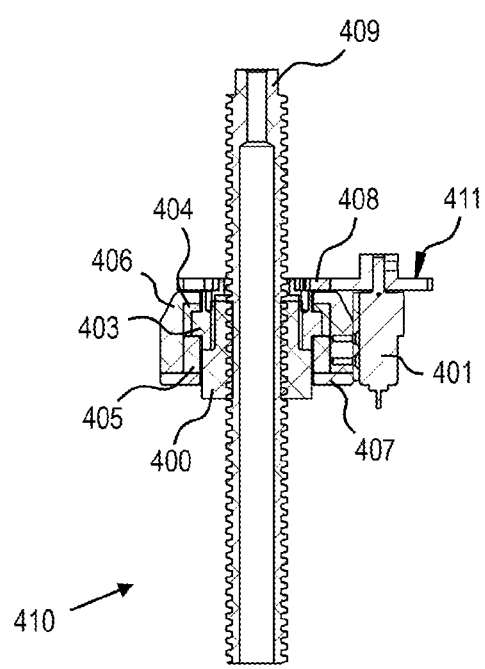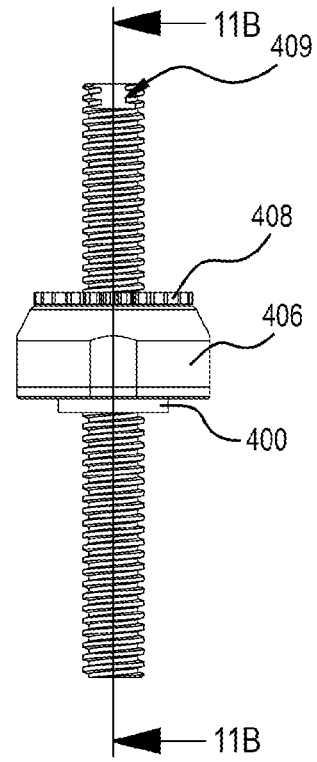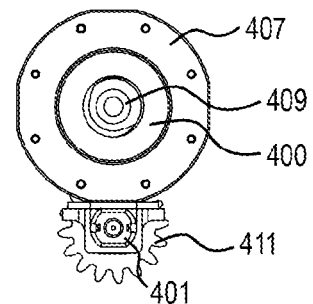
FIG. 11B
FIG. 11A
FIG. 11C

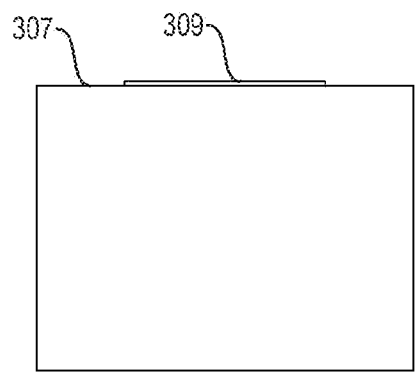
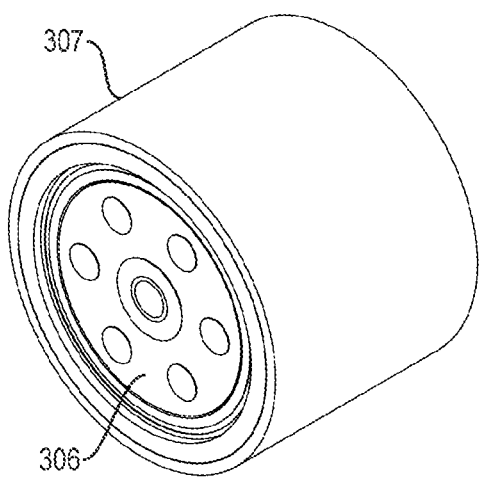
FIG. 35C
FIG. 35D
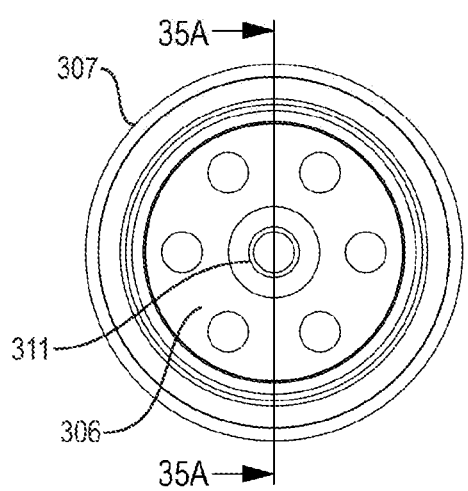
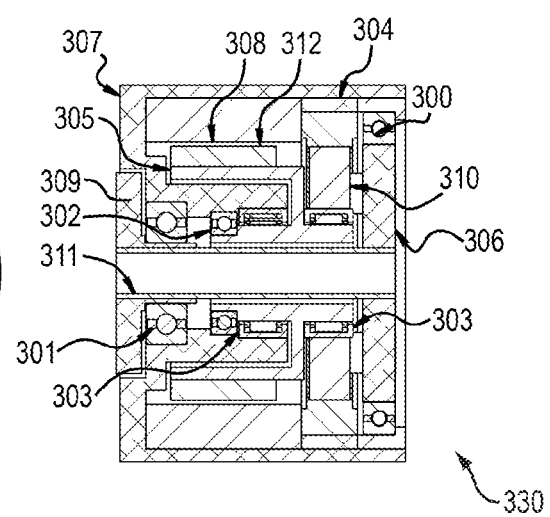
FIG. 35B
FIG. 35A

NEURAL EFFERENT AND AFFERENT CONTROL OF SPRING EQUILIBRIUM, DAMPING, AND POWER IN BACKDRIVABLE AND NON-BACKDRIVABLE SERIES-ELASTIC ACTUATORS COMPRISING VARIABLE SERIES STIFFNESS MECHANISMS

RELATED APPLICATION

This application claims the benefit of U.S. Provisional Application No. 62/749,230, filed on Oct. 23, 2018. The entire teachings of the above application are incorporated herein by reference.

GOVERNMENT SUPPORT

This invention was made with government support under Grant No.: W911NF-17-2-0043 from DARPA. The government has certain rights in the invention.

BACKGROUND

Series elastic actuators (SEA) developed at the MIT Leg Lab in 1990s have found wide-spread use in robotic systems and in particular humanoid robotic systems where physical interaction and contact dynamics benefit from force control and low inertia end-effectors. Initially these SEA technologies were used to decouple the often-large inertia of the drive-train from the output end-effector. It has also been found that the series elastic element is biomimetic in that it can be used to store energy much like tendons store energy in mammalian muscle tendon units—this is seen for instance in the Achilles tendon stretch during the mid to late stance phase of bipedal locomotion, or the windup for a baseball pitch. In robotics, the goal is generally to maximize output power, bandwidth, and control fidelity while minimizing mass and energy consumption.

One benefit of the series elastic element is force control fidelity that comes from measuring the displacement of an elastic element and relating that to Hooke's Law or another non-linear force/displacement relationship to determine force at the joint. This elastic element in series with the actuator decouples the input and output physical impedance by providing an allowable relative displacement between the output and input drive. The series elastic element enables a relative displacement between the output and input, allowing the gear-train time to get out of its own way when responding to a disturbance at the output. This simplifies the contact dynamic control strategy at impact with a hard surface. The softer the elastic element the more disturbance is allowed, and easier measurement can be made, but similarly, the faster the prime-mover must accelerate to get out of its own way when reversing direction. This tradeoff is a limit to the output bandwidth (operating frequency at which maximum force/torque can be provided) when a fully reversed load requires the motor and gear-train to completely reverse direction to travel the additional reversed displacement of the elastic element. The larger the gear-ratio, or the larger the motor inertia, the more power is required to accelerate the motor and drivetrain in the reverse direction—in fact the gear ratio contributes a $N^2$ factor to the inertia measured at the output. Overall system performance is, thus affected by gear ratio as well as the stiffness of the elastic element.

The secondary benefit that can be at odds with the force-fidelity and impedance decoupling benefit is that of energy storage and power release—the catapult effect. Energy can be stored in the elastic element and then released by modulating the actuator. This happens somewhat naturally in cyclic motions, such as flexion and extension of joints in human walking gait, or a control algorithm can cause the actuator to preload or pre-compress the elastic element in preparation for a larger power release. By storing and releasing some mechanical energy in the spring the electrical power requirements of the motor can be reduced. The ideal case is to store all of the reversed loading in an elastic element such that the motor must only provide the net positive energy required for the desired output vector as well as overcoming frictional losses.

Mobile or wearable robotic systems including humanoids, exoskeletons, and powered prostheses have made use of these series elastic actuators specifically for the force control and energy efficiency.

SUMMARY

A prosthetic device includes a frame defining an output axis, a cantilever beam spring having a first end attached to the frame and a second end, and a moment arm attached to the second end of the spring. A rigid output arm is coupled to the frame and rotatable about the output axis. A connector assembly connects the moment arm to the output arm. The connector assembly is coupled to the moment arm by a moment pivot and coupled to the output arm by an output pivot located at a distance from the output axis. The connector assembly is configured to apply a moment to the cantilever beam spring via the moment arm while applying a torque about the output axis via the output arm.

The connector assembly can be configured to vary the distance between the moment pivot and the output pivot or can be configured to set the distance between moment pivot and the output pivot at a fixed length.

The connector assembly can include a linear actuator. In general, the connector assembly includes a mechanical transformer that converts rotary motion into linear motion.

In certain embodiments, the mechanical transformer is backdriveable. In a particular example, the mechanical transformer includes a motor, a screw passing through the motor, and a nut rotatable about the screw, the motor configured to rotate the nut, rotation of the nut causing linear motion of the screw relative to the motor.

The linear motion of the screw creates load on the output arm and rotary motion of the output arm about the frame. The motor can include a rotor and the nut can be integrated into the rotor, rotation of the rotor causing the linear motion of the screw. The motor can include a stator coupled to the moment pivot at the moment arm, and an end of the screw can be coupled via a push rod to the output pivot at the output arm. The device can include a load cell between the screw and the push rod, to measure load on the screw. The device can further include a rotary encoder at the frame to measure rotation of the output arm about the frame.

The nut rotation causes the screw to move linearly relative to the motor. In other words, the motor position is relatively constant, being located at the moment pivot, but the rotary output rotates by the output pivot moving up and down as the screw is driven up and down by the rotation of the nut.

In certain embodiments, the mechanical transformer is non-backdriveable. For example, the mechanical transformer can include a screw and a nut configured to rotate about the screw, rotation of the nut causing linear motion of the screw.

The mechanical transformer can include a motor configured to provide rotation of the nut the rotation of the nut can be by means of meshing gears, friction drive, or belt drive transforming motion of the motor to rotation of the nut.

The beam spring of the device can be configured as a variable stiffness beam spring. For example, the device can include a carriage and a rotatable beam screw that extends parallel to the beam spring and engages a nut coupled to the carriage, rotation of the beam screw causing linear motion of the carriage along a length of the beam spring, the carriage forming a structural pivot for dynamic control of the deformation of the beam spring. A drive motor can be coupled to the beam screw for providing rotation of the beam screw.

In another example, the device includes a carriage and a shock absorber that extends parallel to the beam spring and engages the carriage, the shock absorber providing linear motion of the carriage along a length of the beam spring, the carriage forming a structural pivot for dynamic control of the deformation of the beam spring.

In general, the device finds application as a prosthetic ankle, knee, shoulder or part of a shoulder, elbow, or wrist joint. In an embodiment, the device is a prosthetic ankle device and the output arm engages a prosthetic foot. In another embodiment, the device is a prosthetic knee device and the output arm engages a prosthetic limb or a prosthetic socket. A prosthetic leg can include a knee device and the ankle device.

The device can include one or more support arms attached to the frame and supporting a base plate, wherein the base plate supports an attachment for a prosthetic limb or a prosthetic socket. In a particular example, a prosthetic socket that is attached at the base plate of the device. The prosthetic socket can be custom built socket that includes a battery mount fixture to secure a battery at the socket and further includes an electronics mount fixture to secure electronic circuitry powered by the battery at the socket.

An ankle-foot device includes a foot member and an ankle member that are connected for two-degree of freedom movement relative to one another allowing for rotation about an ankle axis and rotation about a subtalar axis, to thereby define an ankle joint and a subtalar joint. The device includes two linear actuators, each actuator including a motor and a non-backdriveable transmission, each actuator coupled at one end to the foot member and at the other end to a corresponding series elastic element attached to the ankle member, wherein driving the actuators in the same direction causes rotation about the ankle axis and driving the actuators in opposing directions causes rotation about the subtalar axis. The device further includes at least one sensor and a processor communicatively linked to the actuators and the at least one sensor. The processor is configured to receive sensory information from the at least one sensor and drive the actuators to control an equilibrium position of the series elastic elements during a swing phase of a gait cycle to improve ankle-foot device function during a subsequent stance phase of the gait cycle.

In the ankle-foot device, the ankle and subtalar axes can be orthogonal to each other. The foot member and the ankle member can be connected through a universal joint, in which case the ankle and subtalar axes can intersect at the universal joint. In additional to driving both actuators in opposing direction, drawing one actuator in one direction while driving the other actuator to hold its position can cause rotation about the subtalar axis.

The at least one sensor can include a joint position sensor, a motor position sensor, a load cell, or an inertial measurement unit (IMU). Alternatively, or in addition, the at least one sensor includes an electromyographic sensor. In general, the device can include a combination of intrinsic sensors and extrinsic sensors. An example of an intrinsic sensor a joint position sensor or a load cell. An example of an extrinsic sensor is an electromyographic sensor.

The processor can be configured to adapt the equilibrium position to environmental conditions including walking speed, surface terrain, or combinations thereof. The processor can be configured to turn off the motors once the equilibrium position has been adapted during the swing phase, to conserve power-supply energy during the subsequent stance period.

The foot member of the ankle-foot device can include a base plate coupled to a prosthetic foot.

Each actuator can be configured to apply a moment to the corresponding series elastic element. Each series elastic element can be a cantilever beam spring or can be formed in a bracket coupling the ankle member to the actuators. Each actuator can be coupled to the corresponding series elastic element through a universal joint.

The transmission of each actuator can include a leadscrew interfacing with a nut, the motor of the actuator rotating the leadscrew and causing the nut to translate linearly, the nut coupled to the foot member through a universal joint.

A rotary actuator includes a housing frame, a motor mounted within the housing frame and including a rotor and a stator, and a cycloidal drive coupled to the motor within the housing frame. The rotor includes an eccentric hub portion. The cycloidal drive includes a rotary bearing mounted on the eccentric hub portion, a cycloidal disk riding on the rotary bearing and including holes, a roller housing that is configured to interact with the cycloidal disk to cause rotation of the disk; and an output shaft driven by the cycloidal disk, the output shaft coupled to the cycloidal disk via output pins that extend through the holes of the cycloidal disk.

The stator of the rotary actuator can be mounted to the housing. The rotor can include an inner hub and an outer rim that carries rotor magnets, the hub defining the eccentric hub portion and being is axially secured to the housing by bearings. The outer rim of the rotor can be configured to rotate within the stator or the outer rim of the rotor can be configured to rotate about the stator.

The cycloidal disk can include a circumferential track that engages rollers of the roller housing, the rollers causing the cycloidal disk to traverse in a counter rotating direction relative to the rotor's direction of rotation. The rollers can be static and formed integrally with the roller housing. Alternatively, the rollers can be rotatably mounted in the roller housing. In certain embodiments, the cycloidal disk and the roller housing are positioned within the stator.

The rotary actuator can further include a torsion shaft attached at one end to the output shaft and extending from the output shaft through the actuator. An output disk can be attached to the other end of the torsion shaft. The torsion shaft can be a series elastic torsion element, in which case the rotary actuator functions as a series elastic actuator. In certain embodiments the torsion shaft is a rigid shaft. In that case, a spring can be coupled to an output of the rotary actuator to provide a series elastic element.

The rotary actuator can include multiple disks, the rotary bearing can be a first rotary bearing mounted on a first eccentric hub portion of the rotor and the cycloidal disk can be a first cycloidal disk riding on the first rotary bearing. A second rotary bearing can be mounted on a second eccentric hub portion of the rotor and a second cycloidal disk riding on the second rotary bearing.

The housing frame can include an inlet port and an outlet port to allow circulation of cooling fluid through at least a portion of the actuator, e.g., a sealed interior spaced. For example, the rotary actuator may be constructed in a manner to provide the sealed interior space, for example by using sealed bearing.

A prosthetic device is provided that includes any of the rotary actuators described herein. The prosthetic device can include a first structural mount attached to the housing frame and second structural mount attached to an output of the rotary actuator. The output can be coupled to the output shaft through a torsion shaft.

The prosthetic device including the rotary actuator can be an ankle device comprising a prosthetic foot connected to the second structural mount. The prosthetic foot can include a spring to provide serial elasticity. One or more strain gauges mounted on the spring can be provided to measure deflection of the spring.

A prosthetic ankle device includes a rotary actuator defining an ankle axis of rotation, the rotary actuator including a housing frame, a motor mounted within the housing frame, a rotary output, and a cycloidal drive positioned within the housing frame and coupling the motor to the rotary output. A prosthetic foot is connected to the rotary output, and the rotary actuator is configured to rotate the prosthetic foot about the ankle axis of rotation. The rotary actuator can include a shaft extending through the motor and the cycloidal drive, the shaft coupling the cycloidal drive to the output of the actuator.

Embodiments of the invention include features that provide several advantages. The Moment-coupled Cantilever Beam Series Elastic Actuator (MCB-SEA) has useful features, such as a motor with a rotary ballnut integrated directly into the rotor allowing a screw to pass through the center of the motor, and a moment coupled cantilever beam series elastic element. The pass-through screw reduces the extra mass, volume and number of components of a standard ballscrew configuration that generally requires an offset motor and belt coupled to the screw. The moment couple applies the linear screw reaction force to the series elastic element in a way that maximizes material utilization for energy storage by inducing a constant strain deformation across the entire length of the spring.

The 2-degree of freedom non-backdrivable ankle-foot prosthesis for free space position control has several useful features. The non-backdrivable transmission allows for a low power, low mass system while leveraging the functional benefits of modulated ankle and subtalar angle position and stiffness. In addition, when paired with a portable EMG processing board, the device can be controlled volitionally by the user based on their muscle activation signals. This allows for volitional position control of the ankle and subtalar joint during walking or any other form of locomotion. In another embodiment, the device may be used independently from EMG input, with a control system that adjusts foot position during swing based on sensor values. One configuration of this invention includes the system as a series elastic actuator, allowing for tuning of the spring equilibrium point during swing as well as energy storage in the spring during relevant portions of the gait cycle.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale; emphasis instead being placed upon illustrating embodiments.

FIG. 5A is a cutaway view and FIG. 5B a front view of the MCB-SEA, shown without a prosthetic foot. The orientation of the device is flipped and similar to the knee system of FIG. 1.

FIG. 6A is a side view of the MCB-SEA with one side support removed.

FIGS. 6B and 6C illustrate flex of the cantilever beam due to torque at the output.

FIGS. 7A, 7B, and 7C are side, sectional, and perspective views, respectively, of the integrated motor and screw system of the actuator of FIG. 6A.

FIGS. 8A and 8B are side and cross-section views of the output bearing stack and the linear actuator bearing arrangements. FIG. 8C is a sectional view of the linear actuator.

FIGS. 11A-11C illustrate details of the rotary to linear transformer of FIG. 10.

FIGS. 35A, 35B, 35C, and 35D are sectional, front, side, and perspective views, respectively, of a rotary actuator composed of an internal rotor electric motor combined with a cycloidal transmission framed within the same housing.

DETAILED DESCRIPTION

Figure 1:
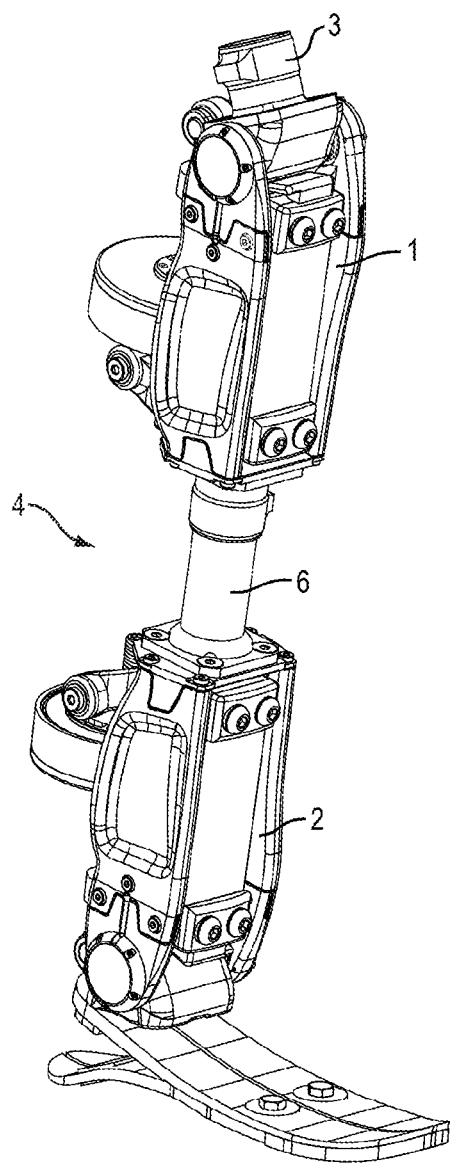
FIG. 1 shows a dynamic walking Moment-coupled Cantilever Beam Series Elastic Actuator (MCB-SEA) arranged as both a knee and ankle system.

A description of example embodiments follows.

Powered actuators for robotic or prosthetic joints can generate joint torques by means of a rotary actuator or a linear actuator that applies a force at a distance about the joint, thereby generating torque. The actuator must not explicitly store energy in an elastic element. It is feasible for the actuator to control joint torque by means of high fidelity control, enabling stiff load cells to measure output force or torque, or it is also possible to measure the current flowing into the motor and use this as a proxy for torque at the joint and the forces through the transmission that result in required motor torque that sinks the measured current.

In order to achieve optimal energy efficiency in all use cases one might want to tune the spring properties to the task at hand. Similarly, when sizing to an individual one might want to tune both the spring stiffness as well as the transmission ratio, or just the transmission or reduction ratio to tune user operating conditions to optimal drive-train and motor operating conditions. Increased user mass generally results in increased torque requirements at the joints, and a single motor can be made to operate more optimally by utilizing a gear ratio that balances torque and speed requirements as the drivetrain is coupled to the output load through the series elasticity. Deformation of a material or the strain in a material is how a spring stores energy. A high efficiency spring is one that has maximum material utilization (the majority of the material mass of the spring is being strained) as well as low internal damping (measured as hysteresis that appears in the energy recovery from the material). The best utilization of energy in a spring is by applying a moment to a beam such that the material has a constant bending moment across its entire length.

The mass of the motor and gear train in series with a spring acts as a sprung mass that has a natural frequency of oscillation. When a low-damped system is excited near its natural frequency it can become unstable. Further, as the frequency of excitation increases beyond the natural frequency the ability to apply maximum load is diminished, with increasing frequency reducing the phase margin such that the system can become completely uncontrollable. For the ambulating robotic actuator example, slow walking would benefit from storing maximum energy, while fast walking or running would benefit more from fast response. The springs built into the series elastic actuator define a set sprung mass, and a set natural frequency, and often this frequency is near the frequency of operation for walking actuators. In order for an actuator to be able to operate in both efficient and high-speed modes a series elastic actuator comprising a variable stiffness spring can be utilized. The variable series stiffness actuator is described herein where the sprung length of a cantilever is adjusted to match desired performance.

Mobile robotic systems including humanoids, exoskeletons, and powered prostheses have made use of these series elastic actuators specifically for the force control and energy efficiency. In all of these cases distal mass has a substantial impact on overall system requirements. Inertial properties of mass increase with the distance squared. In a robotic system this means more power is required to move around the same mass as its distance from pivot increases. In a powered prosthesis this means the user must expend more energy to move a heavier limb. Since the primary purpose of a powered prosthesis is to return the user towards a biologically accurate gait with minimal energy expenditure, increased distal mass is contrary to the needs of the user. To achieve this goal, components that must not be onboard the actuator, such as battery and even electronics control modules can be relocated to a more proximal location on the socket. To accomplish this goal, features can be included on the socket to attach removable battery packs and semi-permanent or permanent fixture locations for electronics. In this way distal mass is moved more proximal, providing for a lower swung mass or weight (the experienced force from the mass) for the user.

Neural control of robotic prostheses by measuring surface electromyography (sEMG) of residual limb musculature has been widely researched in the field. Specifically, two major focuses have been extensively investigated: 1) how to process, interpret, and infer sEMG data to movement of residual limb in real-time, and 2) how to measure sEMG signal accurately with minimal form factor and energy consumption. By integrating a portable and real-time sEMG measurement system with a powered prosthetic actuator control system, it is possible to deliver a truly portable prosthesis with neural volitional control. For example, the sEMG system can be physically integrated with a special socket and liner built for prosthetic neural interface system. The prosthetic liner can have integrated electrodes, made by conductive fabric embedded into the silicone/urethane liner material. This construction provides robust electrical access to the muscle activation signals. Amplifier and filter electronics can be mounted to the socket, providing physical stability while allowing access to the liner electrical output interface. Neural input may be used to control the device dynamics through machine learning, pattern recognition, proportional control, or using more complex biomechanical models. By integrating portable and real-time sEMG measurement system to an active powered prosthetic system, it is possible to deliver a portable prosthesis with neural control.

The human gait cycle is divided into two distinct phases: stance, when the foot is in contact with the ground, and swing, when the foot is in free space. Stance occurs from 0% to roughly 62% of the gait cycle, from heel strike of the leading leg to toe off. Swing then occurs from roughly 62% to 100% of the gait cycle, from toe off to heel strike of the contralateral leg. During stance, the ankle-foot complex provides shock absorption (negative work) as well as propulsion (positive work). During early stance, the ankle plantar flexes, absorbing impact of heel strike and acting as a linear spring. During foot flat, the ankle dorsiflexes and stores energy, and then plantar flexes rapidly during late stance, generating mechanical energy. During swing, the ankle first dorsiflexes in order to increase clearance between the ground and the foot, and then assumes a foot posture in preparation for foot strike. In addition to sagittal plane motion, inversion and eversion of the subtalar joint is important for replicating biological gait. In particular, maneuverability during sidestepping is extremely dependent upon impedance modulation and force generation of the subtalar joint. In order to replicate biological gait for persons with amputation, prostheses should allow for active adjustment of ankle angle in the sagittal as well as frontal planes through both ankle and subtalar prosthetic joint movements.

Current ankle-foot prostheses fall into two main categories: passive and powered devices. Passive ankle-foot prostheses include conventional prostheses and energy-storing-and-returning (ESR) feet. Conventional prosthetic feet include the solid ankle cushioned heel (SACH) foot, which absorbs ground reaction force upon heel strike through a compressible heel wedge, and the Single-Axis foot, which allows the foot to plantar flex during early stance. These devices are not able to mimic ankle-foot biomechanics of persons with biological limbs, specifically they do not allow for ankle and subtalar joint motion during walking, and therefore do not replace full function of the amputated limb. Powered prostheses are better able to match biological gait, by providing the user with the ability to change ankle position throughout the gait cycle as well as by injecting power into the stride. However, powered prostheses require power sources and transmissions capable of generating biological levels of torque. Quasi-passive prostheses—devices that consume power to adjust swing-phase joint position and/or stance-phase mechanical impedance (stiffness/damping) but do not inject additional mechanical power into the gait cycle—provide many of the benefits of powered prostheses while utilizing lower mass and acoustic output via lower profile power supplies and torque generators.

Quasi-passive ankle-foot prostheses have been designed to adjust ankle angle during swing. The PROPRIO FOOT prosthesis (Ossur) automatically adjusts swing phase ankle angle based on sensor values read by an onboard microcontroller. This device automatically adapts to the terrain such as increasing ankle dorsiflexion angle during stair ascent. Another quasi-passive device detects shank orientation of the shank and ground contact using a plurality of sensors, and utilizes an onboard microcontroller to actively tune the dampening of the ankle during walking, to adjust to various ground surfaces. Sensors detect orientation of shank as well as ground contact. Another such device utilizes a non-backdrivable lead screw to drive the ankle through a cam, adjusting the ankle angle during the swing phase of walking. None of these existing quasi-passive ankle-foot prostheses adjust the set point of series elastic joint springs, nor adjust joint damping levels, under computer control based on speed or terrain. Further, none of these existing quasi-passive ankle-foot prostheses incorporate a second degree of freedom in order to replace subtalar joint function. Still further, no quasi-passive device exists that utilizes series elasticity in a low-power, low-mass package. Additionally, no device exists that incorporates volitional neural control of stance-phase joint spring equilibrium and damping across speed and terrain, as well as standing and sitting maneuvers, incorporating a non-backdrivable series-elastic actuator. Finally, no device exists that incorporates volitional neural control for continuous free-space position joint control, as well as stance phase impedance control, incorporating torque feedback from the prosthesis using functional electrical stimulation of residual limb musculature.

With the advent of powered lower limb prostheses, in recent years there has been considerable interest in developing suitable control algorithms facilitating efficient, comfortable, and biomimetic gait for people with lower limb amputations. In particular, a large body of work has focused on developing algorithms for the anticipation and adaptation to different walking terrains such as level ground, ramps, and stairs. Training procedures for developing these machine learning algorithms are often time consuming. For a given set of sensors and a powered prosthesis platform, studies involve logging data, often over multiple days, from multiple subjects traversing a given terrain. This is followed by manual offline terrain labeling and a pattern recognition analysis. For real-time control tasks, offline algorithms must then be translated into embedded languages, with no guarantee that the predictive models will perform as well as they did in simulation when subjected to new terrains, users, control methodologies, prosthesis platforms, or physiological conditions—it is impractical to include all such possible conditions in one training set.

Some attempts have been made to automate aspects of the machine learning process. One approached used an external system during data collection to automatically identify terrain with high accuracy and train a machine learning model online, without the overhead of offline labeling and analysis. However, the main drawback of this approach was the requirement for an external system for labeling, making re-training in alternate conditions burdensome and impractical. Another approach used an adaptive EMG-based machine learning model to compensate for EMG disturbances but this system did not include a method for labeling the terrain and thus did not directly optimize for prediction accuracy. Additionally, the part of the model employing intrinsic sensor signals was static.

The problem of non-generalized models and burdensome training routines can be addressed by developing a method to automatically and continuously train a pattern recognition algorithm using only the intrinsic sensors on-board a below-knee prosthesis. This model relies on an accurate back-estimation step, which uses a heuristic to label strides after they have been taken, and thus continually updates the predictor with new training data. The back-estimation step is enabled largely by a novel high range-of-motion (ROM) prosthesis which allows the use of ankle angle during stance to distinguish inclined terrains from level terrains. Currently, the only commercially available powered below-knee prosthesis, the EMPOWER prosthesis by Ottobock, has a limited 22-degree ROM with zero degrees of dorsiflexion, which is insufficient to span even the biological range of level-ground walking (10 degrees dorsiflexion to 18 degrees plantarflexion), let alone alternative terrains. Similarly, most powered prostheses in the research environment are designed to operate on level-ground. The novel mechanical system described here enables 115 degrees ROM, spanning the entire mean biological ROM and consequently allowing for significant biomechanical differentiation between ground terrains.

By employing an incremental learning algorithm leveraging the backward estimation of terrain labels and a high-ROM prosthesis, we achieve a field-usable automatic training method that requires no manual processing steps or external devices. This method would enable a powered prosthesis to automatically and efficiently update a customized terrain predictor that continuously converges on the optimal prediction accuracy for a given walking condition. Finally, while the method was developed on training data obtained from a transtibial prosthesis, the method is also applicable in the transfemoral case, and in the case of a lower limb exoskeleton.

Overview of Cantilever Beam SEA

Embodiments of the invention generally are directed to any actuator system that benefits from force control, energy storage for cyclical motions and high power motions in a low mass package by way of a deformable, cantilever beam, series elastic element and displacement generating prime mover. This system can be implemented for any robotic system that utilizes cyclical motions and benefits from a high power or energy density. Such systems include walking, flying or swimming robotic systems, industrial robotics, or prosthetics.

Actuator

In one embodiment, the invention is an actuator composed of a motor connected to a screw reduction that converts rotary to linear motion that then drives an output motion relative to a base frame, and where the resultant reaction force, felt at the motor from driving the output, is grounded to the frame through a moment arm attached to one or more elastic members grounded to the frame. The elastic member is deformed primarily in bending by the reaction force applied to a moment arm that applies the linear force at a distance to the elastic beam such that it creates a coupling moment on the elastic beam. The elastic member operates in a cantilever configuration and is grounded to the frame. A prior moment arm coupled actuator is described in Knabe et al., 2014 and Orekhov, 2014 (C. Knabe, B. Lee, V. Orekhov, and D. Hong, "Design of a Compact, Lightweight, Electromechanical Linear Series Elastic Actuator," in ASME. International Design Engineering Technical Conferences and Computers and Information in Engineering Conference, Volume 5B: 38th Mechanisms and Robotics Conference, 2014, pp. 1-8; V. L. Orekhov, "Series Elasticity in Linearly Actuated Humanoids Series Elasticity in Linearly Actuated Humanoids," Virginia Tech, 2014). The current system, however, improves over the prior approach because it further simplifies the design by removing one of the degrees of freedom at each of the ends of the linear actuator, as well as removing the belt drive assembly and instead integrating the screw into the motor design, such that the rotation of the motor is directly coupled to the nut that drives the screw. Where the referenced design utilized universal joints with two degrees of freedom at each pivot location to transmit load, embodiments of the invention described herein utilizes a single pivot at each end while exploiting the flexural nature of the moment arm and spring to accommodate any misalignment. These design features simplify the system architecture while also reducing sprung mass, improving the operating performance of the actuator.

Suitable materials for the cantilever beam spring include steel, composites, and plastics. Polymers such as nylon or polyurethanes perform well, though their internal viscoelastic damping results in hysteresis and their strain-rate dependent modulus of elasticity may not favorable. Non-isotropic materials such as composites can be tuned to maximize mass utilization with fiber alignment when stress orientation is considered along with geometric conditions. In a particular example, the spring is a unidirectional E-glass fiberglass composite (GC-67-UCB) manufactured by Gordon Composites.

An embodiment of this invention is a device that has a motor directly connected to a screw reduction operating in a rotary nut configuration where the motor rotates the nut causing linear motion of the screw. Where in previous applications a motor transmits torque to a nut by way of a belt that drives a screw, in this approach, the motor screw nut is built directly into the motor rotor, such that no belt is required. This can be done either by attaching a screw to the motor shaft, or as shown in FIGS. 1-9, 18A-19C, building the nut into the rotor of the motor and allowing the screw to pass back and forth through the center of the motor as the combined rotor and nut rotate as to generate the linear motion of the screw. The reaction force of the motor due to the torque it generates on the nut and the axial force hence applied to the screw is directed to a supporting elastic member by way of a moment arm attached to the motor support, inducing a coupling moment to the elastic cantilever beam that has one end grounded to the frame.

In another embodiment, the device has a motor directly connected to a screw reduction operating in a rotary nut configuration where the motor rotates the nut causing linear motion of the screw, the output of which passes the force through an elastic cantilever beam such that it moves relative to the frame, and the motor is grounded directly to the frame.

In yet another embodiment, the device has a motor that passes force through a reduction ratio to an output, one end of which is grounded the other applies a force to cause an elastic cantilever beam to bend. The bending beam effective length can be changed by moving an intermediate support some distance between the grounded end and the applied load end, changing the effective stiffness of the beam and the overall stiffness and bandwidth of the actuator.

The moment coupled series elastic actuator provides the capability of energy efficient, torque controlled output of a rotary joint by maximizing the strain energy utilization of a spring element in series with a linear displacement actuation mechanism. Defined as a moment-coupled, reaction force, series elastic actuator, this actuator topology consists of a cantilever beam spring, on one end structurally grounded to the frame, whereas the other end of the spring is subject to the reaction force of a linear actuator, the vector of which is applied at a distance from the spring neutral axis and is generally axially aligned and offset from the neutral axis of the spring. The offset is enforced by a structural element that provides a moment couple at one end of the spring. Analytic analysis of a beam in bending from a coupled moment has uniform and constant strain along its length, maximizing material utilization for strain.

The linear force is due to the reaction force of a linear actuator tied to the output joint. A ballnut mounted directly inside a brushless, direct current motor converts the rotary motion of the motor rotor to the linear motion of a ballscrew. This linear motion generates axial displacement and force, that couples to the spring through the nut, motor, and motor support on one end. Rotary motion at the actuator output is due to the axial offset of the linear actuator from the output frame pivot.

Torque control is possible with high fidelity joint torque measurements and a closed-loop feedback electronic controller. In this system joint torque is measured by applied offset force and is measured either: with an attached axial load cell, or spring deflection is measured as the difference in measured displacement of the rotary output joint and the motor displacement along the length of the screw, or directly by deflection of the spring.

Spring stiffness requires system performance compromise in series elastic actuators. Large spring deflections allow greater force measurement fidelity with lower precision displacement measurement device requirements, increased energy storage, and impedance decoupling between drivetrain and output. Lower stiffness springs, also, however, reduce system bandwidth at large torques by requiring the motor to rapidly accelerate and get out of its own way in fully reversed loading with the associated larger displacements of low-stiffness springs. Higher stiffness springs enable higher force or torque capability, at the tradeoff of reduced energy storage. The stiffness of a spring in bending can be adjusted by several parameters, such as height, width, and length. The most readily available parameter to adjust on the fly is the sprung length.

An actuator configuration with a variable stiffness spring allows continuous adjustment of system performance. In cyclic operating conditions, such as gait motion, there are phases of the trajectory that pass through zero displacement of the spring. At these points minimal force is required to adjust the sprung length of the spring. Two rollers mounted on opposing sides of the spring and restricted to move along the length of the spring by a set of rails provides a means to constrain the sprung length of the actuator. This system can be motivated by a secondary linear actuator system composed of a lead screw, ballscrew, or other linear motion system such as belt or cable drive.

The system is controlled by an embedded electronic control system that reads the sensor inputs, makes decisions, and generates signals to define motor trajectories. Closed-loop feedback is performed computationally within the micro-processor be evaluating measured output to desired output.

Socket Mount

In the application of prosthetic devices or other mobile systems a local energy source is required to supply the necessary electrical energy to drive the motors. A battery such as a lithium polymer pack is generally of substantial mass in comparison to the full system mass and is designed to be an onboard component of any powered prosthetic device. The majority of amputees utilize a rigid socket for interfacing their body with their prosthetic devices. To maximize comfort and performance for users the battery is affixed to the socket, rather than onboard the actuator system. The more distal a mass placement the greater the energy required to move it about an axis, so from a user energetics perspective, proximal mass is preferred.

Similarly, any number of the other electronics may also be mounted to the socket, rather than onboard the prosthetic device, as a mean of augmenting and expanding the capability of device as a prosthetic control system. Numerous means of mounting the battery and wiring to the socket are possible. A battery pack can be attached to an unmodified socket by means of a strap, hook and loop (e.g. Velcro), or adhesive. Neural interface electronics for direct volitional control can also be mounted. The socket can be configured with fastening and mounting hardware that ranges from fully integrated battery pocket, to locating features to constrain or align a battery pack and associated wires, or simple alignment features.

Features of the Cantilever Beam SEA include:
a) Actuator
  i. Moment coupled spring SEA
    1) Moment couple maximize strain distribution energy in material
    2) Discrete material spring
    3) Single material spring/actuator (cnc, additive)
    4) Linear motion to rotary motion integrated in motor
      a) Nut integrated into motor
      b) Thrust supporting bearings in motor
    5) Reduced components
    6) Force sensing with load cell
    7) Force sensing with difference between joint encoder and actuator encoder
    8) Variable stiffness actuator
    9) Backdriveable high efficiency version
    10) non-backdriveable low power, lightweight version
  ii. Screw drive integrated into motor design
  iii. Single pivot motor mount
  iv. General to robotics
  v. Specific to prosthetics
    1) Ankle
    2) Knee
    3) Ankle and knee system
    4) Elbow, or other joints b) Socket Mount (battery, electronics)
  i. Attachment on the socket
  ii. Separable attachment
  iii. Features on the socket for attachment
  iv. Battery on socket
  v. Embedded systems on socket Details of Cantilever Beam SEA The actuator shown in FIGS. 1-10 is a moment coupled, cantilever beam, series elastic actuator (MCB-SEA). It is fundamentally composed of a displacement mechanism that applies a moment to a cantilever beam while applying torque about an output axis. The displacement mechanism is a mechanical transformer that converts rotary motion into linear motion by way of rotating a nut about a non-rotating screw. The nut is rigidly integrated into the rotor of a direct current motor, such that rotation of the motor rotor causes a screw to move linearly, the distance traveled being related directly to the lead of the screw. The lead of a screw is the linear travel for a single rotation. The lead of the screw affects the overall actuator transmission or gear ratio. The linear motion of the screw is tied to the output by a pivot located some distance from the rotational pivot of the output axis. The reaction force of the screw passes through the nut, through the motor bearings, to the motor housing, and to the motor support structure. This motor support structure consists of a pivot that attaches the motor housing to a moment arm. The moment arm is a structure that affixes the housing at some distance away from a cantilevered beam that acts as a spring. The linear motion of the screw is generally, though not always entirely, parallel to the spring. In this way the force generated by the screw is offset from the neutral axis of the cantilever beam, generating a moment about the end of the spring. The spring is used for multiple purposes: impact resistance, force measurement, and energy storage. Deformation of the spring dissipates impact loads at the output, and also allows a means to measure force. Deformation of the spring also provides energy storage for the application of energy efficiency and power density. The energy required to deform or strain a material can be restored if the strain levels remain within the elastic regime of the material. A cantilevered beam with an applied moment on an end has a constant moment across its entire length, meaning all of the sprung length is fully utilized to store strain energy. The fixed end of the spring is grounded to the frame that the output pivot rotates about.

Figure 2C:
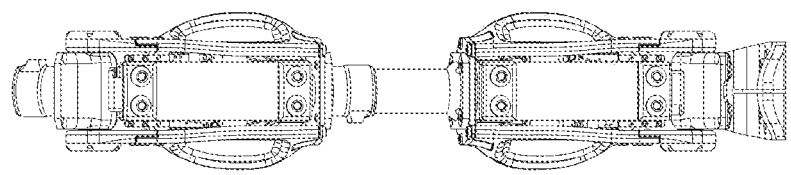
FIGS. 2A, 2B, and 2C are back, side, and front views, respectively, of the two actuators of FIG. 1 used as a transfemoral prosthesis.
Figure 2B:
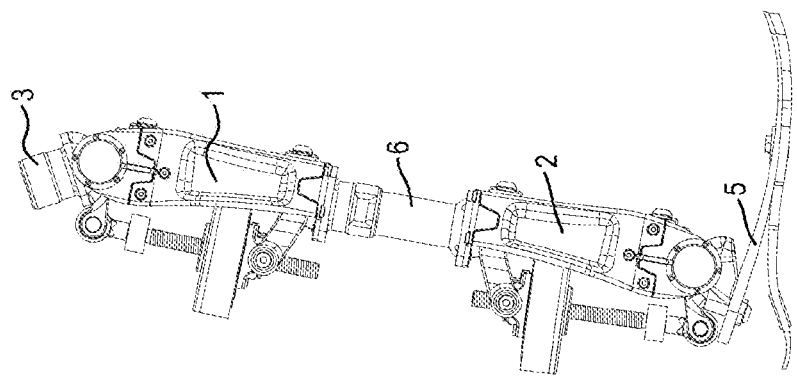
Figure 2A:
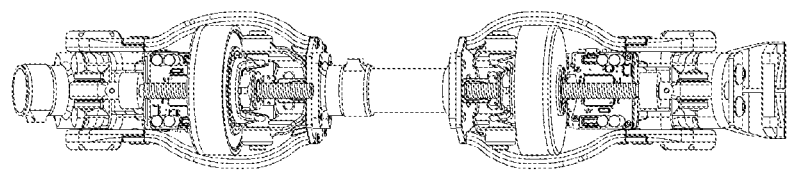

FIGS. 1 and 2A-2C show the same actuator utilized as both an ankle 2 and knee 1 configurations connected by a standard prosthetic pylon 6 to form a leg device 4 outfitted with a standard pylon attachment 3. The actuator can be used in any configuration that requires force or torque control about a joint. The actuator system in FIG. 1 can be used for any humanoid configuration as a robotic leg. FIG. 2A shows a knee 1 and ankle 2 system for use as a prosthetic device for an above knee amputee. A single actuator can also be utilized for an above or below knee amputee with a single powered degree of freedom.

Figure 3A:
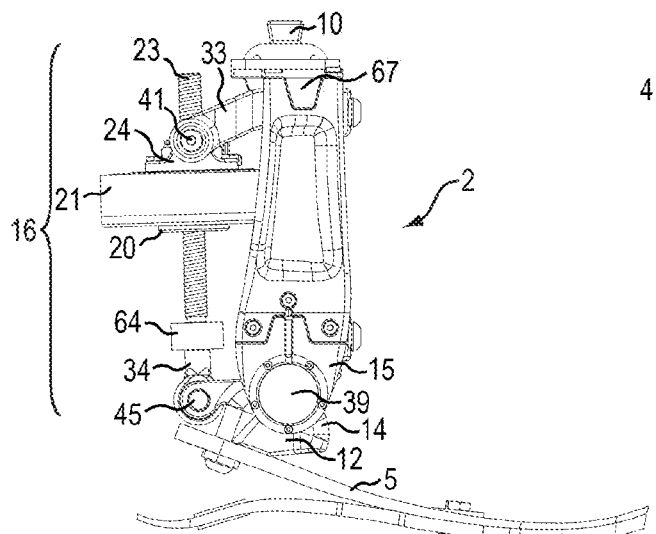
FIGS. 3A and 3B are side and isometric views of the MCB-SEA system configured as an ankle device.
Figure 3B:
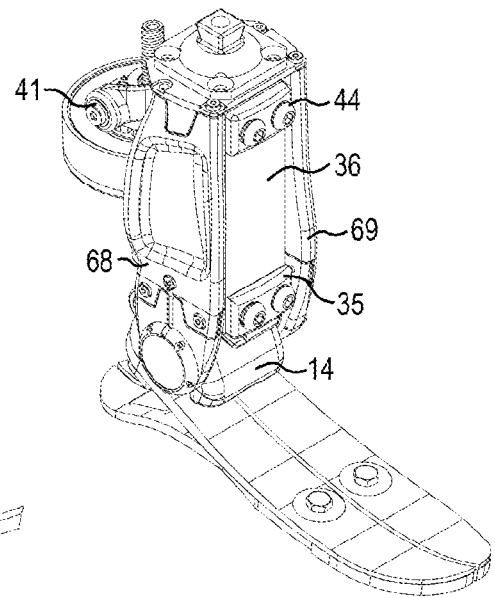

FIGS. 3A and 3B show the actuator configured as a robotic ankle 2 where a standard off-the-shelf prosthetic flex foot 5 has been attached to the output arm. The foot 5 attaches to the output arm 14 of the actuator by way of an adapter component 12 that places the rotary pivot axis of the ankle at a biologically appropriate orientation with respect to the toe and heel of the foot 5. The rotary output arm 14 rotates about the frame or bearing yoke 15. FIG. 8B shows the joint orientation is measured by a rotary encoder 40 and associated magnet 46 mounted in the axle 37 attached to the rotary output arm 14. The axles 37 seat in bearings 43. The encoder circuit board is held in place by bearing cap 38 and protected with a cover 39. Side support arms 68 and 69 attach to the frame 15 and route structural loads down to a baseplate 67 that is used to attached to standard prosthetic attachment components 10 such as shown in FIGS. 3A-3B.

Figure 4A:
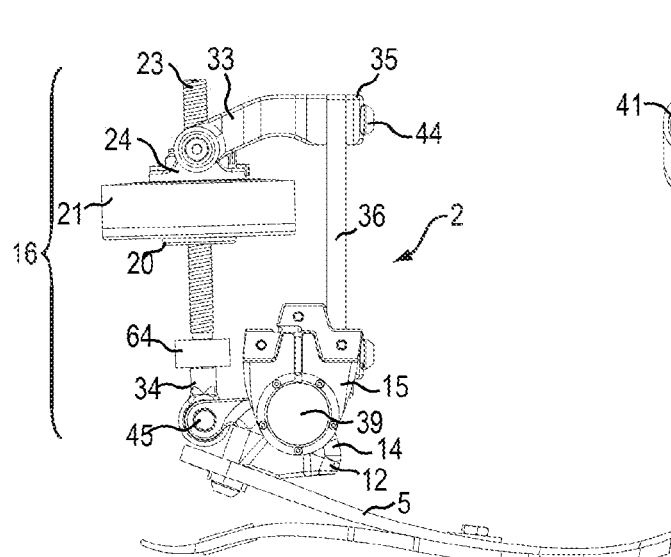
FIGS. 4A and 4B are side and isometric views of components of the actuator, shown with an off-the-shelf prosthetic flex foot combined into an ankle configuration.
Figure 4B:
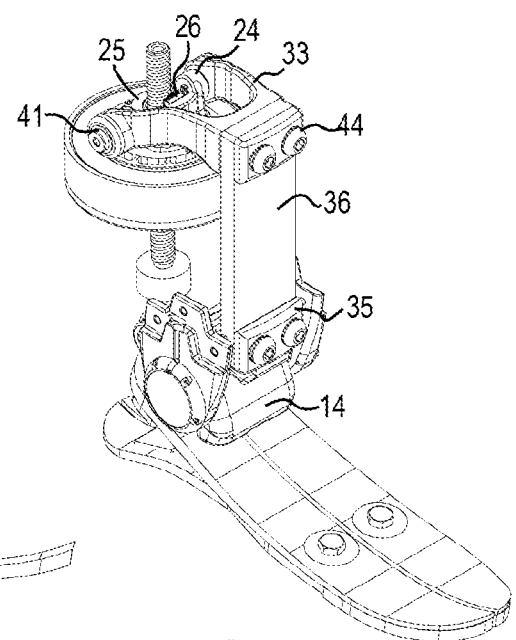

FIGS. 4A-4B show the actuator configured as a robotic ankle in a minimum functional configuration in side view FIG. 4A and isometric view FIG. 4B. The structural side components 67, 68, 69 are not shown as they are in FIG. 3A because they are not crucial to the operation of the system, rather they are specific to the shown configuration as a prosthetic joint. It is also possible to build the actuator with frame component extended to connect to other components as necessary. The main mechanical operational components of the actuator are visible in FIGS. 4A-4B. The grounding frame 15 is the component that all other motions are made with reference to. The output arm 14 pivots about an axis that aligns with the bearings 43 (FIG. 8B) in this frame. A connector assembly 16, including screw 23, connect the output arm 14 to a moment arm 33. The screw 23 is attached to a rod end 34 that has a pivot 45 placed some distance offset from the output rotational axle axis such that linear motion of the screw is transformed into rotary motion about the frame 15. The screw 23 passes through the motor. A nut 32 shown in FIGS. 5A and 7B matched to the screw is rigidly attached to motor 21 rotor 18. A presser flange 20 helps axially secure the nut 32 with respect to the motor rotor 18. The motor stator 17 housing is grounded to the moment arm 33 through a support pivot 24. The moment arm 33 transfers the axial load of the screw to the cantilever beam spring 36 by way of attachment with clamp 35 and screws 44 such that a moment couple is generated at the point of attachment on the spring. The spring 36 is itself then grounded to the main frame by way of clamp 35 and screws 44, again such that a moment may be coupled to the spring. In other embodiments the spring may be integrated into the structure such that the frame 15 extends around as both the spring and moment arm, such that clamps are not required and the frame is also acting as the spring component.

Thus, there is provided a prosthetic device that includes a frame 15 defining an output axis, a cantilever beam spring 36 having a first end attached to the frame and a second end, and a moment arm 33 attached to the second end of the spring. A rigid output arm 14 is coupled to the frame and rotatable about the output axis. A connector assembly 16 connects the moment arm to the output arm. The connector assembly is coupled to the moment arm by a moment pivot 41 and coupled to the output arm by an output pivot 45 located at a distance from the output axis. The connector assembly is configured to apply a moment to the cantilever beam spring via the moment arm while applying a torque about the output axis via the output arm.

FIG. 5A is a cutaway view showing detail of the majority of the components of the system. In this embodiment the actuator frame 15 and separate side supports 67, 68, 69 are shown. The output arm pivots about an axle 37 axis supported by the frame. A pivot 45 some distance from the output axis is where the screw 23 attaches to the output arm. A pushrod 34 is freely rotatable about the axis of this pivot 45 via bearing 42 and allows the screw to apply axial forces only. Those forces act in both tension and compression. In this embodiment an axial load cell 64 is placed to directly measure the axial forces being applied to and from the screw. The axial force could also be determined by measuring strain of the spring, or by evaluating the difference between expected motor orientation due to joint orientation and the measured motor orientation also determines deformation of the spring and hence force at the screw and hence joint torque. The matched nut 32 of the screw is affixed to the rotor 18 of the motor 21. The motor in this embodiment is an "outrunner", or a brushless dc-motor with magnets that rotate externally about the stator. Alternative designs with internally rotating rotor could also be utilized. The rotor is supported by a pair of rolling contact bearings 22, in this case angular contact bearings are utilized in a back to back configuration. The bearings pass the axial load applied to the rotor to the motor housing 17. The motor housing transmits both the screw axial load and reaction torque due the torque generated by the motor to a motor support component 24 (visible in FIGS. 3A-4B, and FIGS. 6A-7C). The motor support transmits force to the moment arm through a pivot 41 supported in bearings 49 in moment arm 33, shown in FIG. 8C. The pivot on either end of the screw and motor are necessary to allow for changing orientation of the screw as the output rotates about the frame and the loaded portion of the screw changes length. The motor support 24 component also transmits the reaction torque of the motor to the moment arm 33. The moment arm then couples these loads to the spring 36 by being clamped by screws 44 fixing a clamp component 35 for distributing force to the spring. The spring then grounds these loads back to the actuator frame 15. FIGS. 6B-6C show how the spring deflects and screw loaded length changes with applied external load. FIG. 5A shows angle hard stop 65 and spring deflection stops 66, 67. The spring deflection hard stop 67 and bumper 66 limit maximum deflection of the spring. Component 65 is an output angle hard stop that limits the maximum ranges of motion of the rotary output. This prevents components from over extending into neighboring components, such as the screw or spring colliding with the electronics 57, 58 shown packaged within the structural frame in this embodiment.

FIG. 7A is a close-up, isolated view of the integrated motor and pass-through screw system. In this embodiment, a brushless dc motor 21 with outside rotor is utilized. The design of the rotor is such that the magnets are affixed to the inner portion of a rotating component. This rotor component has a nut 32 integrated with it. The nut could be directly integrated into the design of the rotor, however in this configuration it is a separate component that is separately affixed to the rotor by means of a presser flange 20 and a keyway to help transmit force. The rotor also is supported on one or more rolling element bearings 22. These bearings support the radial loads due to the motor magnetics and nut reaction forces, as well as the thrust loads due to the axial forces passed between nut and screw. The bearings are then themselves supported in the motor stator 17, also referred to as the motor housing. The bearing system in this embodiment benefit from an axial preload to remove any play in the system, this is provided by a presser flange 19 that threads onto the rotor, preloading and affixing the bearings axially. On this presser flange is mounted, via an encoder holder 31, an off-axis angular encoder disk 25, and a reader head 26 is attached to support 24 for measuring motor orientation. The motor housing is then grounded to the next component in the load path by a support structure 24. This structure has a pivot axle 41 shown in FIG. 8C that transmits the axial force and reaction torques to the moment arm 33.

The moment arm 33 is designed in such a way that it can accommodate manufacturing tolerance variations in pivot alignment, support structure and spring misalignments. The design feature of the moment arm that enables manufacturing tolerance is that it is designed narrowly in the horizontal direction shown in the cross-sectional section G in FIG. 8B, yet designed thickly in the direction aligned with the section G line. This detail also visible in FIG. 4B allows for some flexure in the moment arms while transmitting the screw axis loads to the spring.

FIG. 6A shows a realized actuator with side supports removed, showing the actuator is fully functional without side plates. The side plates are for transferring load to the main robotic or prosthetic structural frame, as geometry requires, and can be designed specific to the application or even integrated into the frame 15. The main components of this actuator are load path from frame 15 to pivot arm 14, to the screw 23, through the motor 21, moment arm 33 and finally through the spring 36 and back to the frame 15. FIG. 6B shows the behavior of the actuator when a clockwise load is experienced at the pivot arm 14. If the motor is held stationary and the pivot is allowed to rotate, then the spring 36 bends counter clockwise to support the counter clockwise external torque. If the actuator is operating in a torque control mode, then the output arm 14 remains stationary and the motor rotates, extending the screw to counteract the external load and the reaction force passed through the motor due to screw fighting the external load causes the spring to deflect. In similar behavior, to support an externally applied clockwise torque at the output, as shown in FIG. 6C, the motor rotation causes the nut to pull the screw downward, bending the spring towards the motor. Again in a torque controlled operation where the output arm 14 remains stationary due to balanced external load and internally generated load from the actuator the loaded portion of the screw shortens as the motor climbs up the screw, bending the cantilever beam spring 36 towards the motor. As a torque is applied about the output pivot 14 the output remains stationary while the motor rotates and either extends or retracts the screw as is necessary to counteract the load torque. With the output fixed the change in loaded length of the screw is transformed into deflection of the spring. In order to support an externally applied clockwise torque, the screw must extend. Since the screw cannot extend due to this applied external load, instead the reaction force is passed through the motor, moment arm, and causes the spring to flex outward, towards the left of the image. The deflection of the spring is directly related to the angle of the output arm, the orientation of the screw, and the force applied by the screw. Similarly, this force in the screw can also be directly related to the torque in the motor.

Figure 9:
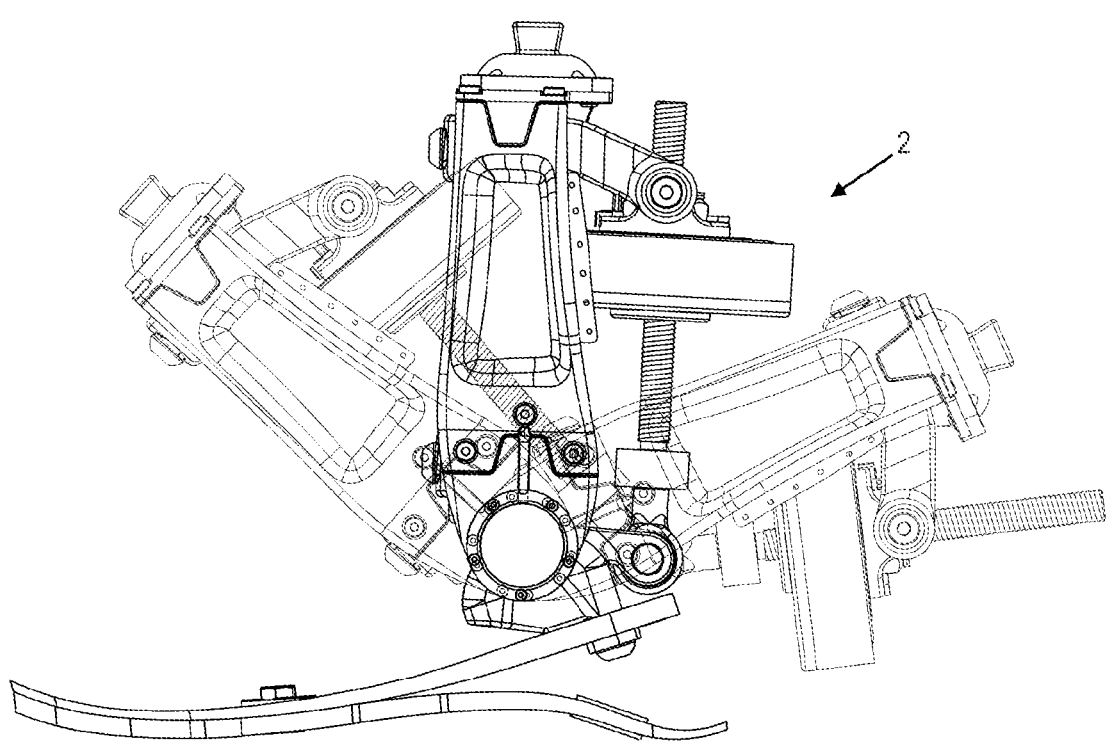
FIG. 9 illustrates range of motion of an embodiment of the actuator of FIG. 2A.
Figure 10:
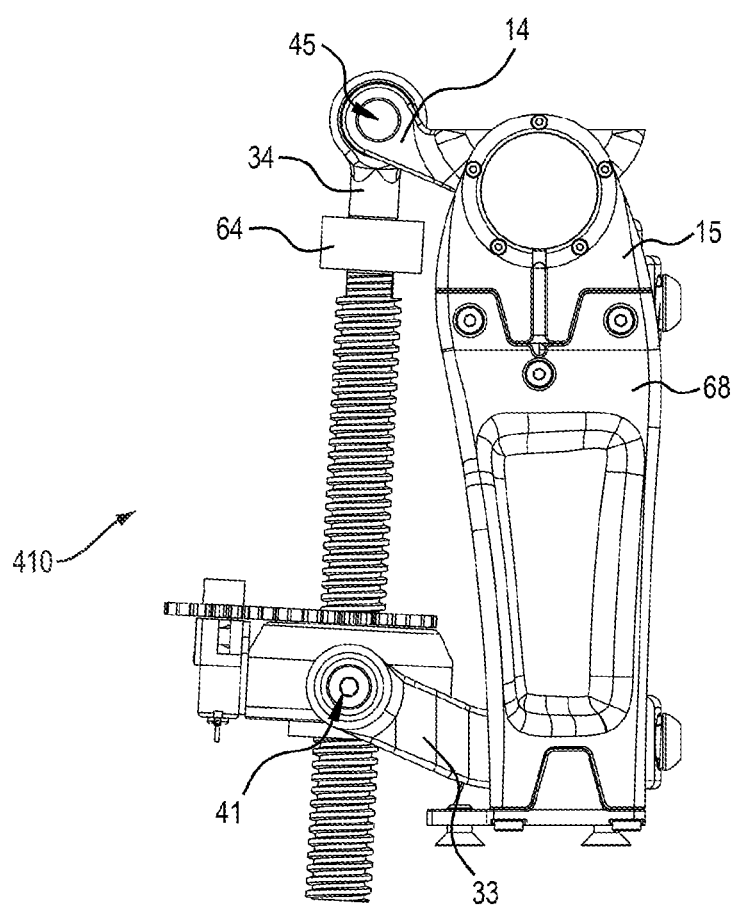
FIG. 10 illustrates a MCB-SEA actuator with a non-backdriveable rotary to linear transformer.

FIG. 9 shows the ankle-foot prosthesis 2 with its large 115-degree total range of motion with 35 degrees of dorsiflexion.

FIGS. 10 and 11A-11C illustrate a non-backdrivable linear transformer 410, which is similar to that shown in FIGS. 7A-7C, and designed to work within actuators shown in FIGS. 3A-6C. The non-backdrivable actuator can be manually adjusted to set the free-length of the spring and joint orientation, or can be driven by a motor. The linear actuator uses a low-efficiency lead-screw 409 such that friction cannot be overcome during normal operation, locking its position as seen from the output (joint load). The rotary nut 400 can be manually rotated by a user to adjust joint angle position for comfort. If a motor 401 is used in combination with the nut 400, the actuator can act as a quasi-passive prosthetic or robotic joint. The motor can adjust the position of the screw (distance between pivot 45 of rotary output arm 14 and mounting pivot 41 of moment arm 33) during the unloaded or swing phase setting the joint angle. This allows for low-power consumption during stance. During stance the actuator acts as a passive joint. During swing the actuator joint position can be modified by user or by motor. The motor 401 is statically fixed or attached to nut housing 406. The motor rotor is attached to a drive unit, gear, pulley, or a friction pinion 411, as illustrated here, that is meshed with a similar meshing power transmission device, here gear 408. This gear 408 is either affixed directly to the leadscrew nut 400 or by a secondary adapter element 403, as shown in FIG. 11B. The nut assembly can rotate relative to the housing 406. In this embodiment, the nut assembly is shown supported by plain bushings 404 and 405 that reduce friction to rotation. The rotating assemblies are located in the housing 406 by a clamping plate 407. This full assembly, the linear actuator shown in FIG. 10 can be mounted into the actuator devices shown in FIGS. 3A-6C just as the backdrivable power mechanism shown in FIGS. 7A-7C can also be used. This allows either a high power, high efficiency linear drive mechanism or a low power, low efficiency linear drive mechanism can be used with the same structural hardware. The load cell 64 and joint encoders 40 can be used with both or either device. Similarly, this non-backdrivable lead screw combination can be used with a motor built into the housing as is shown in FIGS. 7A-7C without modification other than geometric changes necessary to fit the specific screw and nut geometries.

Electronic control modules (also referred to as embedded systems) modulate the torque generated by the motor. While not necessarily embedded in the actuator, FIG. 5A shows an embodiment where the electronic control modules 58 are embedded within the mechanical package of the actuator. The electronic controllers convert data from the angle or strain sensors either mounted on the spring or in the load cell 64, or the difference in joint and motor orientation to determine force at the screw and combines it with control algorithms to determine necessary behavior of the motor such that a desired output torque or joint orientation is achieved. The motor 21 used in this embodiment requires monitoring of its rotational position in order to correctly commutate the three electrical phases that generate torque. The orientation of the motor is monitored by an encoder 25 and 26. In this embodiment an off-axis rotary encoder is used where a metered disk 25 is encoded with orientation markings and a reader head 26 is mounted such that it can measure the markings and output a rotary position that can be read by the electronic controllers in the electronics package 58. The electronics package contains a motor drive unit as well as an actuator control system that monitors the sensors and commands the motor driver to control the motor as necessary.

Figure 16:
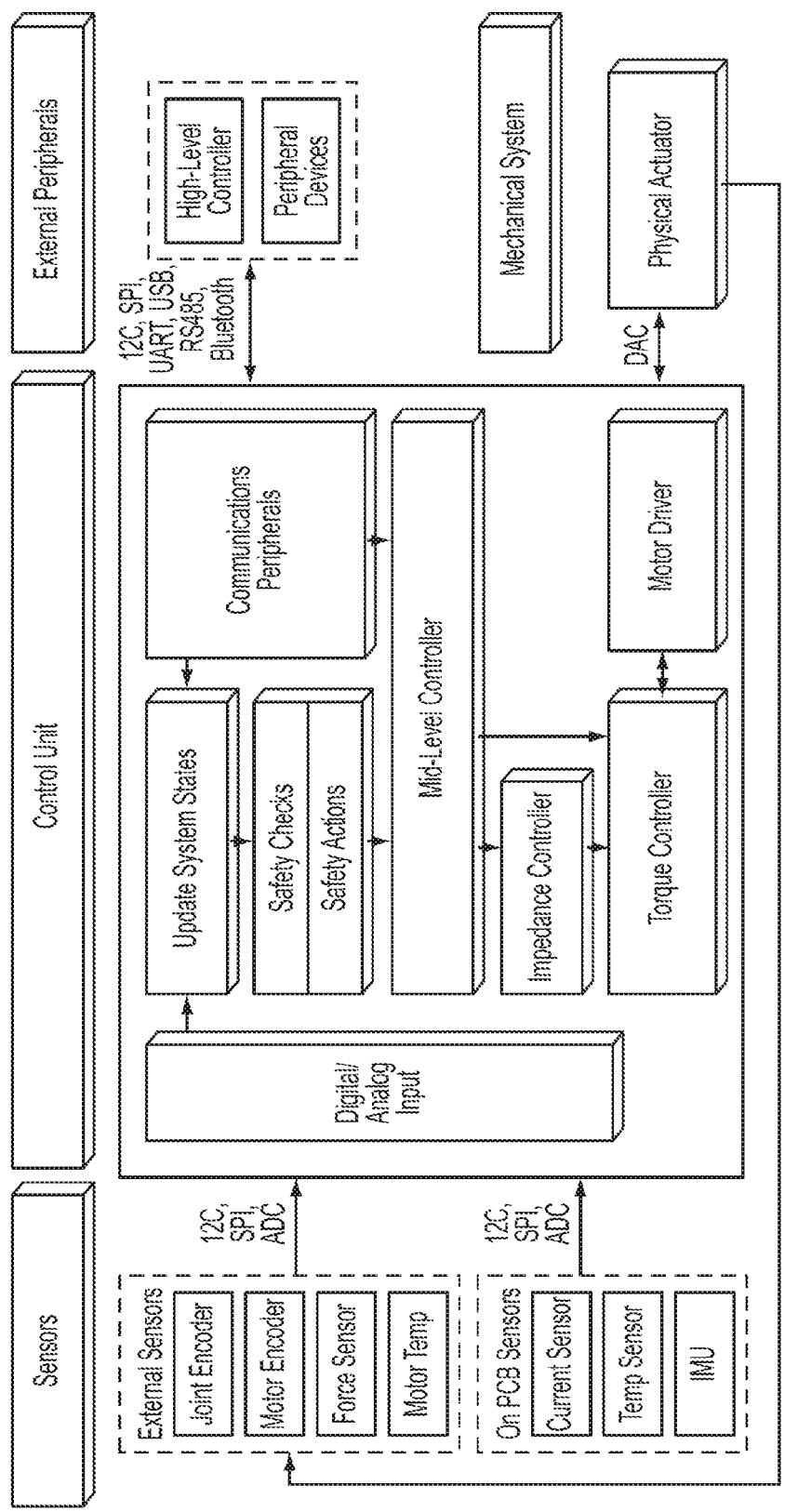
FIG. 16 shows the architecture of the actuator system according to an example embodiment.

The overall system architecture is shown in FIG. 16. A control unit resides on the embedded system electronics 58. The electronics 58 include a motor driver that directly drives current to the motor phases, as well as a central processing unit (CPU) that determines how to control the motor based on sensor feedback and either an internal mid-level controller, or control parameters received from an external high-level or supervisory controller. An external device can provide the control commands via the communications peripheral block that receives signals by a variety of standard communication protocols such as I2C, SPI, RS485, UART, USB, Bluetooth, CAN, etc. External peripherals may include off-board computers or micro-controllers, or other devices such as inertial measurement units (IMU) or EMG, or any number of systems capable of communicating across a standard micro-controller communications bus. If no external controller is in use then then the on-board mid-level controller operates as the high-level controller. Sensors for joint orientation 40, motor orientation 26, force at the screw, temperatures and actuator orientation are processed by the CPU. The data is converted into necessary information about the state of the actuator. A set of safety checks on actuator state are performed to verify the system is within safe operational conditions. If there is an out of safe parameter state identified a safety flag is generated and action is taken as necessary to attempt to bring the system into a safe state. Potential unsafe conditions are over current at the motor, joint angle, velocity or system temperatures (motor temperature or circuit board temperature). Potential recovery operations include reducing desired torque, commanded current, change in control state, etc.

Figure 18A:
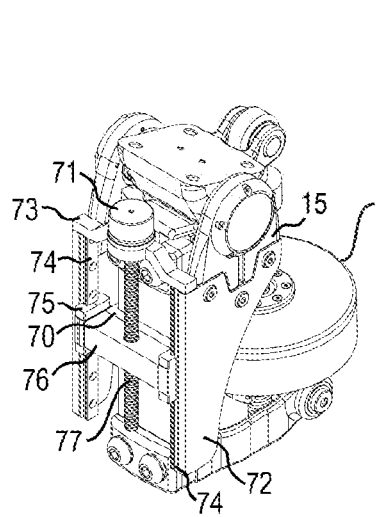
FIGS. 18A, 18B, and 18C are perspective, front, and sectional views, respectively, of a variable stiffness actuator.
Figure 18B:
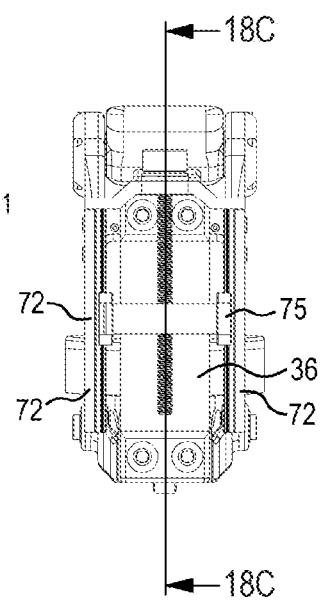
Figure 18C:
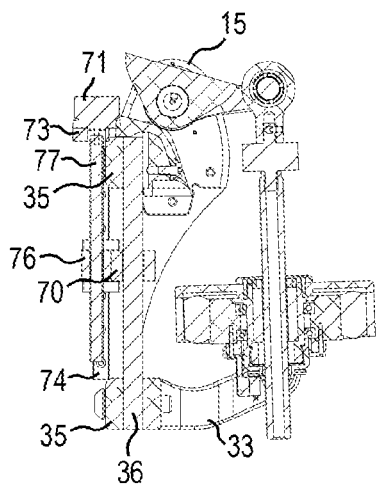

For high speed, high force applications large spring deflections are not beneficial because the motor must rapidly change direction and travel a long distance along the screw in order to reverse the direction of applied force. In these high frequency operating conditions, such as a running robotic or prosthetic system, a stiffer spring can be desirable. Similarly, in low frequency conditions, such as walking, large spring deformation is desirable as it allows more energy storage and release of energy from the spring—allowing for less electrical energy to be used to generate work at the actuator output. A variable stiffness mechanism can be built into the actuator to allow a single spring to be used, but its stiffness can be dynamically adjusted by changing the free length of the spring, shown in FIGS. 18A-18C. While each end of the spring remains grounded to each the moment arm 33 and frame 15, in this embodiment with clamps 35, an additional structural pivot 70 exists whose distance from the frame-grounded end of the spring can be dynamically adjusted. The pivot is structurally sound because it is supported by linear guideways 75 that ride along linear rails 74 rigidly affixed to side supports 72 that are mechanically grounded to frame 15. In this embodiment side supports 72 are separate components from frame 15, but they could also be integrated into the frame structure, as well as be integrated into the structure of side supports 68 and 69 from FIGS. 3A, 5A, and 8A. The pivot carriage 70 moves along rails 74 when driven by a linear motion system. In the embodiment shown in FIGS. 18A-18C another screw actuator is shown to provide linear positioning. This system is composed of a drive motor 71, supported by a frame 73 that is attached to the side supports 72, the motor shaft is attached to a screw 77 which then has a matched nut 76 attached or integrated with the pivot feature 70. Depending on the type of motor an additional encoder may be necessary to measure the position of the pivot. This can be a rotary encoder mounted on the shaft, or a linear encoder measuring position along the pivot. Rotation of the motor 71 causes the screw 77 to rotate which then drives the nut 76 to move linearly along the rails 74. FIG. 18C shows a section view of the variable stiffness components as well as the rest of the actuator.

For cyclical motion, which this actuator is particularly suited, there is a point in the trajectory when the force reverses direction and the spring bends through its neutral position. FIGS. 6A and 18C show the spring in a neutral position. When the spring is at this location there is no side load on the pivot and its distance from the frame can be adjusted with minimal energy expenditure. Though the time at this position may be short during high speed operation, because it is an instant of low spring deflection and hence low force on the pivot, rapid motions of the pivot can be made. For gait motions during the swing phase there is relatively low force in the actuator and ample time to make adjustment to the position of the spring pivot.

It is also possible to have manual adjustment of the free sprung length of the spring by instead of having a motor 71 at the end of the screw 77, a manual turn knob can instead be utilized at the same location as 71. This allows for a manually adjustable spring in the event a user wishes to change the spring stiffness for differing activities—for instance transitioning from walking into a jogging mode.

Figures 19A, 19B, 19C:
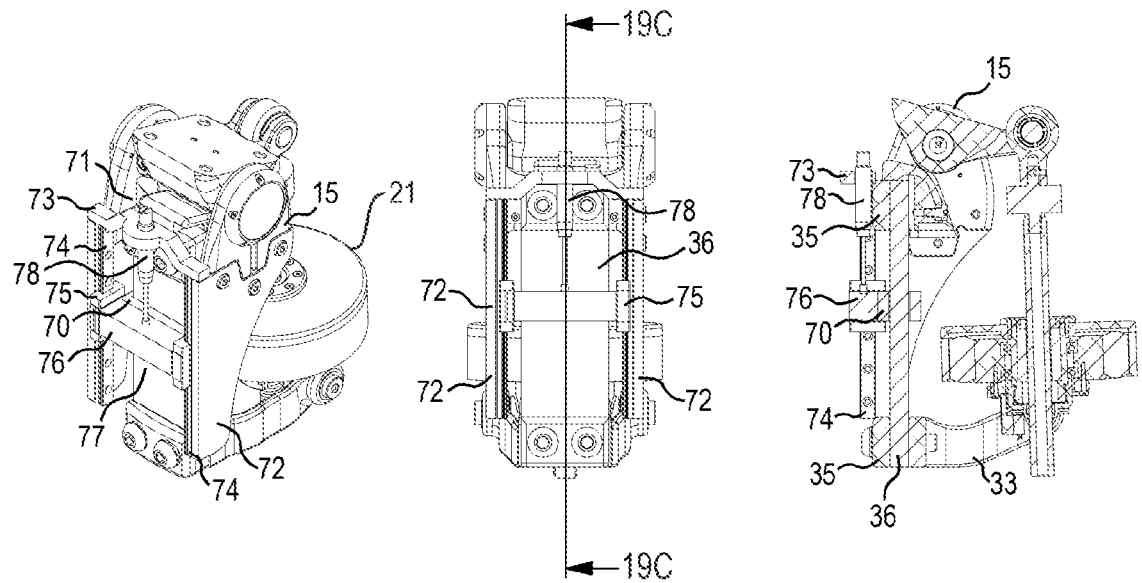
FIGS. 19A-19C illustrate a passive variable stiffness actuator.
Figure 19D:
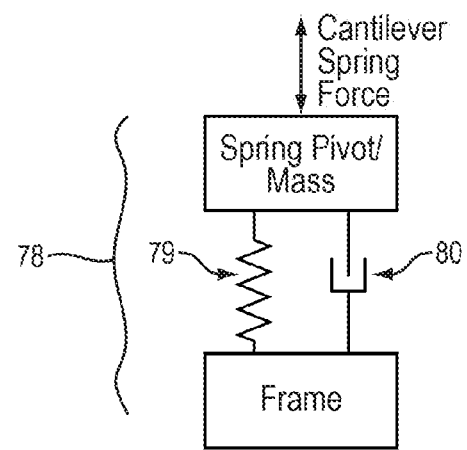
FIG. 19D shows a model of the actuator of FIG. 19A.

Instead of a manually or electrically driving the moving pivot, the location of the pivot can also be adjusted passively with a spring and damper which operates as a shock-absorber system shown in FIGS. 19A-19C. The shock-absorber 78 system operates as a low-pass filter for vibration. At high frequency or high speed operation the damper which has velocity dependent motion, resists motion. At low frequency or low speed the damper allows motion to pass and the spring dominates behavior. By tuning the shock-absorber spring and damper parameters the functionality or response of the position of the pivot 70 can be set to necessary operating conditions. Shown schematically in FIG. 19D, a spring 79 and damper 80 operate on a mass or in this case the pivot assembly 78. For example, the pivot can be tuned such that the shock-absorber spring holds the pivot at a resting or equilibrium position some set distance from the frame grounded end of the cantilever spring 36. As the spring 36 bends slowly, it pushes against the pivot 70, applying some force in the direction of motion of the pivot, the damper is minimally active and the shock-absorber spring is depressed. As the spring 36 bends rapidly, it pushes against the pivot 70, applying some force in the direction of motion of the pivot, the force from the damper is dominant and the pivot either remains in position or is depressed minimally, dependent on the damping ratio set in the damper. As such the position of the cantilever beam 36 pivot 78 can be self-adjusted as a passive system simply by tuning the characteristics of the spring and damper that make up the shock-absorber system 78 in FIG. 19A-D.

Thus, as described above, the beam spring 36 of the device can be configured as a variable stiffness beam spring. For example, as illustrated in FIGS. 18A-18C, the device can include a carriage 70 and a rotatable beam screw 77 that extends parallel to the beam spring and engages a nut 76 coupled to the carriage, rotation of the beam screw causing linear motion of the carriage along a length of the beam spring, the carriage forming a structural pivot for dynamic control of the deformation of the beam spring. A drive motor 71 can be coupled to the beam screw for providing rotation of the beam screw. In another example, as illustrated in FIGS. 19A-19C, the device includes a carriage 70 and a shock absorber 78 that extends parallel to the beam spring and engages the carriage, the shock absorber providing linear motion of the carriage along a length of the beam spring, the carriage forming a structural pivot for dynamic control of the deformation of the beam spring.

The actuators 1, 2 of FIGS. 1 and 2A-2B can be controlled in a torque control mode or with an impedance controller that generates a desired torque command. Example architectures of a suitable torque control systems are outlined in FIGS. 17A and 17B. If the on-board controller is the high-level controller then it may determine desired command signals to send to the torque or impedance controller based on a state machine, or another linear or non-linear control scheme as appropriate to the application. Suitable control schemes are described in Au and Herr, 2008, and Markowitz et al., 2011 (S. K. Au and H. M. Herr, "Powered Ankle-Foot Prosthesis," IEEE Robot. Autom. Mag., no. September, pp. 52-59, 2008; J. Markowitz, P. Krishnaswamy, M. F. Eilenberg, K. Endo, C. Barnhart, and H. Herr, "Speed adaptation in a powered transtibial prosthesis controlled with a neuromuscular model," Philos. Trans. R. Soc. Lond. B. Biol. Sci., vol. 366, no. 1570, pp. 1621-31, 2011), the teachings of which are incorporated herein by reference. The motor driver controls the physical actuator by commanding current to the motor 21 built into the actuator. Sensors on the actuator feedback into the controller. A high-level controller can directly determine a desired torque to be commanded to the actuator, or alternatively an impedance controller can be utilized.

Figure 17A:
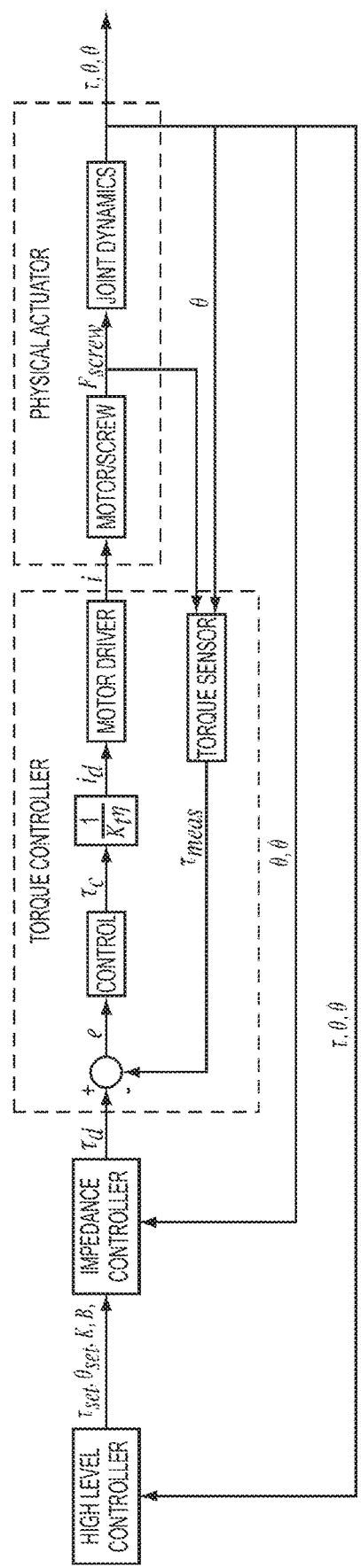
FIGS. 17A-17B show block diagrams of mid-level controllers for use with actuators according to embodiments of the invention.
Figure 17B:
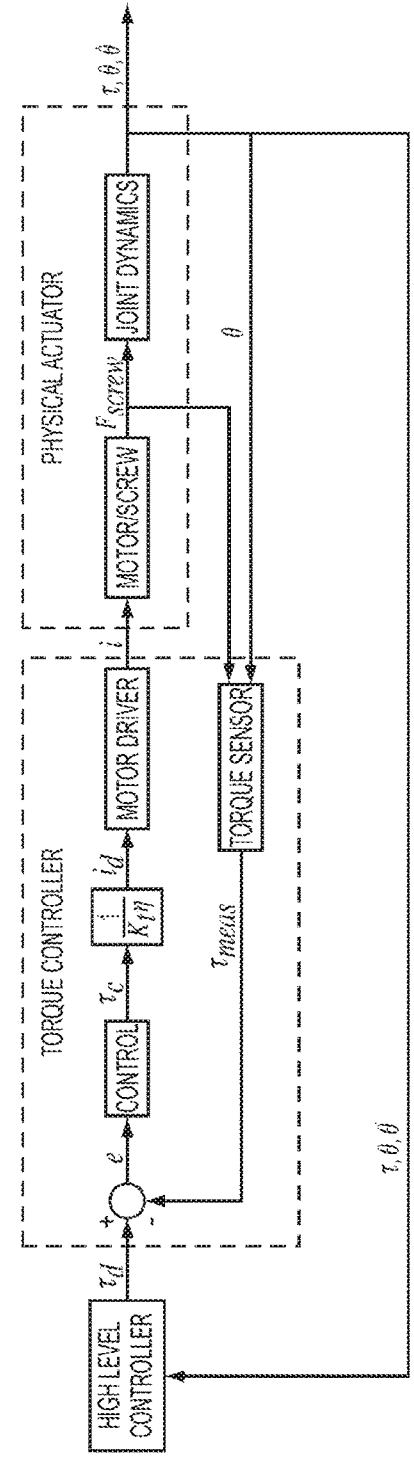

A simple impedance controller, as illustrated in FIG. 17A, generates a desired torque by treating the output as a mass with a spring and damper:

$$t_d = K(\theta_d - \theta_m) + B(\dot{\theta}_d - \dot{\theta}_m)$$

Where, $K$ is a desired torsional stiffness, $B$ is a desired torsional damping rate, $\theta_d$ and $\dot{\theta}_d$ are desired angle and angular velocity, and, $\theta_m$ and $\dot{\theta}_m$ are measured joint angle and joint angular velocity. The desired torque from this or an alternative controller is then sent to the torque control loop. The torque control feedback loop compares desired torque and measured joint torque and applied a control algorithm to determine a controller torque signal that is transformed into a desired motor current by multiplying by the inverse of the motor torque constant, Kt and an efficiency term representing the drivetrain efficiency. A desired current is then sent to the motor drive that has its own, internal, low-level current controller that commands current to the motor. The motor transforms current into rotary motion that drives the nut 32 along the screw 23, generating an axial force in the screw 23 that drives the output arm 14. The torque sensor shown in FIGS. 17A and 17B determines the joint torque by applying a correction factor to the axial force based on the measured geometry of the orientation of the screw with respect to the output axis of rotation. That is, as the output arm 14 rotates about its axis 37 its orthogonal distance to the axis changes, affecting the overall gear ratio of the actuator and the effective torque for a given axial force.

To operate the electronics and provide power to the motors a direct-current electrical energy source is necessary. For a mobile (e.g., wearable) system, the electrical energy storage may be a battery pack mounted on or nearby to the actuator. Similarly, the embedded systems 58 can be mounted within the package of the actuator structure or can also be mounted externally. The actuator used as a powered prosthetic ankle joint can be mounted onto a prosthetic socket 91 illustrated in FIG. 12.

Figure 12:
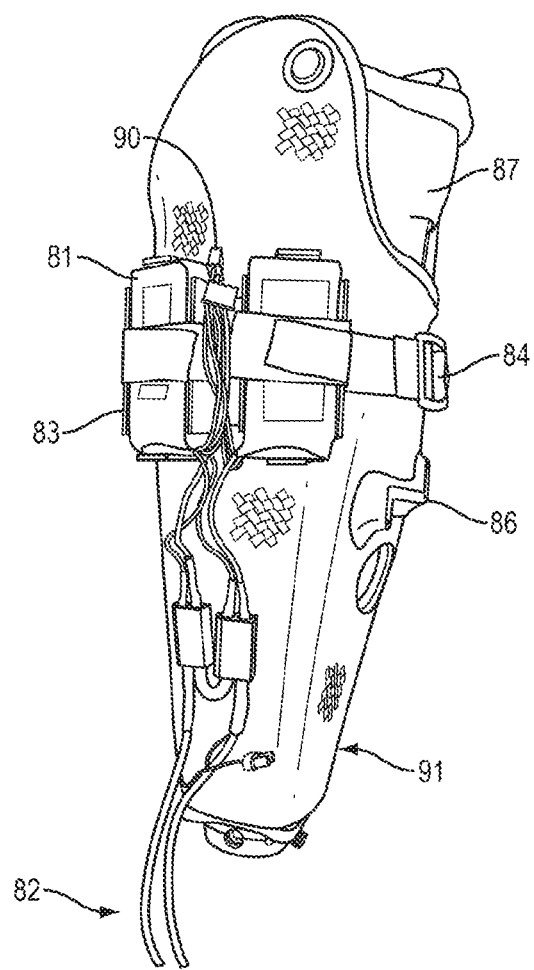
FIG. 12 shows one configuration of a battery holster mounted to a socket utilizing straps to affix the battery holster. A mounting bracket is integrated into the structure of the socket to attach electronic modules.
Figure 13:
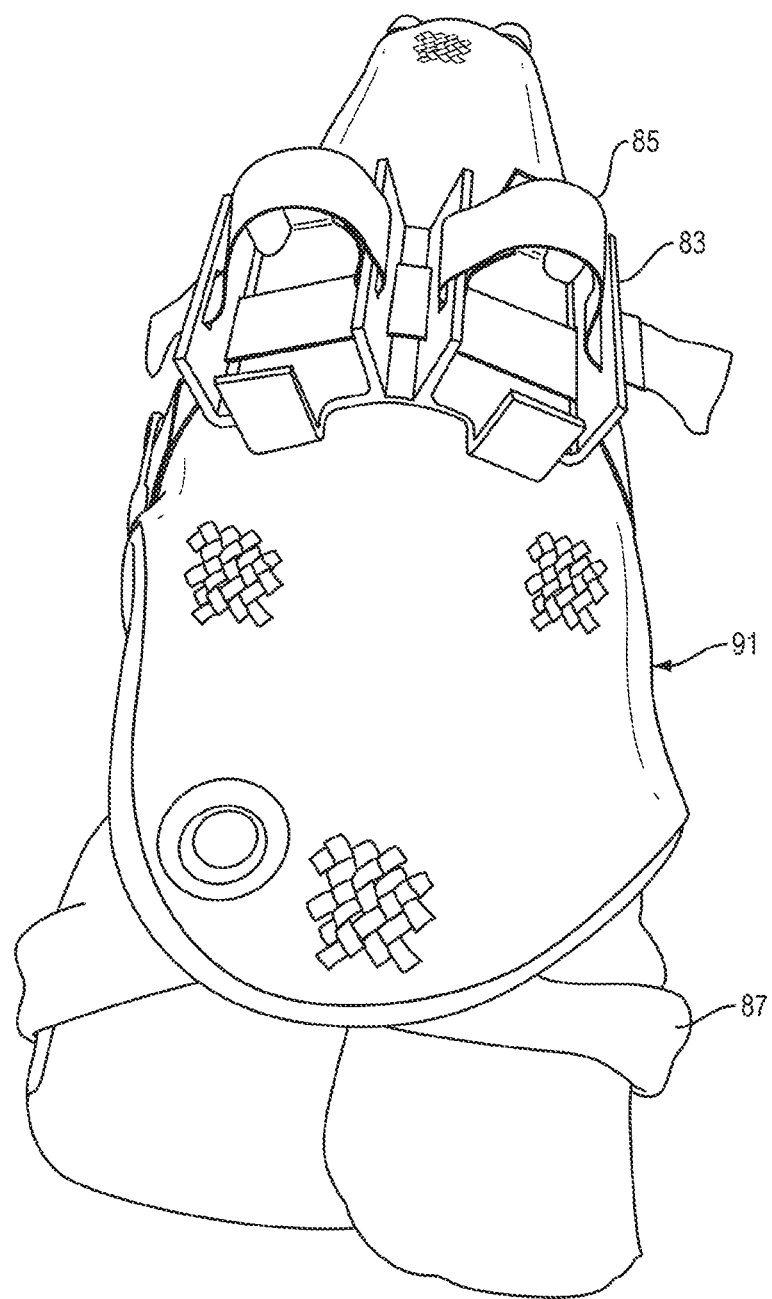
FIG. 13 illustrates the battery holster and straps that affix batteries in place on a socket.
Figure 15:
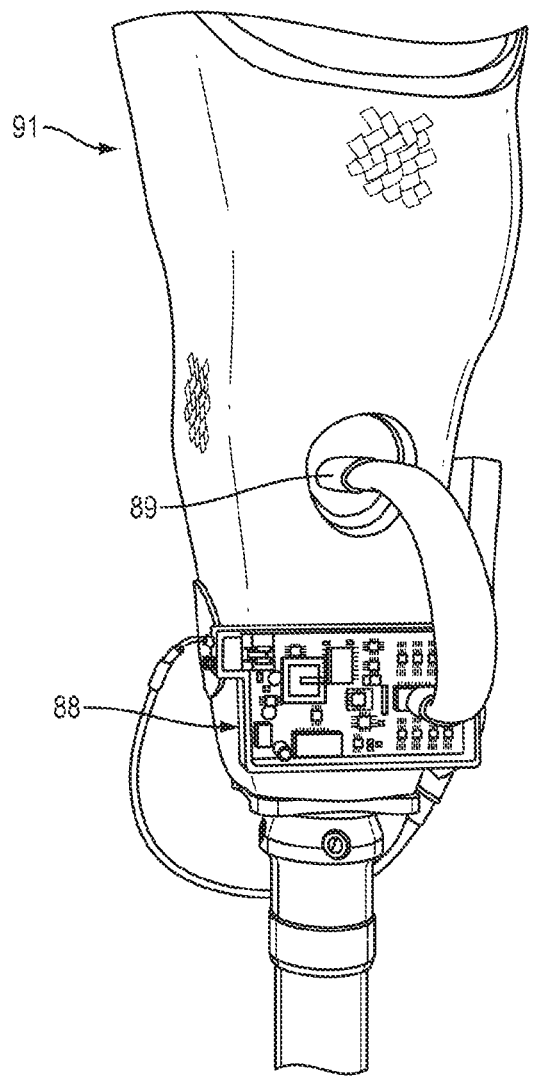
FIG. 15 shows the connected custom liner, socket, and sEMG system for augmenting an active prosthetic actuator's capability with volitional control of the user.

In FIGS. 12, 13, and 15, battery pack 81 and electronics and related components 82-90 are shown to be mounted to the prosthetic socket 91. These include power wires 82, battery mount fixture 83, battery mount strap 84, battery enclosure strap 85, electronics mounting fixture 86, EMG socket liner 87, EMG electronics 88, EMG wires 88, and communication wires 90. In these figures, the battery 81 is mounted to a battery fixture component 83 by battery enclosure straps 85, which is strapped to the socket 91 with mounting straps 84. Power cables or wires 82 transmit electrical energy from the battery pack 81 to the electronic systems 58 and any other peripheral electronics such as the EMG system 88 or Bluetooth communication modules. Additional rigid mounting of the battery and/or electronics can be performed by rigid mounting features built into the socket, shown as 86 in FIG. 12. The battery attachment system can also be rigidly affixed to mounting features in the socket. In this way the battery enclosure 81-85 can be entirely contained within a rigid structure to protect from environmental conditions.

Figure 14:
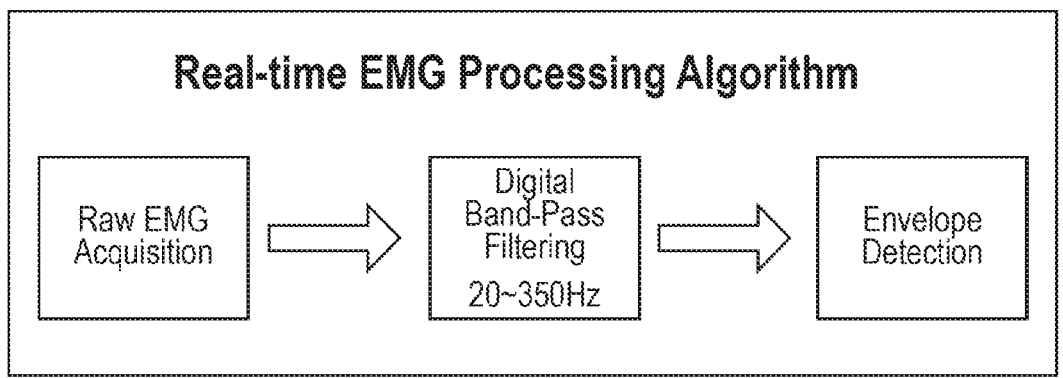
FIG. 14 shows an example block diagram for real-time sEMG processing.

As an example of volitional control, the actuator has been tested with the custom, integrated sEMG system illustrated in FIGS. 12-15 and components 86-91. FIG. 15 shows the prototype of the sEMG system used as an embodiment of proposed actuator architecture where the sEMG system operates as a peripheral device in the system depicted in FIG. 16. The sEMG system captures electrical activities of muscles and processes the activities to the estimation of relative muscle activations. These estimated muscle activations can be fed into a high-level dynamic controller to generate torque, velocity, and position profiles for the actuator. FIG. 14 shows an example of a generic algorithm of real-time processing of sEMG signal on embedded system, as further described in Clancy et al., 2004 (E. A. Clancy, D. Farina, and G. Filligoi, Single-channel techniques for information extraction from the surface EMG signal. In: Electromyography (eds R. Merletti and P. Parker). 2004), the teachings of which are incorporated herein by reference.

Custom built socket 91 and liner system 87 can augment the capability of the actuator systems. For example, the sEMG system, explained above, can easily be physically integrated with the new actuator architecture with special socket and liner built for prosthetic neural interface system. The prosthetic liner with integrated electrode, made by conductive fabric, provides robust electrical output interface to access the muscle activation from the electronics, and the specially built socket provides physical stability while allowing to access the liner's output interface. FIG. 15 shows the custom-built liner connected via EMG wires 89 to the sEMG embedded system mounted on the socket.

Overview of Non-Backdrivable 2-DOF SEA System

The invention generally is directed to any actuator system that benefits from precise position control of a 1 or 2 degree of freedom joint via a non-backdrivable transmission, in a low power, low mass package.

Actuator

In one embodiment, the invention is a linear actuator that includes a motor connected to a screw reduction, driving a nut that is constrained to the frame, resulting in linear motion of the actuators corresponding to rotary motion at the joint. The nut is fixed on the base such that is cannot rotate, forcing linear translation of the actuator in a smaller package than is typically seen from linear actuators using a linear guide rail.

System

In one embodiment, the invention achieves 2-degrees of freedom with a differential transmission between the two actuators to allow for motion about two orthogonal and intersecting axes. The system includes a spring in series with the actuator, allowing for the spring equilibrium point to be actively adjusted while walking.

Control

The system is controlled by an embedded electronic control system that drives the motors, reads sensor data, and controls the system according to the programmed controller. The system can be used in conjunction with surface electromyography (sEMG) electrodes to measure the user's muscle activation. An onboard EMG processing board is used to filter and amplify the signal before sending the data to the control system. The control system uses one of the following methods to convert EMG signal to desired joint position: machine learning, proportional control, or computation using a dynamic virtual joint model. Load cells can be used to detect the stance phase of gait. During stance, the motors are not driven; the non-backdrivable transmission allows the ankle to hold its position during stance while consuming no additional power. During swing, the data from the EMG board is used to control the position of the ankle-foot.

Features of embodiments of the non-backdrivable 2-degree of freedom SEA system include:
a) Actuator
   i. Non-backdrivable
     1) Can greatly reduce device weight and complexity
     2) Low power
     3) Quasi-passive
   ii. Load cell in line with actuator
     1) Allows for accurate force thresholding of control system,
     2) Haptic force feedback
     3) Force control
   iii. Positional control
b) System
   i. 2 dof ankle
   ii. Differential lead screw
   iii. U-joint prevents rotation of nut, creating linear motion
   iv. Series—elasticity
     1) Change spring equilibrium point during swing
       a) Modulated based on EMG neural signal
       b) Intrinsically based on ankle-foot orientation and position
       c) Can add series elasticity to system
       d) Allows for high fidelity torque control
c) Control
   i. Efferent Neural Control
   ii. Intrinsic
   iii. Diagram of swing/stance
   iv. Modulate spring set point
   v. Modulate dampening
   vi. Afferent feedback
   vii. Automatic, online, intrinsic learning of walking tasks and terrains Details of Non-Backdrivable 2-DOF SEA System The actuator shown in FIGS. 20-25B is a non-backdriveable linear actuator. It is fundamentally composed of a displacement mechanism that applies a torque about an output axis. The displacement mechanism is a mechanical transformer that converts rotary motion into linear motion by rotating a screw through a non-rotating nut. The screw is coupled to a direct current motor through a flexible shaft coupling, such that rotation of the motor directly rotates the screw, causing the nut to translate linearly. The distance traveled by the nut per each rotation of the motor is determined by the lead of the screw. The lead of the screw is defined as the linear travel for one rotation. The lead of the screw in conjunction with the length of the output moment arm determines the overall transmission of the system. The nut is attached to the base plate via a pivoting universal joint (U-joint), which allows for motion along the output axes while preventing rotation of the nut. The motor is mounted to the frame via a pivoting U-joint. This mounting orientation prevents the motor from spinning while the rotor spins.

FIGS. 20-23 show the actuator utilized as an ankle joint in a prosthetic device for persons with trans-tibial (below knee) amputation. The actuator can also be implemented as any other joint requiring a torque about one or two axes.

In FIGS. 20-23, the actuator device 110 is configured as a robotic ankle with a standard prosthetic flex foot 122 attached to the distal end. Foot adapter 123 may be eliminated or modified to allow for the mounting of other types of prosthetic feet. This allows for the optimization of performance for activities other than walking—including rock climbing, swimming, and running.

Figure 20:
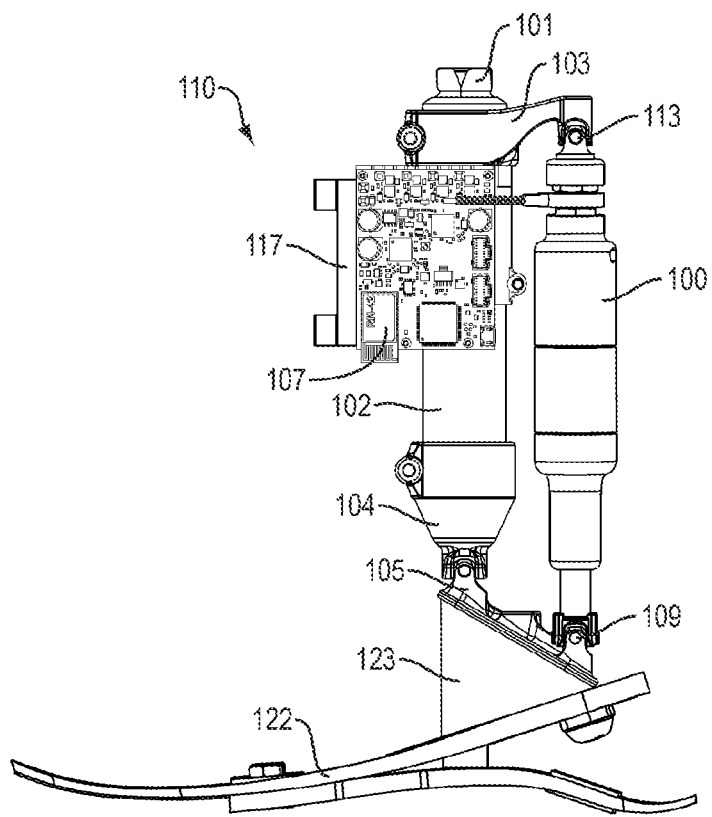
FIG. 20 shows a side view of an actuator system configured as a 2-degree of freedom ankle-foot prosthesis.
Figure 21:
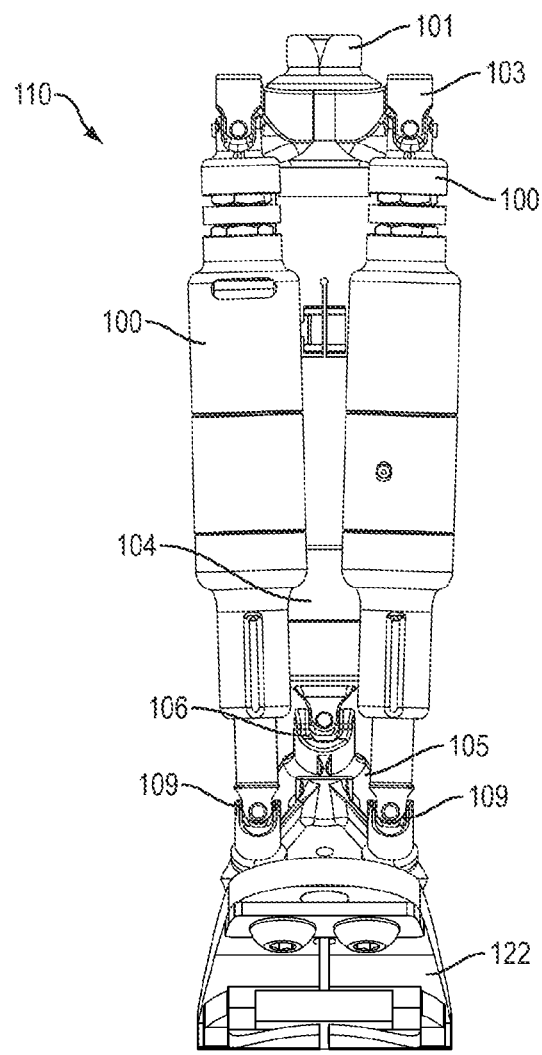
FIG. 21 shows a back view of the system configured as a 2-degree of freedom ankle-foot prosthesis.

FIG. 20 shows details of many components of the actuator system. Base plate 105 and ankle joint component 104 pivot about two orthogonal and intersecting axes, allowing foot 122 to rotate about the primary and secondary axes with respect to pylon 102. Actuator mounting points 109 and 113, positioned some distance away from the central universal joint 106, anchor the distal end of the nuts of each actuator 100. As illustrated in FIG. 21, there are two actuators 100 in the device 110, each coupled between a bracket 103 and the base plate 105. A standard pyramid adapter 101 is provided to allow attachment of a prosthetic socket or other component.

Figure 22:
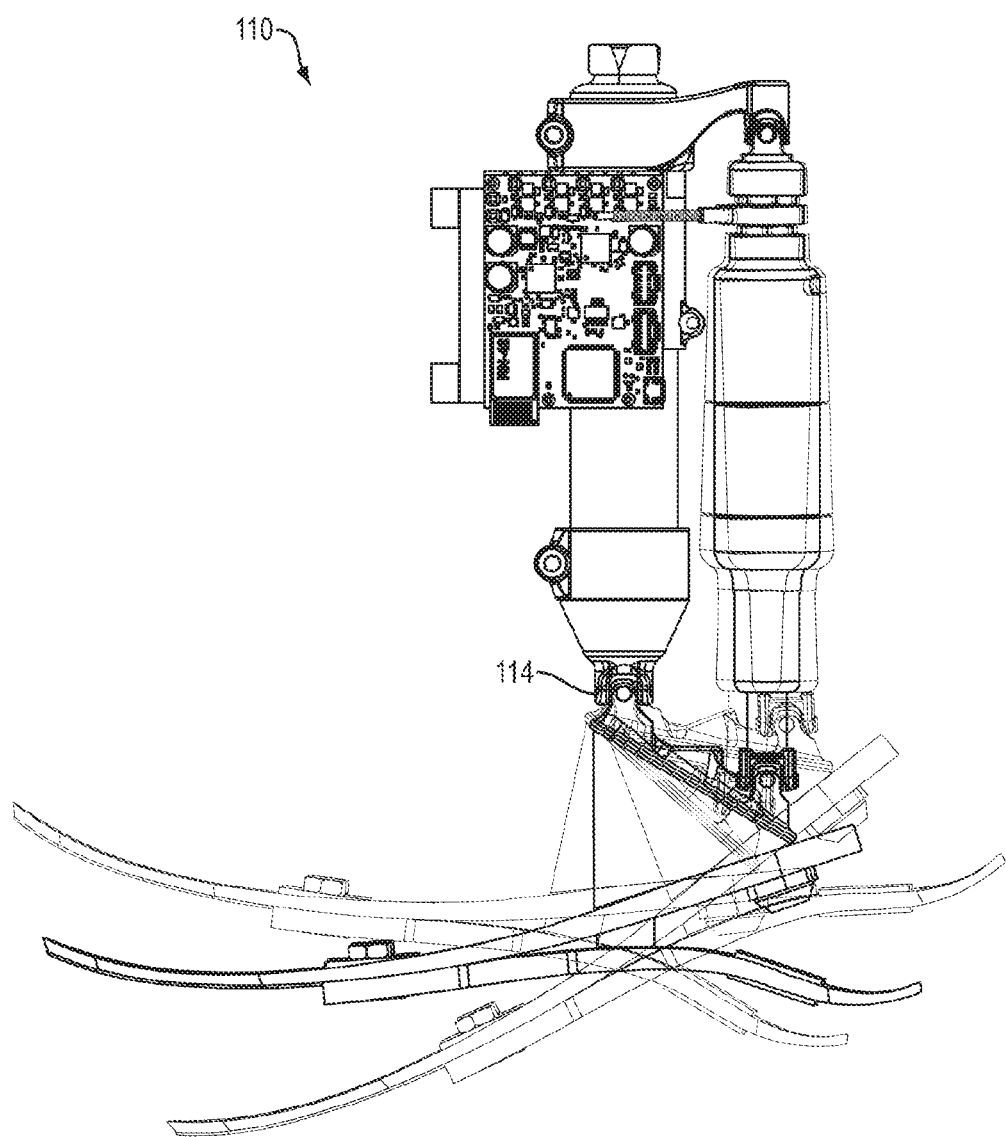
FIG. 22 demonstrates actuation of the device resulting in motion about the primary axis, resulting in plantar flexion and dorsiflexion about the ankle joint.
Figure 23:
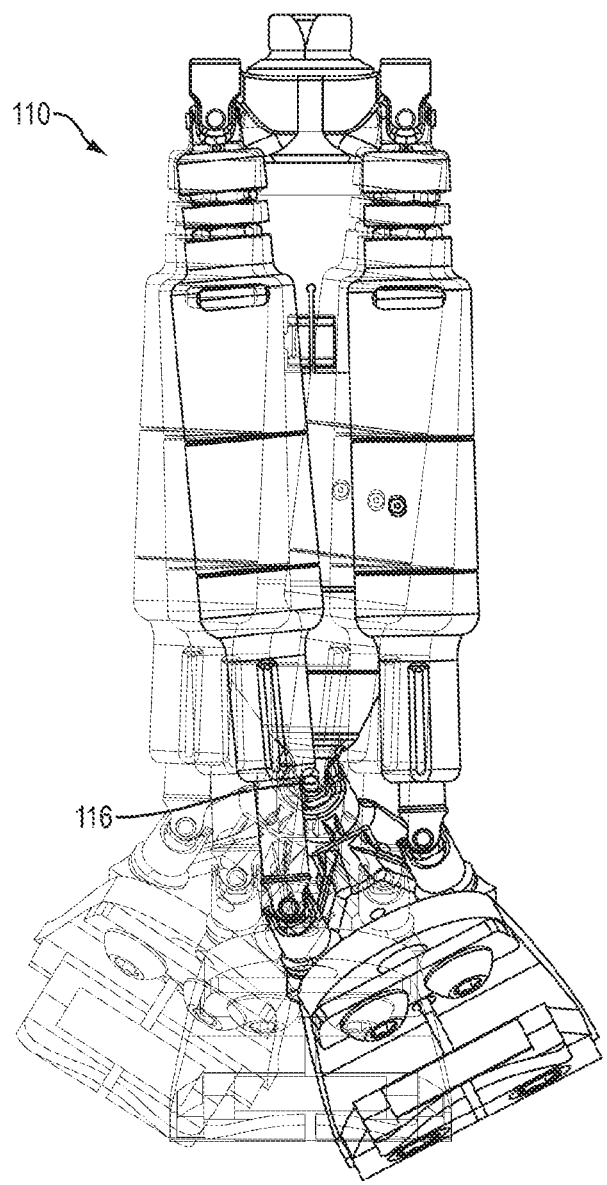
FIG. 23 demonstrates actuation of the device resulting in motion about the secondary axis, allowing for inversion and eversion about the subtalar joint.

As illustrated in FIGS. 22 and 23, the device 110 may be actuated about two axes, allowing for rotation of the foot in two degrees of freedom. FIG. 22 demonstrates rotation about a primary axis, ankle joint axis 114, achieved by driving both actuators in the same direction. This allows for the foot to move in plantar flexion and dorsiflexion in the configuration as an ankle prosthesis. The second degree of freedom is actuated by driving each actuator in opposing directions. FIG. 23 demonstrates motion about the second degree of freedom, subtalar joint axis 116, allowing for inversion and eversion of the foot about the subtalar joint in this application.

Figure 24:
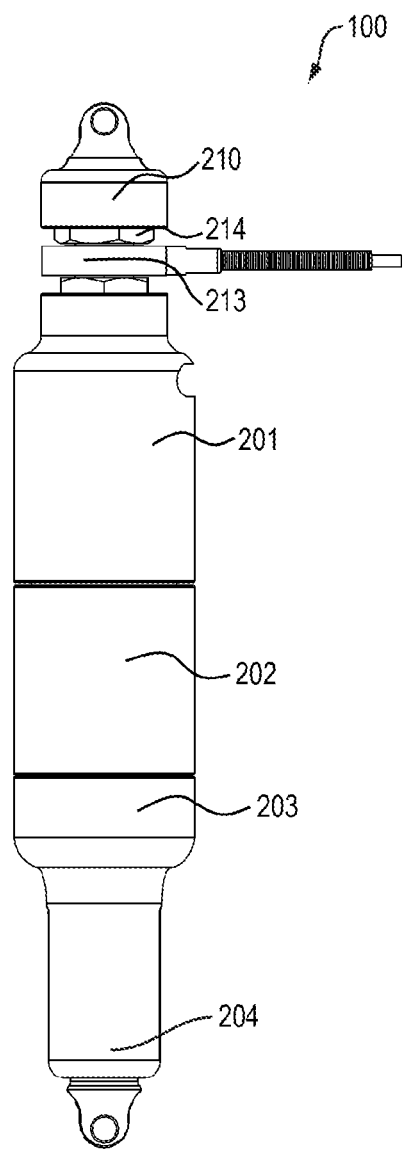
FIG. 24 shows a side view of a single actuator.
Figures 25A, 25B:
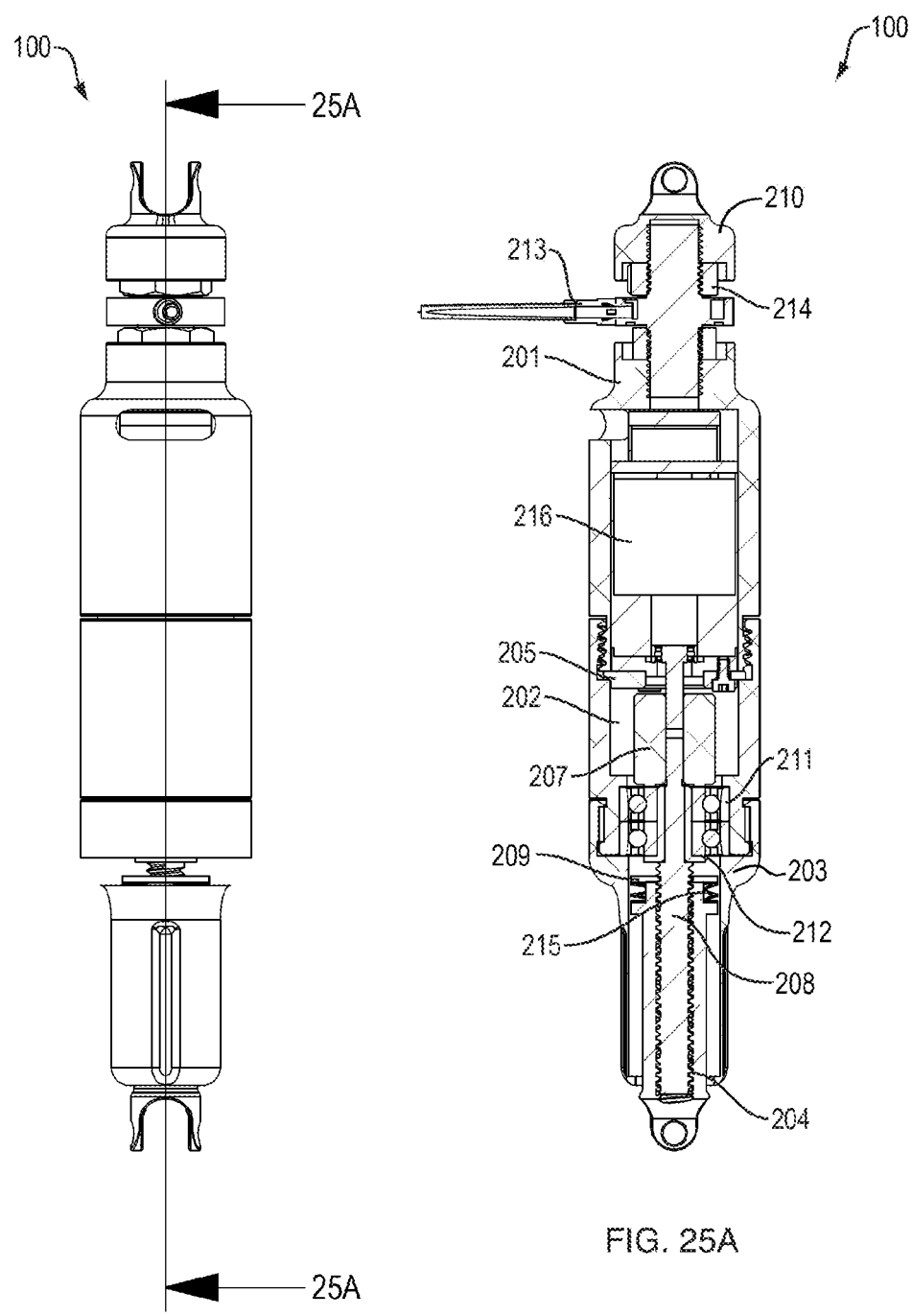
FIG. 25A shows a cutaway view of the internal components of the actuator of FIG. 24.
FIG. 25B is a front view of the actuator of FIG. 24 with a partial cutaway of the actuator housing to show the screw.

FIGS. 24 and 25A-25B show details of the linear actuator 100, with FIG. 25A showing a section view of the actuator. Screw 208 interfaces with nut 204, with spring 215 compressed between nut 204 and secondary nut 209 in order to preload the nut, decreasing backlash observed at the onset of motion or during directional changes. The proximal end of screw 208 is supported by a pair of angular contact bearings 211, the bearings pass the thrust loads of screw 208 to motor housing 201, as well as any radial loads resulting from misalignment of screw 208 and rotor axis of motor 216. The motor housing transmits the load via the motor mount universal joint 109 to bracket 103, attached to the proximal end of pylon 102. A load cell 213 is secured with a locknut 214 between mounting flange 210 and motor housing 201. The inner races of angular contact bearings 211 are preloaded between spacer flange 212 on the proximal end of screw 208, and flexible shaft coupling 207 which threads onto the screw and is fixed into place using a set screw. The outer races of the angular contact bearings 211 are preloaded between actuator housing 203 and bearing housing 202. Motor 216, in this case a brushed direct current motor (Maxon DCX 22S), is attached to motor mount plate 205, which mates with motor housing 201 to prevent rotation of the motor.

The screw 208 and nut 204 are a non-backdrivable lead-screw arrangement. The lead and screw profile make it non-backdrivable. A lead-screw include a cut thread and nut with low efficiency, where friction prevents back-driving. In contrast, a ballscrew provides high efficiency, low friction, enabling backdriving.

Onboard microprocessor 107 regulates the voltage supplied to motor 216. The microprocessor 107 is programmed to analyze data from load cell 213 and is programmed to analyze sensor input and modulate motor output torque accordingly. The electronics convert data acquired from the encoders from motor 216, load cells 213, temperature and current sensors on microprocessor 107, and sEMG electrodes and convert it to the desired motor torque output.

FIGS. 26-28B demonstrates the configuration of the device as a series-elastic actuator, during the unloaded state the equilibrium point of the spring may be adjusted by changing the position of the ankle about each axis. The position adjustment may be controlled volitionally via EMG neural input from the EMG system, or automatically based on sensor data interpreted by an intrinsic controller on the microprocessor. Spring equilibrium adjustment allows the equilibrium position of the joint compliance of the system to be optimized for terrain, gait speed or movement task, including but not limited to ascending and descending stairs, ascending and descending slopes, slow vs. fast walking speeds, and sit-stand maneuvers. Additionally, the spring equilibrium control of a series compliance allows for energy to be stored during certain portions of the gait cycle, and injected back into the stride.

Figure 26:
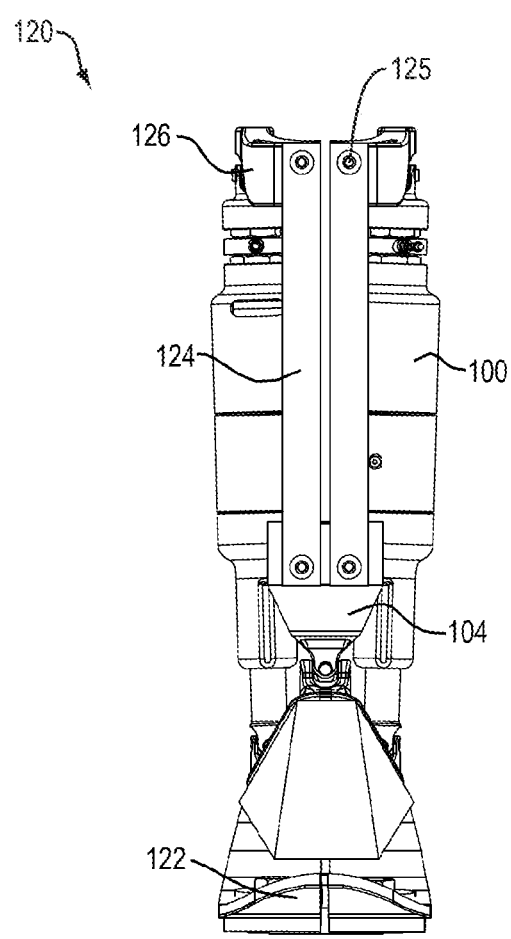
FIG. 26 shows a front view of a prosthesis configured as a series elastic actuator utilizing cantilever beams as an elastic element.
Figure 27:
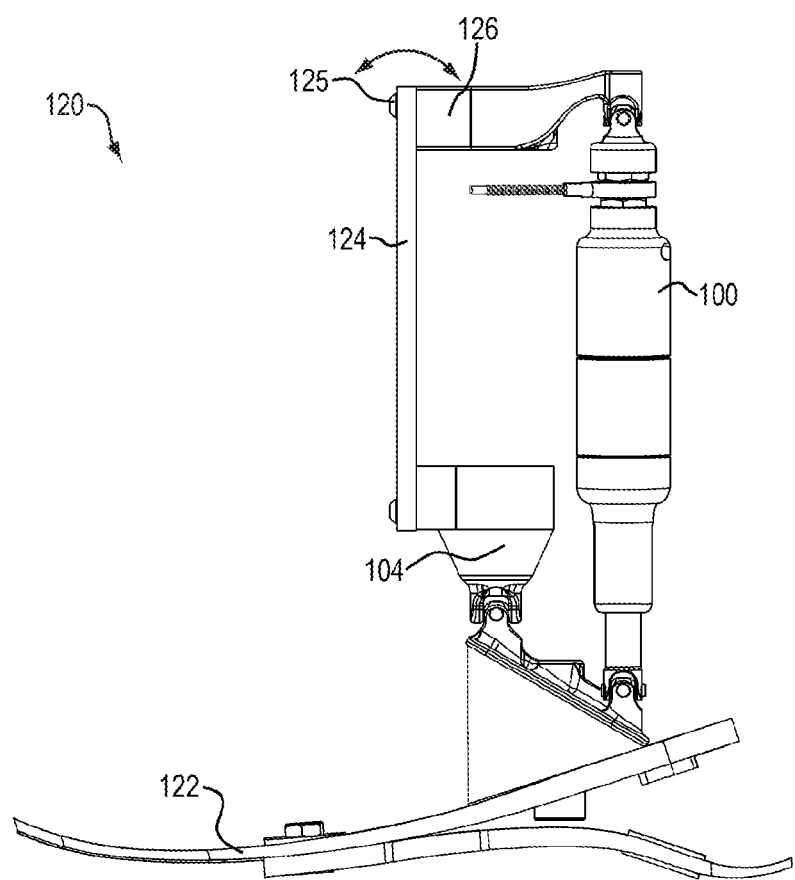
FIG. 27 shows a lateral view of the prosthesis of FIG. 26.

FIGS. 26-27 show the device configuration 120 in which the series spring is cantilever beam 124 in bending. Attachment bolts 125 affix the spring member to mounting bracket 126 and ankle joint 104. There is a separate spring member for each actuator 100, with a strain gauge on each spring member 124 to allow for the measurement of the spring deflection. Actuator 100 attaches to mounting bracket 126 and foot 122. In FIG. 27, a curved arrow shows the direction of spring deflection of spring 124 under load.

Figure 28A:
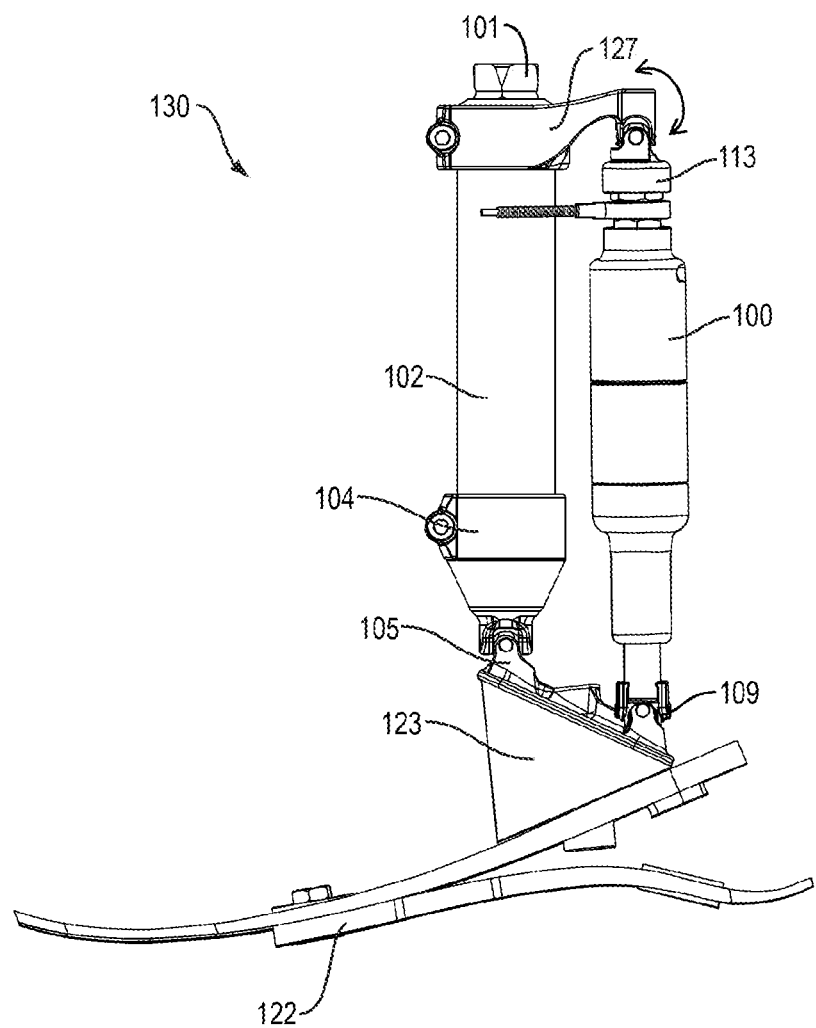
FIGS. 28A and 28B are side and front views of a system configured as a series elastic actuator where a bracket is a series spring.
Figure 28B:
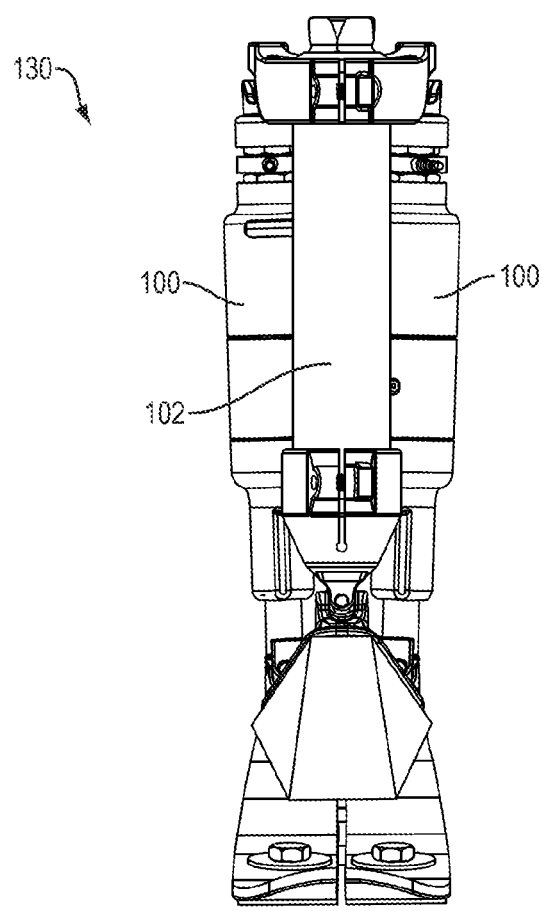

FIGS. 28A-28B illustrate the device configuration 130 in which bracket 127 acts as the elastic member, and deflection is measured using strain gauges affixed to bracket 127. An arrow in FIG. 28A shows the deflection of bracket 103 under load. Actuator 100 is mounted to bracket 127 and footplate 105.

The embodiment described above and shown in FIGS. 26-28B provide for an ankle-foot device that includes a foot member 105 and an ankle member 104 that are connected for two-degree of freedom movement relative to one another allowing for rotation about an ankle axis and rotation about a subtalar axis, to thereby define an ankle joint and a subtalar joint. The device includes two linear actuators 100, each actuator including a motor and a non-backdriveable transmission, each actuator coupled at one end to the foot member and at the other end to a corresponding series elastic element attached to the ankle member, wherein driving the actuators in the same direction causes rotation about the ankle axis and driving the actuators in opposing directions causes rotation about the subtalar axis. The device further includes at least one sensor 213 and a processor 107 communicatively linked to the actuators and the at least one sensor. The processor is configured to receive sensory information from the at least one sensor and drive the actuators to control an equilibrium position of the series elastic elements during a swing phase of a gait cycle to improve ankle-foot device function during a subsequent stance phase of the gait cycle.

Figure 29:
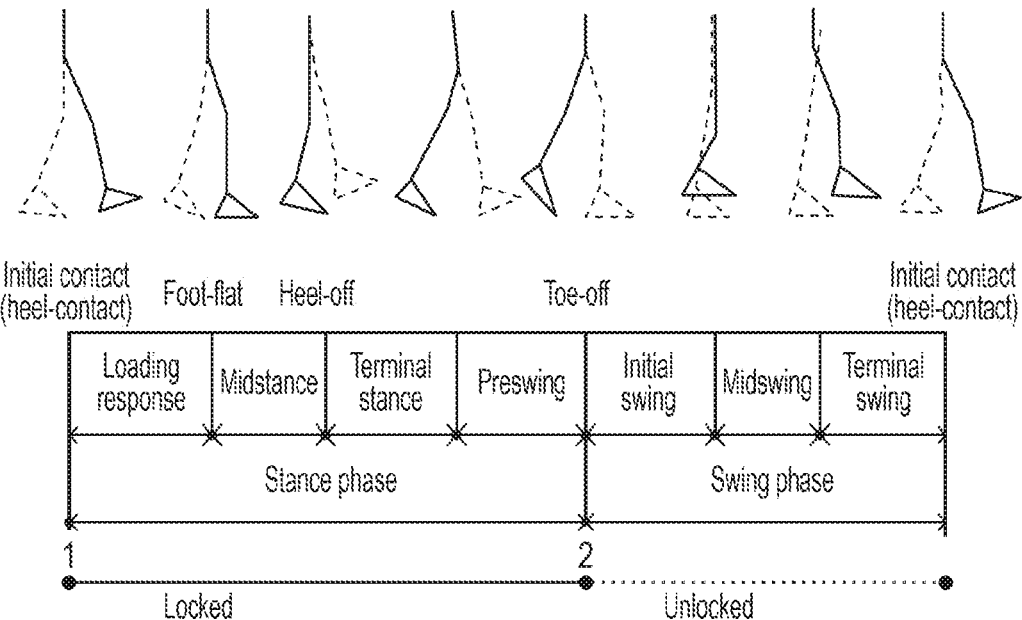
FIG. 29 shows a schematic diagram of the normal gait cycle. During the swing phase of walking, the described invention allows for position control of the ankle, about 2 degrees of freedom. During stance the system is non-backdrivable, holding the ankle position while drawing no additional power.

FIG. 29 illustrates a basic control scheme of the presented device (see also E. Zheng and Q. Wang, Noncontact Capacitive Sensing-Based Locomotion Transition Recognition for Amputees With Robotic Transtibial Prostheses, *IEEE Transactions on Neural Systems and Rehabilitation Engineering*, vol. 25, no. 2, pp. 161-170, February 2016). This control scheme can be applied to prostheses used for walking, running, rock climbing, dancing, diving, skiing, and any other activity that is comprised of "swing" and "stance" phases. When the device is not supporting the weight of the user—such as during swing phase of walking—the device provides powered positional control. This position control is modulated through volitional control based on muscle activation signals measured from the residual limb musculature. When the device is loaded, the control system is in a standby state, requiring no additional power to hold the ankle in its position due to the non-backdrivable transmission. This control scheme in combination with the presented hardware design allows for adjustment of foot position throughout the gait cycle, allowing the user to adjust foot clearance during swing—providing increased maneuverability across uneven terrain. In addition, foot position may be adjusted while ascending or descending stairs, ascending or descending slopes, and navigating cross-slopes. The control scheme can be outlined as follows:
1) Load cell detects force on actuators indicating foot-contact, no current provided to the motor(s), and actuator(s), locking joint(s) position in place
2) Load cell detects no force on actuator(s) indicating foot-off, volitional position control of joint via an EMG neural input from the user.

Figure 30:
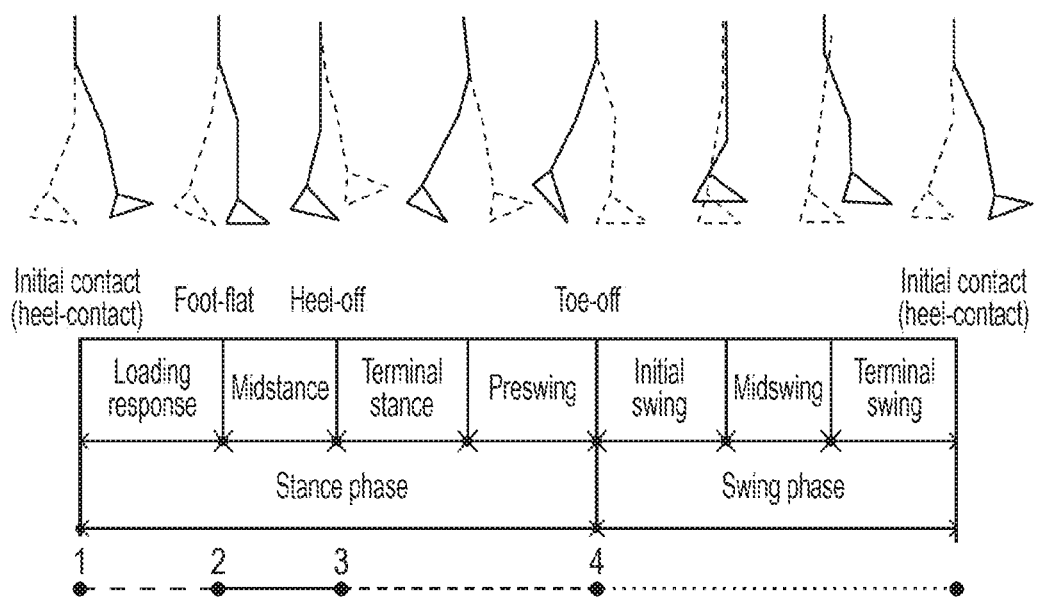
FIG. 30 shows a schematic diagram of device control for normal gait in the series spring configuration. Active dampening is performed during loading response, and energy is stored in the spring during foot flat and released during terminal stance.

FIG. 30 illustrates a more sophisticated version of the control scheme, allowing for damping and energy storage throughout the gait cycle. Sensors in the device such as electromyography sensors, load cells, accelerometers, and gyroscopes are used to detect state transitions in the gait cycle. The control scheme is outlined as follows:
1) Foot-strike is detected based on force or torque measured by load cells. During loading response when the ankle torque is negative (heel load), the controller applies active joint damping by driving the motor(s) in an ankle plantar flexion direction through the non-backdriveable transmission.
2) Near the point of foot-flat, the controller outputs zero motor current at a desired ankle spring equilibrium angle, as measured by an ankle joint encoder. This angle is called the zero-current position (ZCP). The ZCP is approximately a neutral angle at slow gait speeds, or a plantar flexed angle that increases with increasing gait speed. At the ankle angle at which the controller applies the zero motor current, or the ZCP, the nonbackdriveable transmission assumes a locked orientation. Further joint rotation occurs due to series spring compression during midstance, or controlled dorsiflexion. The ZCP is determined by the controller based upon a functional relationship between ZCP and gait mode, or gait parameter(s) that correlate with gait mode such as, for example, foot-strike ankle angle, early stance torque, torque rate, and/or the time from foot-strike to foot-flat. For example, if the foot-strike angle is neutral (90 degrees), early stance torque is negative (heel load), and the time from foot-strike to foot-flat is relatively large, the user is assumed to be walking slowly on a level ground surface. For this gait mode, the ZCP would be set equal to a neutral or a small plantar flexed angle. In distinction, if the foot-strike angle is plantar flexed and the early stance torque is positive (dorsiflexion moment denoting a toe-strike), the ZCP would be set equal to a dorsiflexion angle appropriate for stair descent (~10 degrees of dorsiflexion). Still further, if the foot strike angle is dorsiflexed and early stance torque is negative (heel load), the user is assumed to be walking up a modest incline. For this gait mode, the ZCP would be set equal to the measured foot-strike angle. Further, measured EMG signals from the user could be used to adjust the ZCP. For example, for non-zero calf muscle EMG values, the ZCP could be increased to provide a greater plantar flexion angle. In distinction, for non-zero tibialis anterior EMG values, the ZCP could be decreased to provide a greater dorsiflexion angle.
3) Series spring returns elastic energy during terminal and pre-swing stance phases, or powered plantar flexion. The toe-off angle would be equal to the ZCP selected earlier in stance.
4) Toe-off detected based on force or torque measured by the load cells. Immediately following the toe-off detection, the motor is controlled to move the ankle joint back to a neutral position in order to achieve foot clearance. During the late swing phase, the controller reads EMG signals, and adjusts the ankle angle in preparation for the next foot-strike. If no EMG signal is detected (relaxed muscle activity), the ankle angle would assume a neutral position, approximately equal to 90 degrees. For non-zero calf muscle EMG values, the motor would servo the ankle angle during late swing to a plantar flexed position. In distinction, for non-zero tibialis anterior EMG values, the motor would servo the ankle angle to a dorsiflexed position.

The device may facilitate walking on varied terrain such as ascending and descending slopes, ascending and descending stairs, and traversing cross slopes.

Figure 31:
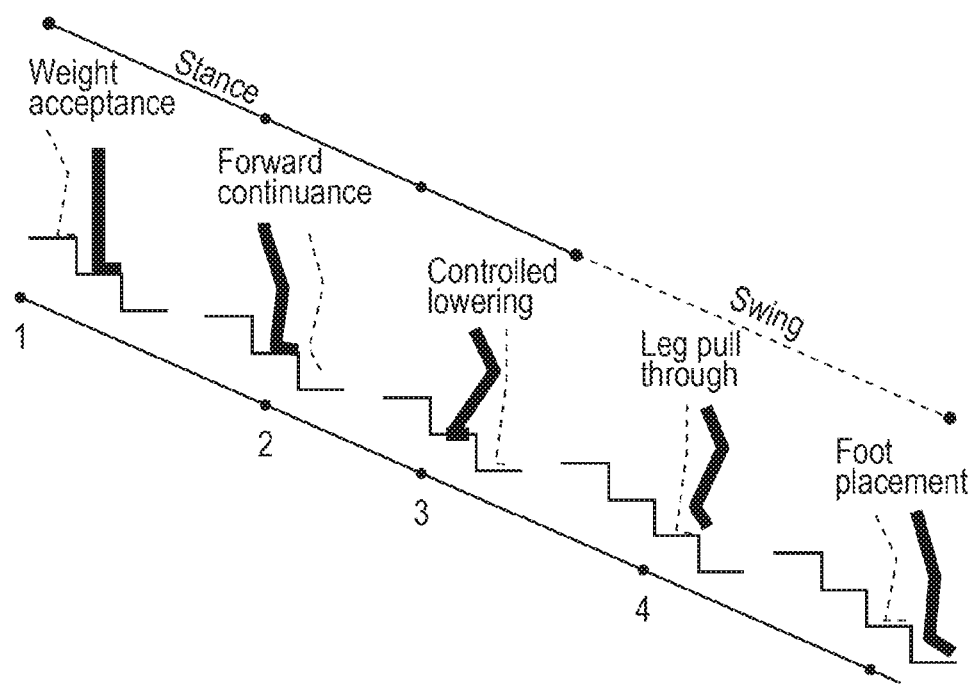
FIG. 31 shows a schematic diagram of device control on varied terrain (stair descent in this example), utilizing features of the series elasticity, non-backdrivability, and active dampening.
Figure 32:
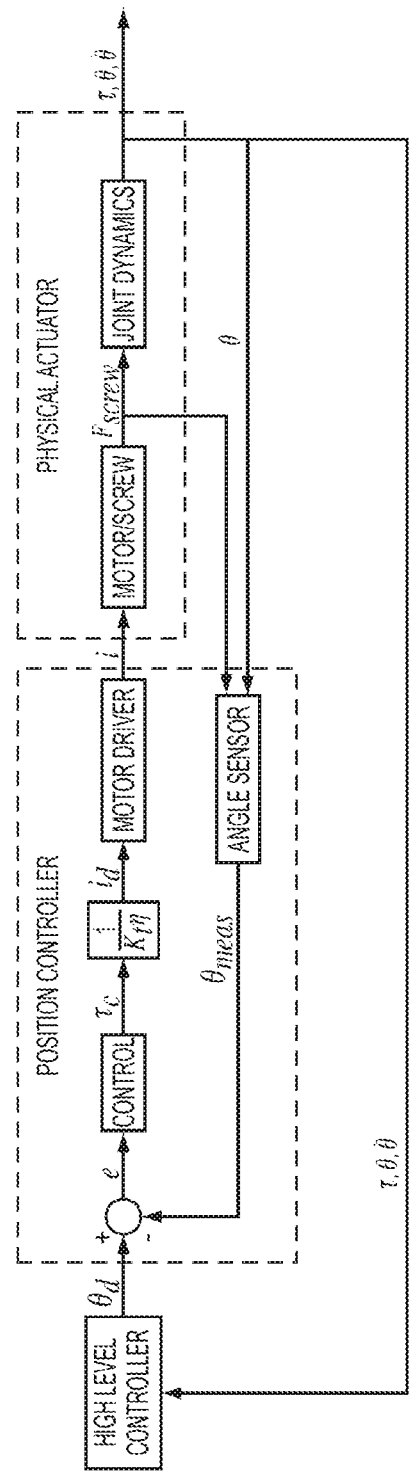
FIG. 32 illustrates a position-controlled control system in its most general form.

FIG. 31 outlines a control scheme during the gait cycle for stair descent (see also A. Spanias et al., Online adaptive neural control of a robotic lower limb prosthesis. *Journal of Neural Engineering*, vol. 15, no. 1, February 2018). Upon initial contact of the toe, the actuators are driven in the dorsiflexion direction (1), to allow for a dampened movement towards foot flat. During foot-flat, the motors are turned off and the non-backdrivable actuators lock the joint in place (2). Energy is stored in the series spring during foot flat. During controlled lowering the ankle is further dorsi-flexed (3), dampening the motion by driving the actuators in the same direction as the torque about the ankle. Toe-off is detected by force measurement through the load cells. Upon toe-off the foot is dorsiflexed to allow for toe clearance and then plantar flexed prior to foot placement (4). This swing phase motion may be modulated volitionally by the user via EMG input, or intrinsically based on a preprogrammed gait pattern. The control scheme can be summarized as follows:
1) Initial foot-strike detected based on force measured by load cells. The controller applies active joint damping by driving the motor in a dorsiflexion direction through the non-backdriveable transmission.
2) Near the point of foot-flat, the controller outputs zero motor current at a desired ankle spring equilibrium angle, as measured by an ankle joint encoder. This angle is called the stair descent zero-current position (SDZCP). The SDZCP is a dorsiflexed angle. At the ankle angle at which the controller applies the zero motor current, or the SDZCP, the nonbackdriveable transmission assumes a locked orientation. Further joint dorsiflexion rotation occurs due to series spring compression during controlled lowering.
3) Toe-off detected based on force measured by load cells. Plantar flexion occurs during the late swing phase prior to foot placement on the next stair tread via EMG inputs from the user. If no EMG signal is detected (relaxed muscle activity) during late swing, the ankle angle would assume a neutral position, approximately equal to 90 degrees.

The high level control scheme on embedded microprocessor 107 is a position controller that drives the motors in order to reach the desired joint position.

Figure 33:
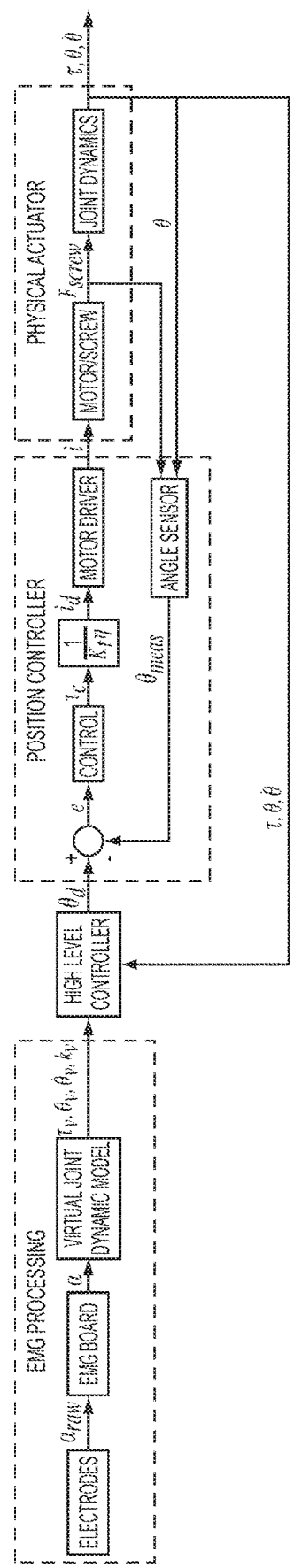
FIG. 33 illustrates the control system as in FIG. 32 when muscle activation levels are processed for input into the control system.

The control system may be used with EMG input from a portable EMG processing board. The control scheme using EMG input is outlined in FIG. 33.

Figure 34A:
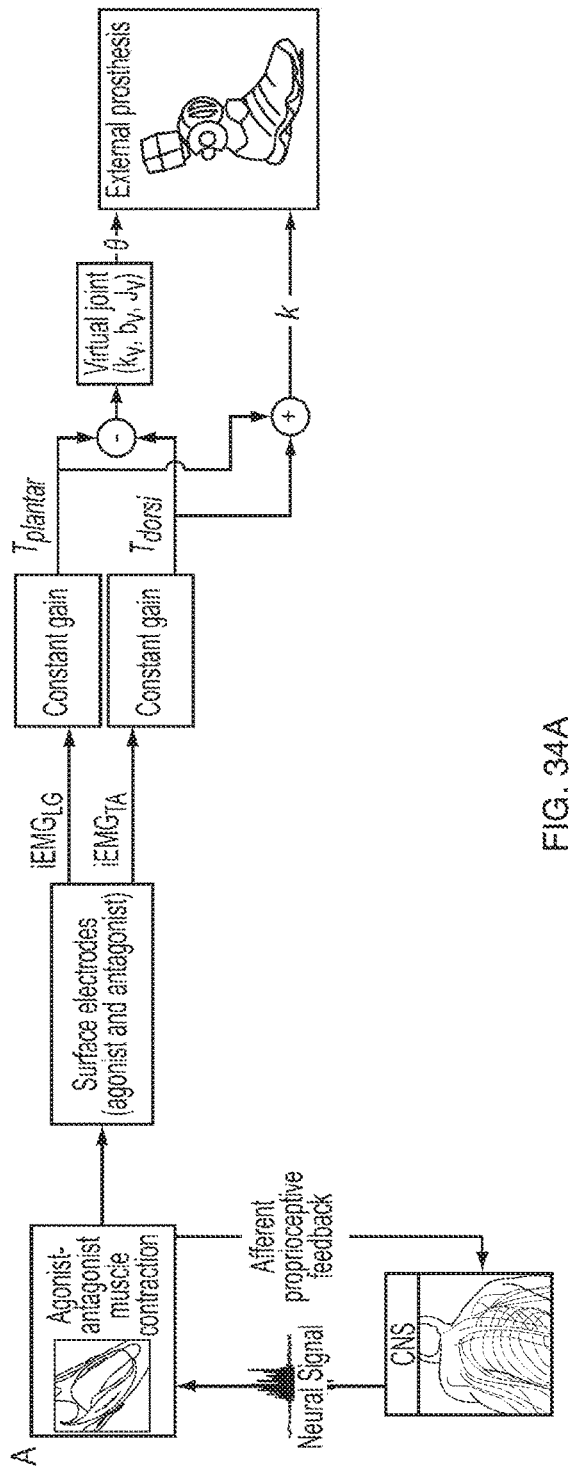
FIGS. 34A and 34B illustrate details of the virtual joint dynamic model shown in the control system in FIG. 33.

One or more EMG input signals may be used to control the device via machine learning, proportional control, or a plurality of mathematical biomechanical models. An example of EMG input processing is virtual joint dynamic modeling, shown in within the "EMG PROCESSING" block in the control diagram of FIG. 33. The details of this model are shown in FIG. 34A. Using this control approach, EMG signal amplitudes recorded from the agonist and antagonist muscles are interpreted as desired torques produced in opposite directions about a virtual dynamic joint, constructed with physiologically-relevant values for virtual parallel spring stiffness, virtual damping, and virtual inertia. The difference of these estimated torques is then applied to the virtual joint, causing it to move. The position of the virtual joint controlled the desired position of the associated prosthetic joint. Prosthetic joint stiffness is directly modulated by the mean activation of the agonist and antagonist muscles. This control architecture enables independent modulation of joint position and impedance. As with all EMG-based proportional control systems, there is a trade-off between joint stability and latency; typically, the particulars of this trade-off are buried in filter design. One benefit to the virtual joint architecture is that filter parameters take on intuitive physical meaning, and can be set to near-physiologic values.

Figure 34B:
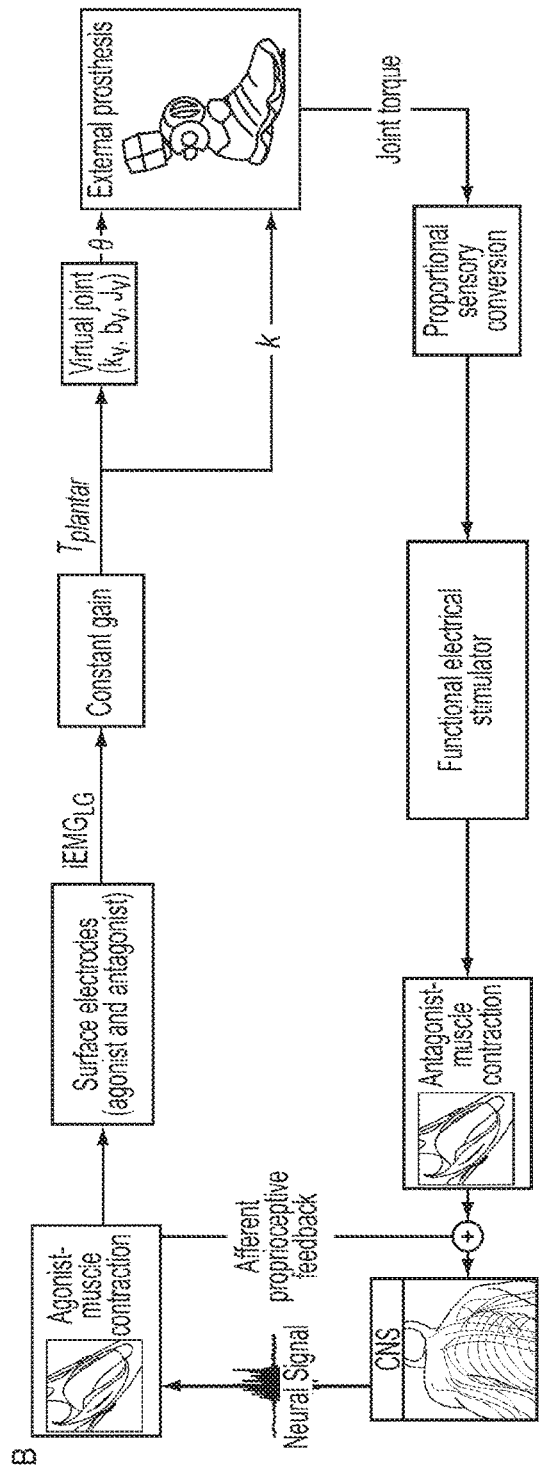

This control architecture may also be used with functional electrical stimulation feedback as shown in FIG. 34B. While stimulation was active for prosthetic joint torque feedback, the stimulated muscle was assumed to be at zero activation, and input from that muscle to the controller was blocked. Although this design eliminates the ability to actively move the joint in the same direction as an applied load, the scenarios in which this action would be desirable are likely to be extremely limited.

Overview of Rotary Cycloidal Drive Actuator

Figure 37D:
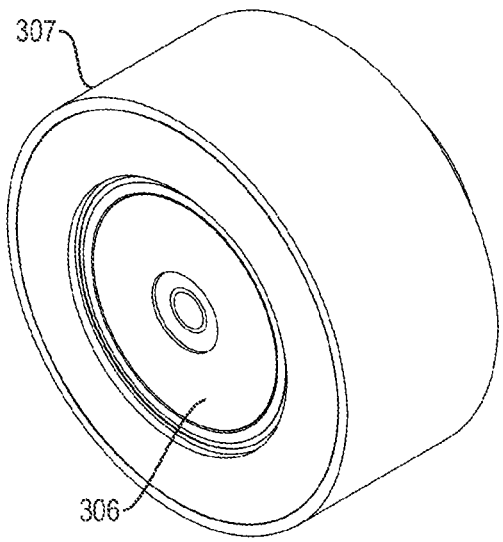
FIGS. 37A, 37B, 37C, and 37D are sectional, front, side, and perspective views, respectively, of a rotary actuator that includes an external rotor electric motor combined with a cycloidal transmission framed within the same housing.
Figure 37C:
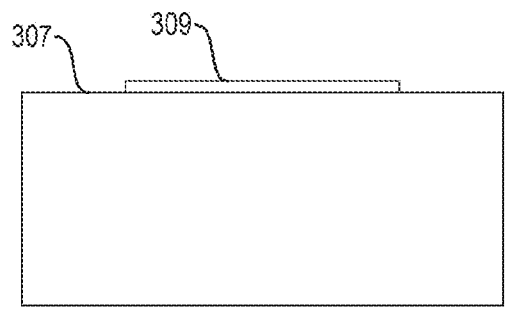
Figure 37B:
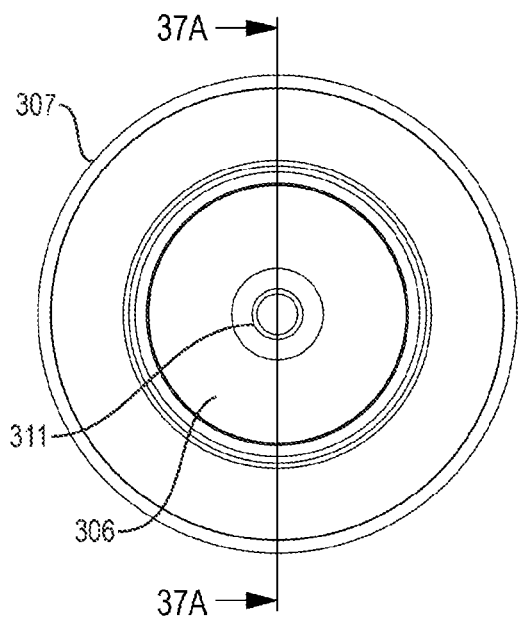
Figure 37A:
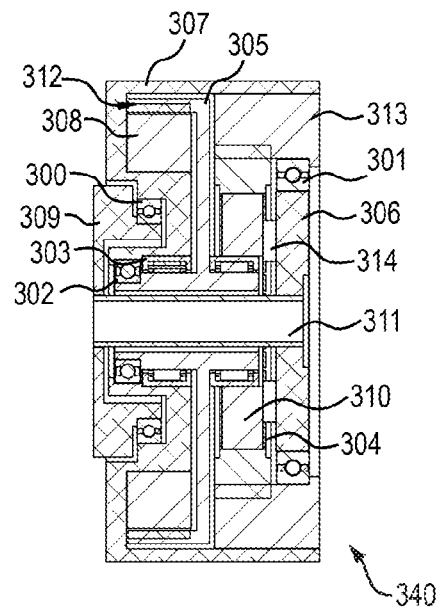
Figure 38C:
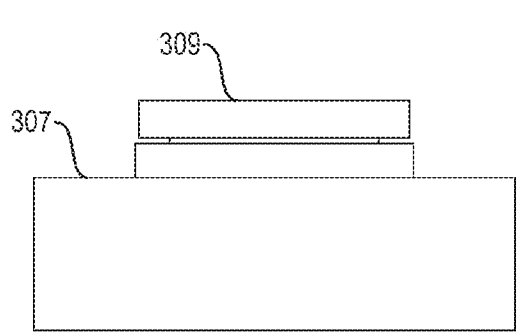
FIGS. 38A, 38B, 38C, and 38D are sectional, front, side, and perspective views, respectively, of a rotary actuator including an external rotor electric motor combined with a cycloidal transmission framed within the same housing, the transmission situated within the same plane as the motor rotor and stator.
Figure 38D:
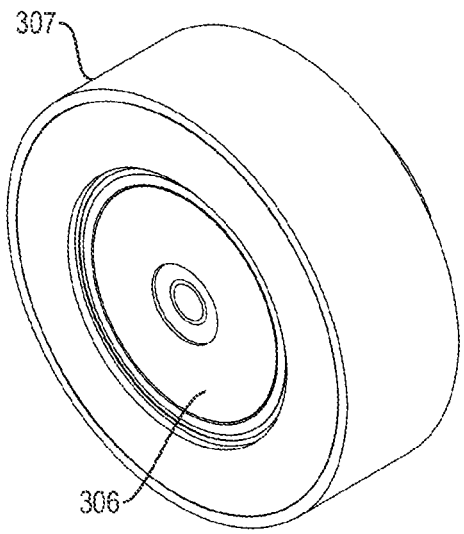
Figure 38B:
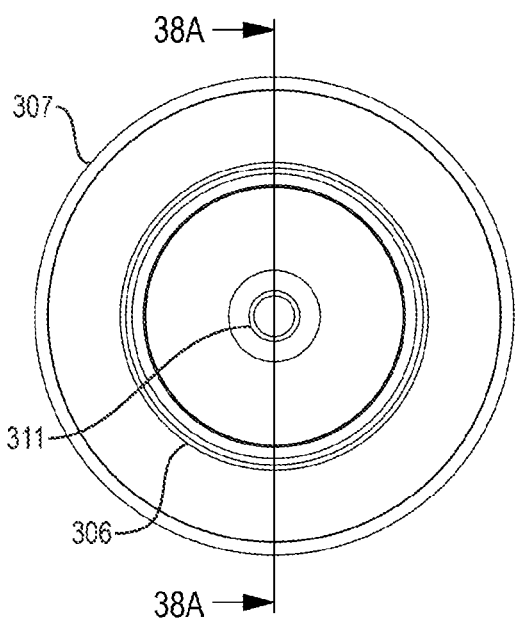
Figure 38A:
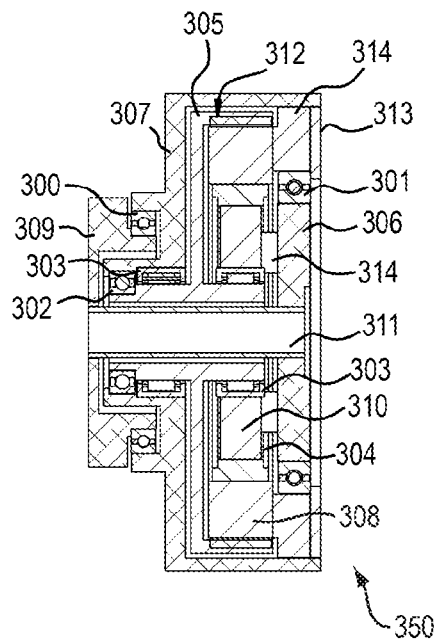
Figure 39:
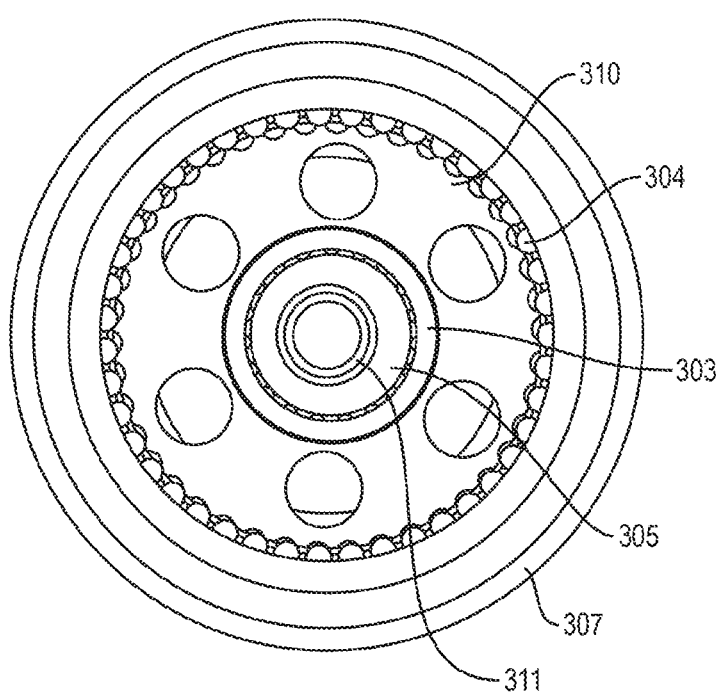
FIG. 39 is a detail view of the cycloidal disk of the rotary actuator of FIG. 38A.

Embodiments of a rotary actuator that includes an electric motor and cycloidal drive are shown in FIGS. 35A-43B. In each of the cases, the components are aligned with the central axis except for the cycloidal disk that moves with some eccentricity about this central axis. A cycloidal drive is a means of producing a reduction in angular velocity between input and output rotary elements. As with all speed reduction transmissions the change in angular velocity also produces a reciprocal change in torque output. The cycloidal speed reduction is based on the epitrochoid curve that results from tracing the point on a circle as it rolls about another circle. The shape of a cycloidal disk is shown in FIG. 39. The resulting motion is a rolling motion of the gear tooth interaction, rather than friction force. FIGS. 40A-41C show variations of the architectures shown in FIG. 35A and FIG. 38A, where the actuator has two cycloidal disks rotated 180 degrees from each other. This allows the rotating elements in the actuator to be dynamically balanced and lower vibration in the actuator. The architecture in FIG. 37A can also be configured with two cycloidal disks. FIG. 42C shows a detail of the two offset eccentric hubs and cycloid disks. In FIGS. 35A-43C, the labeled components have equivalent behavior, while possibly differing in physical arrangement in the device. FIG. 44 shows an example of this actuator used as a single degree of freedom ankle joint. Multiple instance of these actuators can be used together to replicate a multi-degree of freedom biological joint.

Figure 36:
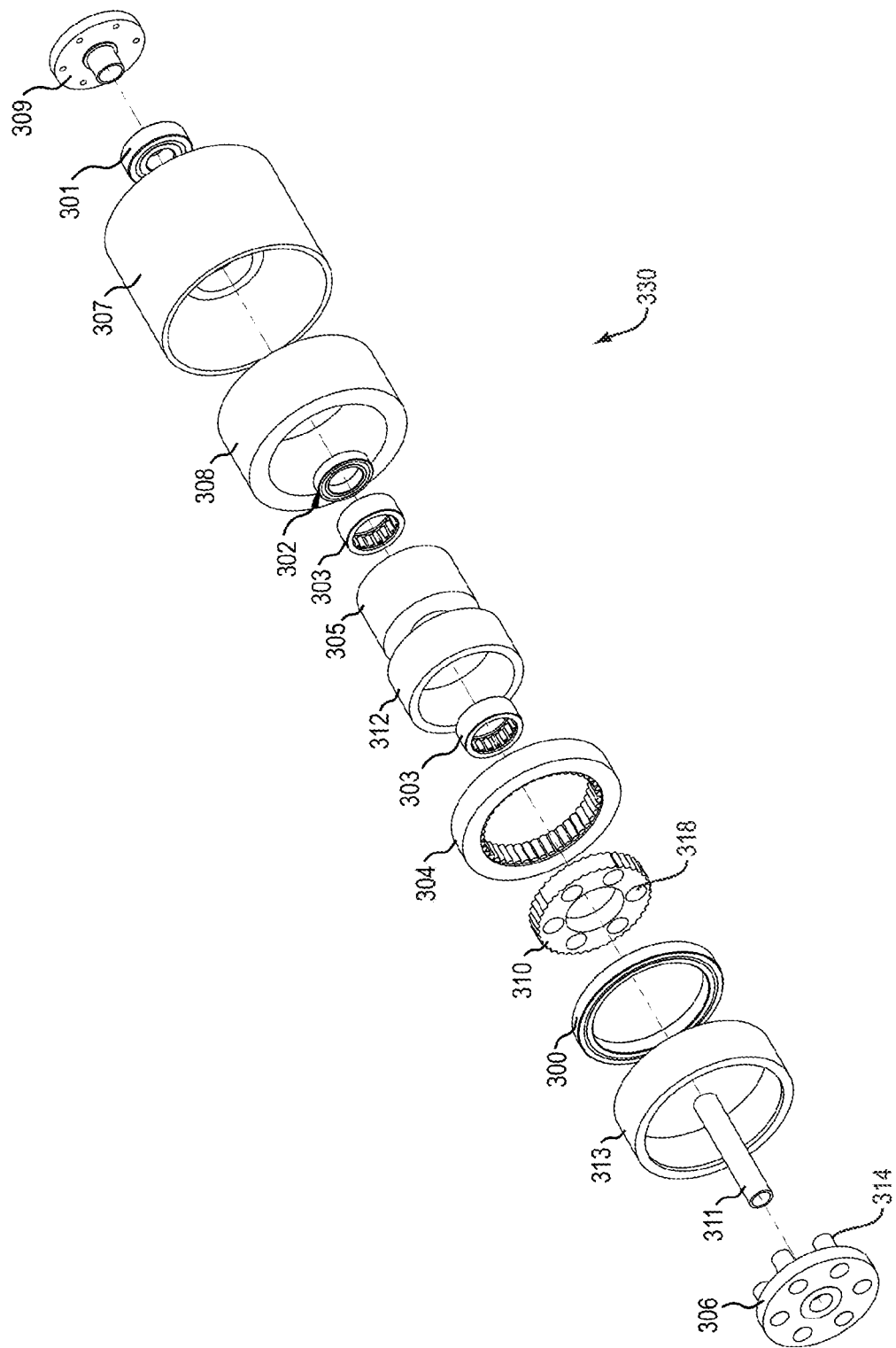
FIG. 36 shows an exploded view of the rotary actuator of FIG. 35A.

Features of embodiments of the rotary cycloidal drive actuator include:

a) Actuator
   i. Cycloidal drive integrated with motor rotor design
   ii. Rotor may be external rotor with respect to stator
   iii. Rotor may be internal rotor with respect to stator
   iv. The electric motor may be a direct current (DC) motor
   v. The electric motor may be a brushless direct current motor (BLDC)
   vi. The electric motor may be a transflux motor.
   vii. Output is possible at the cycloid drive output
   viii. Cycloid drive output may also be connected to series elastic element (SEA), where output is then at the output of the SEA.
   ix. The series elastic element may be a rod or a tube made up from various materials.
   x. Series elastic element can pass through the center axis of the actuator
   xi. The actuator may have a clearance hole through the entire length of the device
   xii. The actuator may be fully enclosed, protecting internals from environmental elements Details of Rotary Cycloidal Drive Actuator FIG. 35A shows the cross section of a rotary actuator 330 with an internal-rotor electric motor. FIGS. 35B-35D provide additional view of the rotary actuator of FIG. 35A. FIG. 36 shows an exploded view of the actuator assembly shown in FIG. 35A, where each component can be seen disassembled. The electric motor may be a brushed direct current motor, a multi-phase brushless direct-current motor, a transverse magnetic flux, (transflux) motor or any other type of motor with an internal rotor and an external stator that remains stationary relative to the actuator housing frame. An advantage of integrating the hypocyloidal or cycloid drive into the motor housing is reduction in number of components, weight and size normally associated with coupling motor and gearbox output and input shafts. Further, integration of components by shared bearings reduce additional structural mass, components and overall dimensions.

Shown in FIG. 35A is the housing 307 of the rotary actuator, which is a static, non-moving frame. Motor stator 308 is mounted rigidly within housing 307. The motor rotor 305 has magnets 312 attached and is freely rotatable but axially secured by rotary bearings 303 and 302. Rotary bearing 303 is mounted on an eccentric hub portion of rotor shaft 305. The rotor includes an inner hub or shaft and an outer rim that carries the rotor magnets 312. The inner hub defines the eccentric hub portion and is axially secured to the housing by the bearings 303 and 302. The outer rim of the rotor is configured to rotate within the stator 308. The cycloidal disk 310 rides on bearing 303 and traverses in a counter rotating direction from the input rotor. The cycloidal disk's outer circumferential track travels across rollers (or pin shapes) of roller housing 304. The rollers can be rigidly mounted or separate elements that may freely rotate. The gear reduction is determined by the overall number of roller shapes, $n\_h$, in roller housing 304, and number of teeth (or lobes) of cycloidal disk 310, $n\_c$, by $N=(n\_h-n\_c)/n\_h$. The output of the reduction comes from the output drive pins 314 (FIG. 36) that are built into the output shaft 306 and engage holes 318 of the cycloidal disk 310. The output shaft 306 is radially secured with bearing 300. In this embodiment, output shaft 306 is also attached to a series elastic torsional element 311. Torque is transmitted through this torsional shaft 311 and stores energy in rotary strain of this element. A final output disk 309 is attached to the opposing end of the series element 311 and supported radially and axially by bearing element 301 that is also grounded to actuator housing 307. Rotary encoders (not shown) can be utilized to measure the relative deflection of final output 309 with respect to cycloid output 306. The deflection measured directly relates to the amount of energy stored as well as force applied to the actuator output at 309.

Thus, there is provided a rotary actuator 330 that includes a housing frame 307, a motor mounted within the housing frame and including a rotor 305 and a stator 308, and a cycloidal drive coupled to the motor within the housing frame. The rotor includes an eccentric hub portion. The cycloidal drive includes a rotary bearing 303 mounted on the eccentric hub portion, a cycloidal disk 310 riding on the rotary bearing and including holes, and an output shaft 306 driven by the cycloidal disk, the output shaft coupled to the cycloidal disk via output pins that extend through the holes of the cycloidal disk.

FIGS. 37A-37D show a rotary actuator 340 composed of the same or similar components as that of FIGS. 35A-36 except the motor rotor rotates external to the stator rather than internally. Also shown in FIG. 37A are rotor magnets 312 attached to an outer rim of rotor 305. Motor stator 308 is rigidly attached to actuator housing frame 307. Rotary bearings 303 support radial forces from the rotor 305 and cycloidal disk 310, while radial bearing 302 supports axial force from the rotor and both bearings passes these forces to the actuator housing 307. All other components are similar to those of FIGS. 35A-36, except additional component 313 helps attach the roller housing 304 and bearing 301 to the frame. This component may also be made part of the roller housing 304 or other similar embodiments of space filling elements.

FIGS. 38A-38D shows another rotary actuator 350 that includes components of similar functionality to those in FIGS. 35A-36, the difference being, similar to FIG. 37A, motor rotor 305 is located external to motor stator 308, and cycloidal rollers 304 and cycloid disk 310 are arranged such that they are within the similar plane of action as the motor coils and magnets 312, such that they fit within the inner diameter of motor stator 308. Again cycloid disk 310 rides on bearing 303 that sits on an eccentrically offset diameter attached to motor rotor 305. The rotor is supported primarily radially by another bearing 303 and axially by bearing 302, which are then grounded to actuator housing 307. The stator 308 is attached to actuator housing 307 through a rigid space filling element 314. This element 314 may also support cycloid drive output bearing 301. Also shown is a bearing pressure flange 313, though this is a detail anyone skilled in the art of mechanical design may devise in one manner or another. Again, cycloid drive output 306 supported in bearing 301 is also attached to a torsional spring element 311. Output disk 309 is attached to shaft element 311, and is supported by bearing 300 that finally grounds some reaction load to the rotary actuator housing 307.

The shaft 311 may act as a rigid component or a series spring to store energy and it may also be used for deflection to measure output torque by measurement of the difference in rotary position of cycloid drive output 306 and output disk 309. The output of the rotary actuator can be taken directly at cycloid drive output 306, or it can be taken at the output disk 309.

FIG. 39 shows a view of the cycloidal disk 310, its eccentric mounting on rotor 305, and how the difference in teeth of disk 310 and the number of rollers 304 interact. Also visible is shaft 311 that passes back through the actuator, and the rotary housing frame 307.

FIGS. 40A-40D show a rotary actuator 360 with double cycloid disks and with an internal-rotor electric motor. As in other embodiments, the electric motor may be a brushed direct current motor, a multi-phase brushless direct-current motor, a transverse magnetic flux, (transflux) motor or any other type of motor with internal rotor and external stator remains stationary relative to the actuator housing frame. The housing 307 is a static, non-moving frame. Motor stator 308 is mounted rigidly there within housing 307. The motor rotor 305 has magnets 312 attached and is freely rotatable, but axially secured by rotary bearings 303 and 302. Two rotary bearings 303 are mounted on two eccentric hub portions of rotor shaft 305. The cycloidal disks 310 and 315 ride on bearings 303 and traverses in counter rotating directions from the input rotor, 180 degrees out of phase from each other. The cycloidal disk outer circumferential track travels across the rollers (pin shapes) of roller housing 304. The rollers can be rigidly mounted or separate pins that may freely rotate. The gear reduction is determined by the overall number of roller shapes in roller housing 304, by N-1. The output of the reduction comes from the output drive pins 306 built into the output shaft. The output shaft is radially secured with bearing 300. In this embodiment output shaft 306 is also attached to a series elastic torsional element 311. Torque is transmitted through this torsional shaft 311 and stores energy in rotary strain of this element. A final output disk 309 is attached to the opposing end of the series element and supported radially and axially by bearing element 301 that is also grounded to actuator housing 307. Rotary encoders not shown can be utilized to measure the relative deflection of final output 309 with respect to cycloid output 306. The deflection measured directly relates to the amount of energy stored as well as force applied to the actuator output at 309. If sealed bearings are used for 301 and 300, the inside of this actuator is sealed off and can be cycled with a cooling fluid to provide active cooling to the actuator, maximizing the power output of the actuator and minimizing thermal effects. Cooling fluid can enter and exit the actuator through inlet/outlet ports 316 and 317.

Figure 40C:
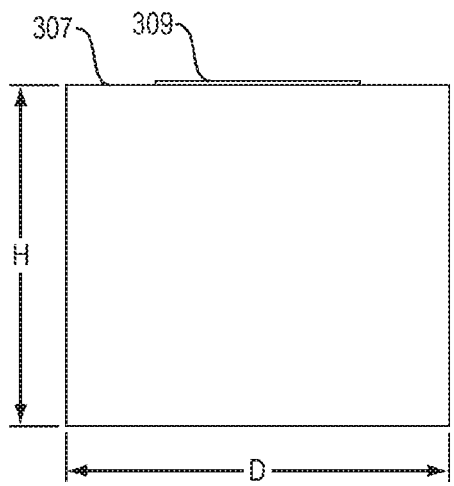
FIGS. 40A, 40B, 40C, and 40D are sectional, front, side, and perspective views, respectively, illustrating a rotary actuator with dual cycloidal disks and an internal rotor motor model and series elastic element.
Figure 40D:
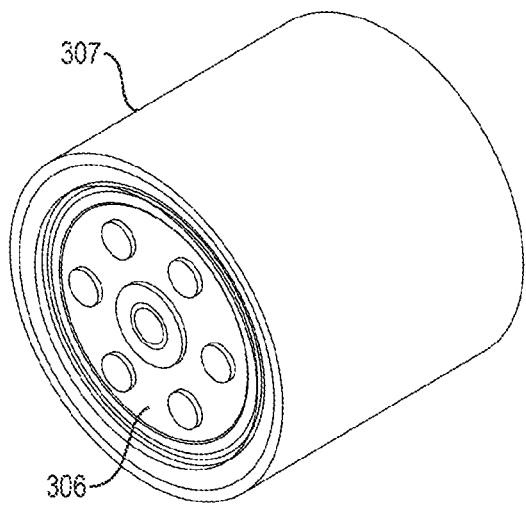
Figure 40B:
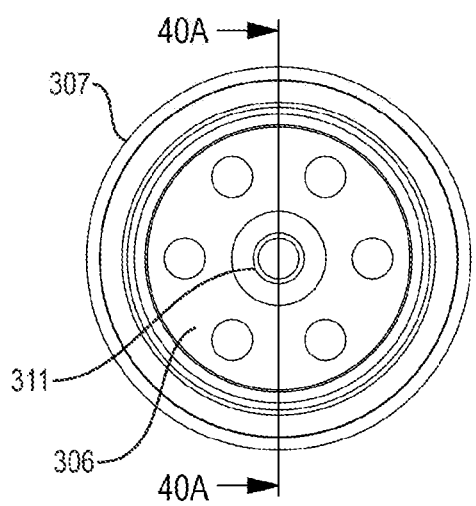

As illustrated in FIG. 40C, the rotary actuator can have a height H and a diameter D. In an embodiment, the height H is about 60 mm and the diameter D about 74 mm.

Figure 40A:
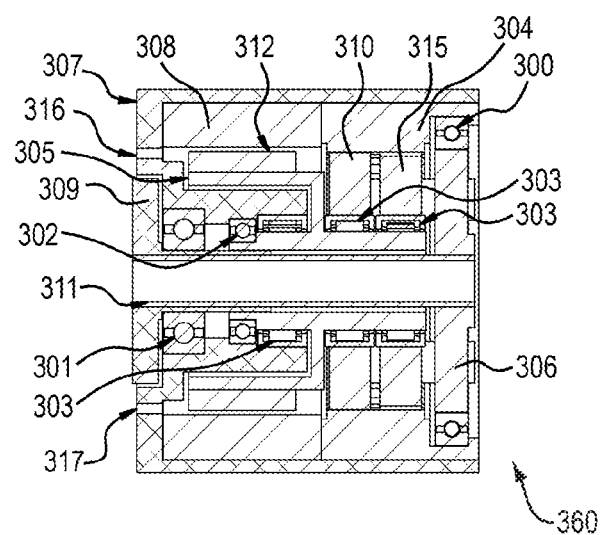

FIGS. 41A-41D show a rotary actuator 370 that includes components of similar architecture as the actuator shown in FIG. 38A, the difference being, similar to FIG. 40A, this design has two cycloid disks 310, 315. Again, each cycloid disks rides on bearings 303 that sit on an eccentrically offset diameters attached to motor rotor 305. The rotor is supported primarily radially by another bearing 303 and axially by bearing 302, which are then grounded to actuator housing 307. The stator 308 is attached to actuator housing 307 through a rigid space filling element 314. This element 314 may also support cycloid drive output bearing 301. Also shown is a bearing presser flanged 313, though this is a detail anyone skilled in the art of mechanical design may devise in one manner or another. Cycloid drive output 306, supported in bearing 301, is attached to a torsional spring element 311. Output disk 309 is attached to shaft element 311, and is supported by bearing 300 that finally grounds some reaction load to the rotary actuator housing 307. The shaft 311 may act as a rigid component or a series spring to store energy and it may also be used for deflection to measure output torque by measurement of the difference in rotary position of cycloid drive output 306 and output disk 309. The output of the rotary actuator can be taken directly at cycloid drive output 306, or it can be taken at the output disk 309. This embodiment of the actuator can also be fully sealed to allow for active liquid cooling through inlet/outlet ports 316 and 317. The architecture in FIG. 37A can also be configured with two cycloid disks as well.

Figure 41C:
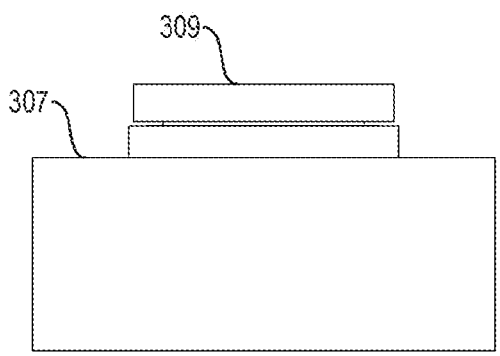
FIGS. 41A, 41B, 41C, and 41D are sectional, front, side, and perspective views, respectively, of a rotary actuator with dual cycloidal disks and an external rotor motor and series elastic element.
Figure 41D:
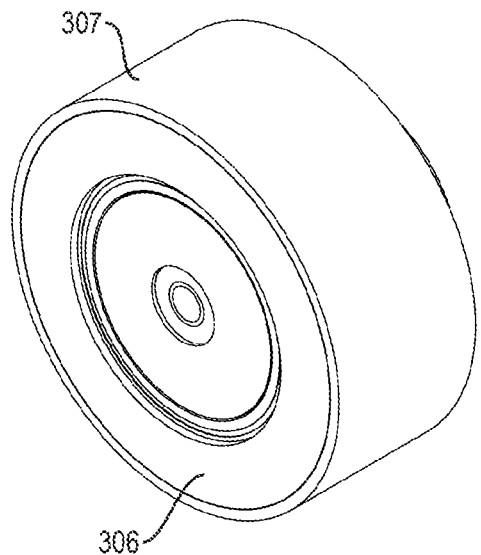
Figure 41B:
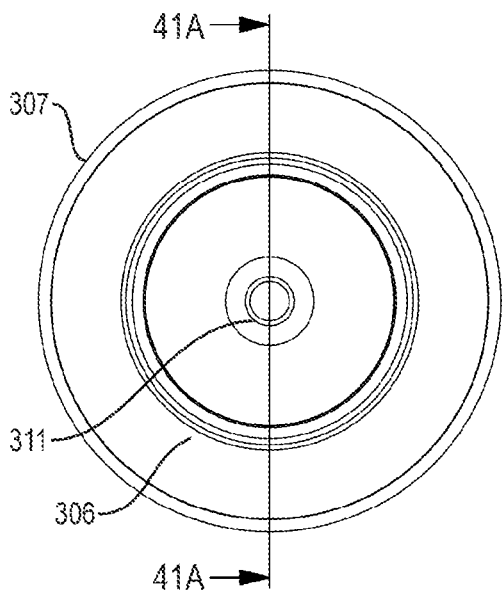
Figure 41A:
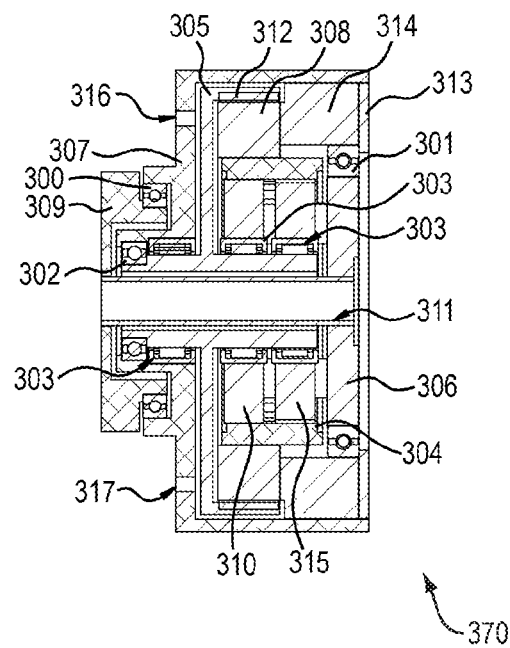
Figure 42A:
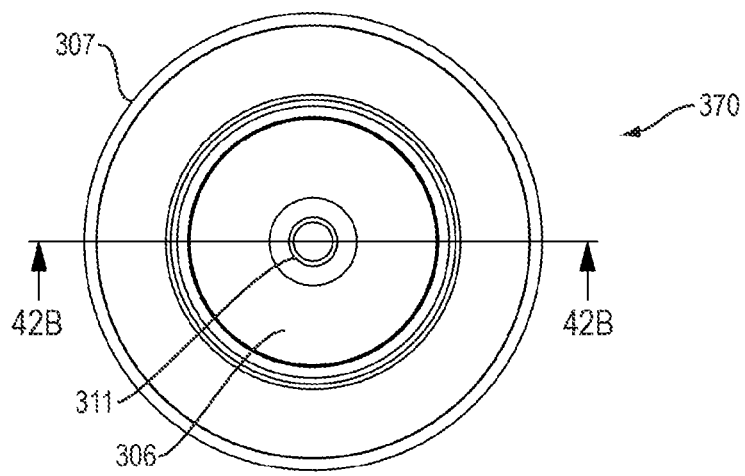
FIGS. 42A, 42B, and 42C, are additional front, sectional, and detail views, respectively, of the rotary actuator with dual cycloidal disks of FIG. 41A.
Figure 42B:
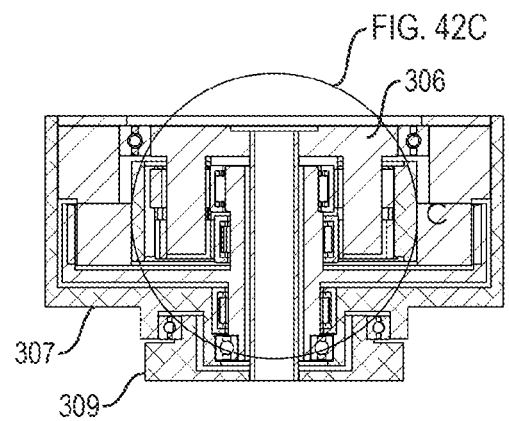
Figure 42C:
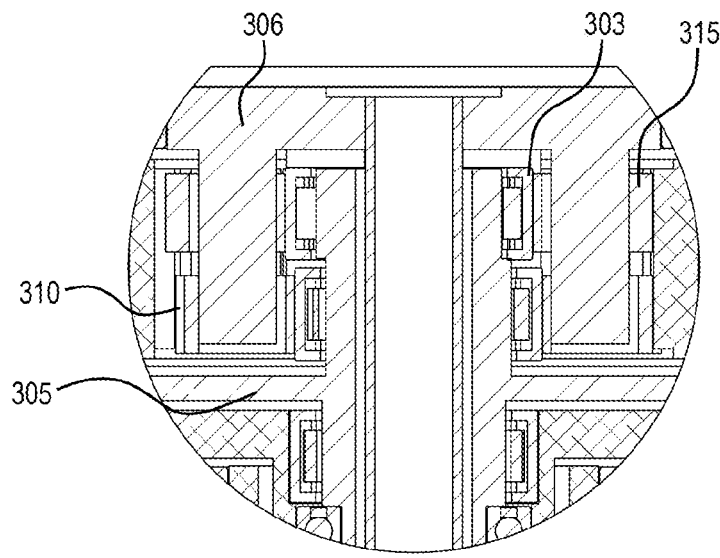

FIG. 42C is a detail view showing both eccentric hubs and two cycloid disks offset in opposite directions from each other in the actuator configuration 370 of FIG. 41A. Each disk rides on a different eccentric hub portion of the rotor 305. Both disks 310, 315 will rotate together at the same speed to transmit the motion and torque to the output disk 306.

Figure 43A:
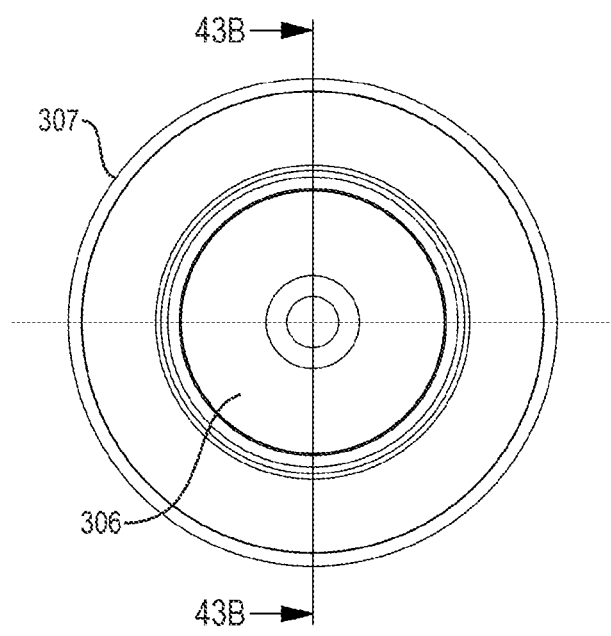
FIGS. 43A and 43B are front and section views of a rotary actuator with dual cycloidal disks, an external rotor motor, and no series elastic element.
Figure 43B:
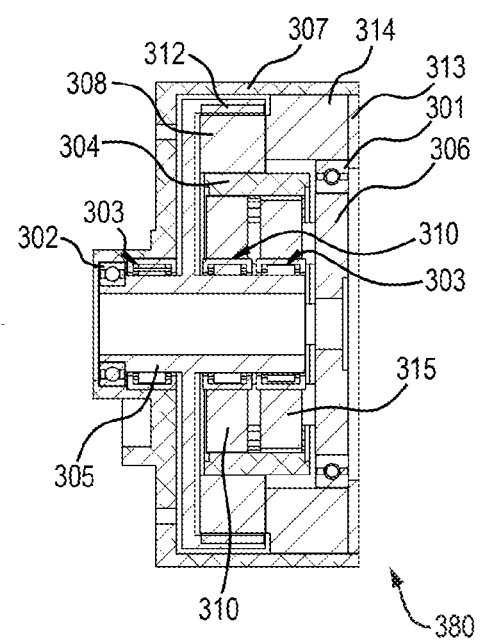

FIGS. 43A-43B show a configuration 380 of the architecture in FIG. 41A without the series elastic element through the center of the actuator, the final output disk, and the final output bearing. This configuration allows for a smaller and lighter actuator package. Bearing 301 can withstand axial, radial, and moment loads to support the single output disk 306 through the use of a cross-roller bearing, 4-point bearing, or functionally similar bearing.

Figure 44A:
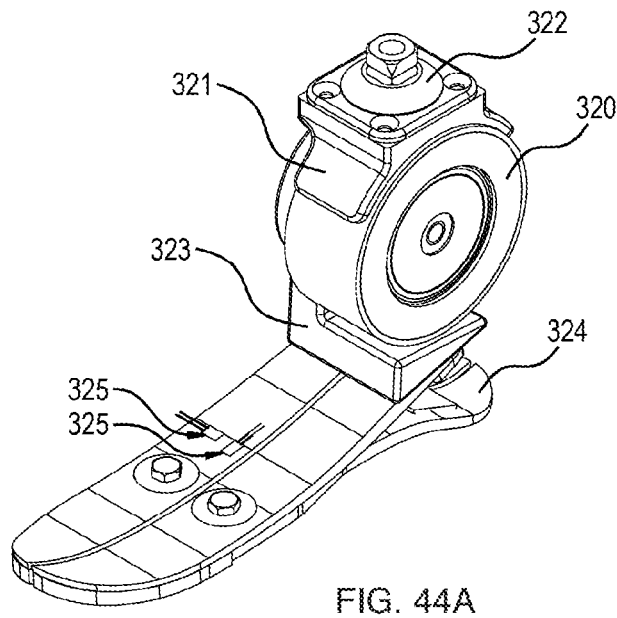
FIGS. 44A, 44B, and 44C are perspective, side, and back views showing a rotary actuator configured as an ankle joint with a foot and a pyramid adapter attached to the actuator.
Figure 44B:
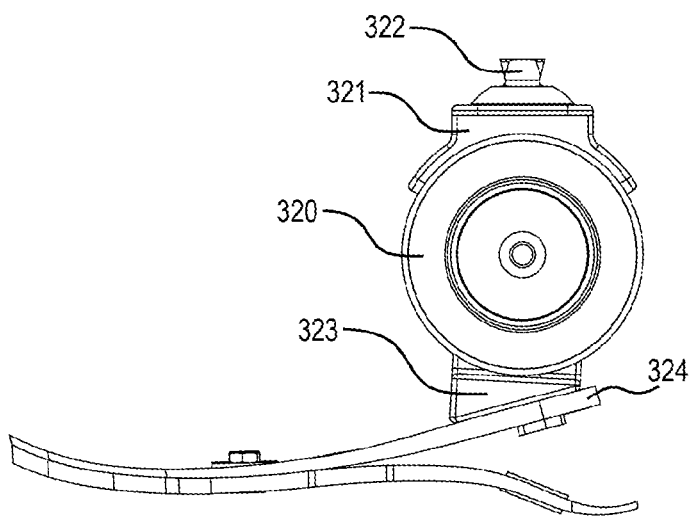
Figure 44C:
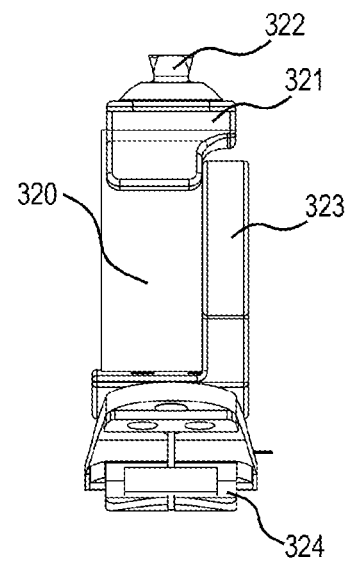

FIGS. 44A-44C show the use of the rotary actuator 320 as a single degree of freedom ankle prosthesis. The actuator configuration used in this figure is that of FIG. 41A, with a rigid shaft passing through the center. All configurations of the rotary actuators described herein can be used in a similar fashion. As the rotary actuator has no limit to degree of motion, this design allows for a large range of motion of the biological joint only limited by the geometry of the structural components. A knee joint, elbow join, wrist joint, or any other prosthetic joint could be used by making different structural attachments to the appropriate interface components such as male or female adapters. Multiple actuators can be used in conjunction to add degrees of freedom.

In FIG. 44A, the rotary actuator 320 is rigidly attached by its outer housing (e.g., housing frame 307) to a structural mount 321, which acts as an adapter to a standard prosthesis pyramid attachment 322. The output of the actuator is attached to a foot structural mount 323. A prosthetic foot 324 is attached to the foot mount 323. In this embodiment, the prosthetic foot 324 is a tuned spring, the rotary actuator 320 is rigid, and the whole prosthesis acts as a series elastic actuator. The strain gauges 325 are attached on the foot spring 324 to measure the strain in the spring, which is then used to calculate the deflection of the spring. The deflection directly relates to the amount of energy stored as well as force applied to the actuator output. A Poisson half-bridge circuit using the two strain gauges 325 shown in FIG. 44A or full Wheatstone bridge circuit using four strain gauges can be used to obtain accurate strain values.

Thus, there is provided a prosthetic ankle device that includes a rotary actuator 320 defining an ankle axis of rotation, the rotary actuator including a housing frame 307, a motor mounted within the housing frame, a rotary output, and a cycloidal drive positioned within the housing frame and coupling the motor to the rotary output. A prosthetic foot 324 is connected to the rotary output and the rotary actuator 320 is configured to rotate the prosthetic foot about the ankle axis of rotation. The rotary actuator can include a shaft extending through the motor and the cycloidal drive, the shaft coupling the cycloidal drive to the output of the actuator.

Walking Mode Control

In another embodiment, the invention is a device that has an intrinsic control system to monitor orientation of the device and adjusts joint angle to achieve desired orientation during swing, using information from onboard sensors such as accelerometers or inertial measurement units (IMUs).

A combination of intrinsic and EMG control systems can be used to control the device. For example, EMG input is used to allow the user to selectively adjust the equilibrium point of the series spring. Sensor data can be processed by the onboard microcontroller to determine optimum spring equilibrium point based on terrain, utilizing prior techniques developed for terrain detection. The actuators may be driven in the same direction as biological joint motion to create a dampening effect at relevant portions of the gait cycle.

In an embodiment, the system features a method for automatic learning of task transitions for the purpose of controlling the device in a way that corresponds to each task.

In an embodiment, the system features a way to incrementally train a task classifier based on features estimated in real time from prosthesis sensors and a reliable method of back-estimating the terrain after a stride has been taken.

In an embodiment, the back estimation algorithm relies on sensors on board the prosthesis to determine what kind of terrain the prosthesis user stepped on, and then employs this new label to add a data point to an incremental machine learning architecture. This data point updates a terrain classifier used for terrain prediction.

In an embodiment, the back estimation algorithm employs ankle angle when the foot is on the ground to determine whether you are on a sloped surface, to determine if the surface is upsloping, flat, or downsloping, and to estimate the angle of the slope.

In an embodiment, the back estimation algorithm uses inertial motion trajectory of the ankle or knee to determine the geometry of the terrain and consequently the terrain class or identity.

In an embodiment the back estimation algorithm improves the accuracy of the inertial motion trajectory between two time points at which the foot was known to be static.

Figure 45:
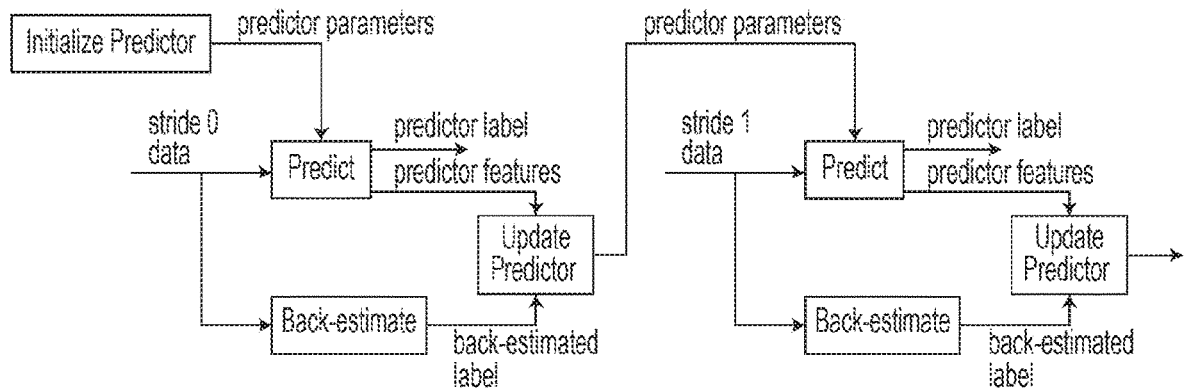
FIG. 45 shows incremental learning algorithm for walking mode prediction.

FIG. 45 shows overall architecture of the incremental learning algorithm. An LDA classifier is initialized with zero means and an identify covariance matrix. Subsequently, each new stride undergoes a prediction and back-estimation step. In prediction, the current LDA classifier is applied to predict the next terrain. In back-estimation, the stride is labeled post completion and the LDA classifier parameters are updated with the new training data.

Terrain prediction can be used with the ankle-foot prosthesis illustrated in FIG. 9, which has a large 115-degree total range of motion with 35 degrees of dorsiflexion.

Figure 46A:
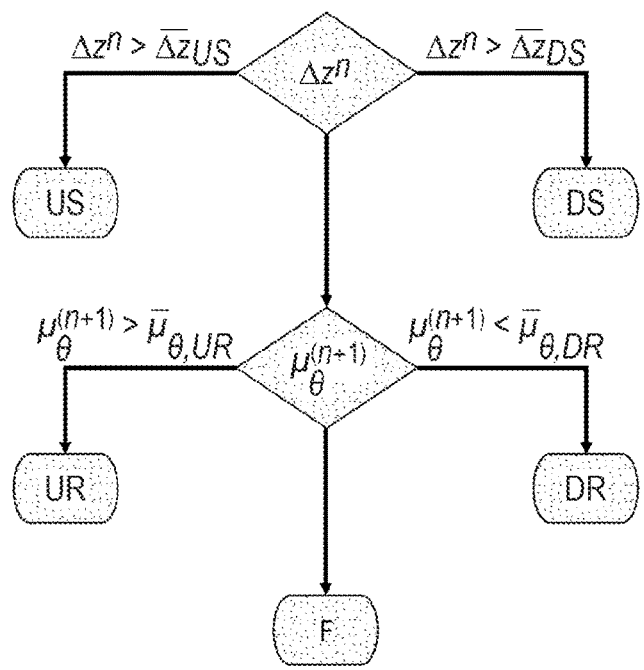
FIGS. 46A and 46B illustrate heuristic back-estimation of stride terrain algorithm.
Figure 46B:
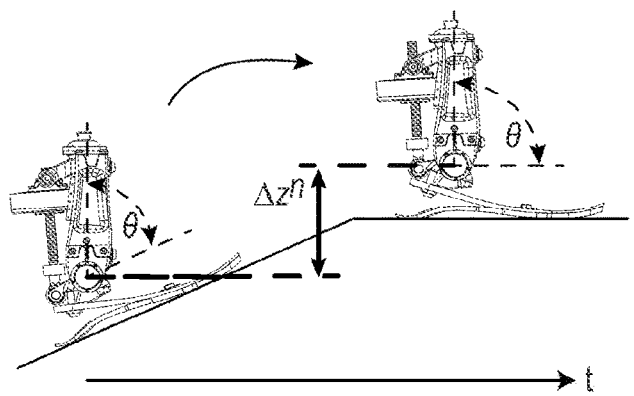

FIG. 46A shows heuristic back-estimation of stride terrain based on vertical ankle joint position in swing and mean joint angle in stance. A visualization of these parameters for a representative terrain transition is also shown in FIG. 46B.

Figure 47:
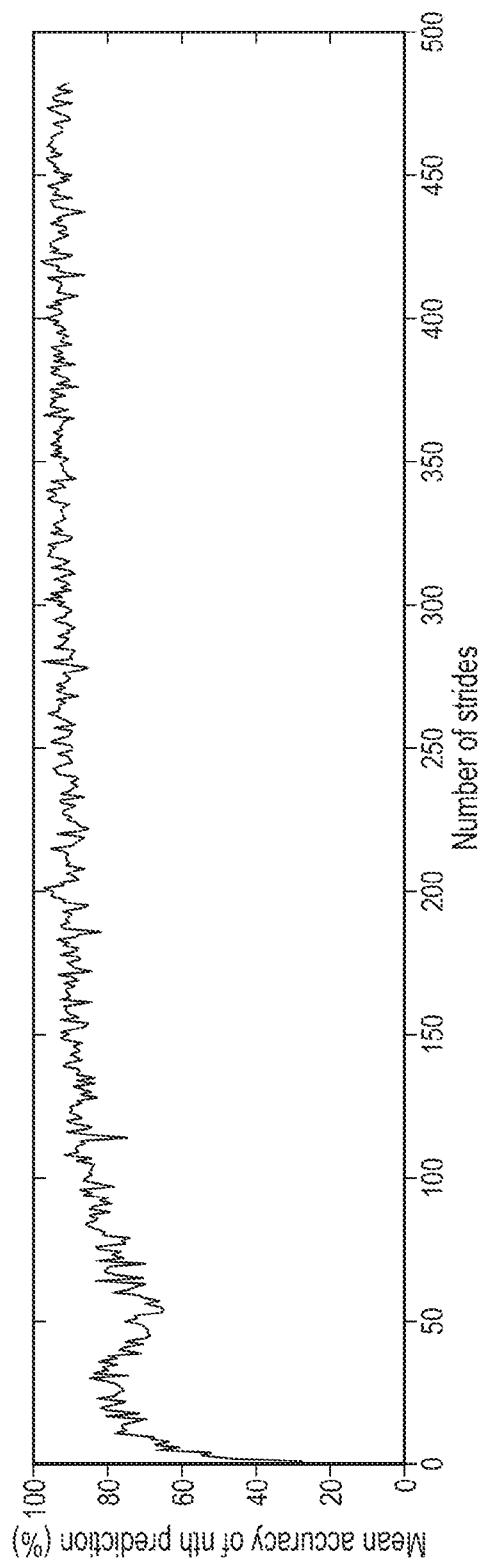
FIG. 47 is a graph showing mean next-stride prediction accuracies.

FIG. 47 shows mean next-stride prediction accuracies from 100 simulations randomizing stride order for a series of strides collected on a subject walking on a variety of terrains wearing the ankle-foot prosthesis.

The relevant teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A prosthetic device, comprising:
    a frame defining an output axis;
    a cantilever beam spring having a first end attached to the frame and a second end;
    a moment arm attached to the second end of the cantilever beam spring;
    a rigid output arm coupled to the frame and rotatable about the output axis;
    a connector assembly connecting the moment arm to the output arm, the connector assembly coupled to the moment arm by a moment pivot and coupled to the output arm by an output pivot located at a distance from the output axis, the connector assembly configured to apply a moment to the cantilever beam spring via the moment arm while applying a torque about the output axis via the output arm; and
    a carriage translatable along a length of the cantilever beam spring, the carriage forming a structural pivot for dynamic control of deformation of the cantilever beam spring to provide for a variable spring stiffness.

2. The device of claim 1, wherein the connector assembly is configured to vary the distance between the moment pivot and the output pivot.

3. The device of claim 1, wherein the connector assembly is configured to set the distance between moment pivot and the output pivot at a fixed length.

4. The device of claim 1, wherein the connector assembly comprises a linear actuator.

5. The device of claim 1, wherein the connector assembly comprises a mechanical transformer that converts rotary motion into linear motion.

6. The device of claim 5, wherein the mechanical transformer is backdriveable.

7. The device of claim 6, wherein the mechanical transformer comprises a motor, a screw passing through the motor, and a nut rotatable about the screw, the motor configured to rotate the nut, rotation of the nut causing linear motion of the screw relative to the motor.

8. The device of claim 7, wherein the linear motion of the screw creates load on the output arm and rotary motion of the output arm about the frame.

9. The device of claim 7, wherein the motor includes a rotor and the nut is integrated into the rotor, rotation of the rotor causing the linear motion of the screw.

10. The device of claim 9, wherein the motor includes a stator coupled to the moment pivot at the moment arm, and wherein an end of the screw is coupled via a push rod to the output pivot at the output arm.

11. The device of claim 10, further comprising a load cell between the screw and the push rod, to measure load on the screw.

12. The device of claim 1, further comprising a rotary encoder at the frame to measure rotation of the output arm about the frame.

13. The device of claim 5, wherein the mechanical transformer is non-backdriveable.

14. The device of claim 13, wherein the mechanical transformer comprises a screw and a nut configured to rotate about the screw, rotation of the nut causing linear motion of the screw.

15. The device of claim 14, wherein the mechanical transformer further comprises a motor configured to provide rotation of the nut.

16. The device of claim 15, wherein the rotation of the nut is by means of meshing gears, friction drive, or belt drive transforming motion of the motor to rotation of the nut.

17. The device of claim 1, further comprising a rotatable beam screw that extends parallel to the cantilever beam spring and engages a nut coupled to the carriage, rotation of the beam screw causing linear motion of the carriage along a length of the cantilever beam spring.

18. The device of claim 17, further comprising a drive motor for providing rotation of the beam screw.

19. The device of claim 1, further comprising a carriage and a shock absorber that extends parallel to the cantilever beam spring and engages the carriage, the shock absorber providing linear motion of the carriage along a length of the cantilever beam spring.

20. The device of claim 1, wherein the device is a prosthetic ankle device and the output arm engages a prosthetic foot.

21. The device of claim 1, wherein the device is a prosthetic knee device and the output arm engages a prosthetic limb or a prosthetic socket.

22. The device of claim 1, further comprising one or more support arms attached to the frame and supporting a base plate, wherein the base plate supports an attachment for a prosthetic limb or a prosthetic socket.

23. The device of claim 22, further comprising a prosthetic socket attached at the base plate, the prosthetic socket including a battery mount fixture to secure a battery at the socket and an electronics mount fixture to secure electronic circuitry powered by the battery at the socket.

24. A prosthetic knee device, comprising:
a frame defining an output axis;
a cantilever beam spring having a first end attached to the frame and a second end;
a moment arm attached to the second end of the cantilever beam spring;
a rigid output arm coupled to the frame and rotatable about the output axis; and
connector assembly connecting the moment arm to the output arm, the connector assembly coupled to the moment arm by a moment pivot and coupled to the output arm by an output pivot located at a distance from the output axis connector assembly configured to apply a moment to the cantilever beam spring via the moment arm while applying a torque about the output axis via the output arm, the output arm engaging a prosthetic limb or a prosthetic socket.

* * * * *